US008575311B2

(12) United States Patent
Chmielewski et al.

(10) Patent No.: US 8,575,311 B2
(45) Date of Patent: Nov. 5, 2013

(54) COLLAGEN PEPTIDE CONJUGATES AND USES THEREFOR

(75) Inventors: Jean A Chmielewski, Lafayette, IN (US); Marcos M Pires, West Lafayette, IN (US); David E Przybyla, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 207 days.

(21) Appl. No.: 12/992,759

(22) PCT Filed: May 15, 2009

(86) PCT No.: PCT/US2009/044093
§ 371 (c)(1),
(2), (4) Date: Nov. 15, 2010

(87) PCT Pub. No.: WO2009/140573
PCT Pub. Date: Nov. 19, 2009

(65) Prior Publication Data
US 2011/0081324 A1 Apr. 7, 2011

Related U.S. Application Data

(60) Provisional application No. 61/053,420, filed on May 15, 2008.

(51) Int. Cl.
*C07K 14/00* (2006.01)
(52) U.S. Cl.
USPC .......................................................... 530/350
(58) Field of Classification Search
USPC .......................................................... 530/350
See application file for complete search history.

(56) References Cited

U.S. PATENT DOCUMENTS 8,283,414 B2 * 10/2012 Yu et al. ........................ 525/54.1

FOREIGN PATENT DOCUMENTS

WO WO2007044026 4/2007

OTHER PUBLICATIONS

International Search Report/Written Opinion completed Jun. 13, 2009 for PCT/US2009/044093.
Bishop, Barney M., et al., "4'-Aminomethyl-2,2'-Bipyridyl-4-Carboxylic Acit (Abc) and Related Derivatives: Novel Bipyridine Amino Acids for the Solid-Phase Incorporation of a Metal Coordination Site Within a Peptide Backbone", 2000, Tetrahedron vol. 56, pp. 4629-4638.
Chaouk, Hassan, et al., "New Ligand, N-(2-Pyridylemthyl)Aminoacetate, for use in the Immobilised Metal Ion Affinity Chromatographic Separation of Proteins", 1999, Journal of Chromatography A, vol. 852, pp. 105-115.
Kinberger, Garth A., et al., "FeIII-Binding Collagen Mimetics", 2006, Inorganic Chemistry, vol. 45, No. 3, pp. 961-963.
Koide, Takaki, et al., "Metal-Assisted Stabilization and Probing of Collagenous Triple Helices", 2002, J. Am. Chem. Soc., vol. 124., pp. 9388-9389.
Koide, Takaki, et al., "Designed Triple-Helical Peptides as Tools for Collagen Biochemistry and Matrix Engineering", 2007, Phil. Trans. R. Soc. B, vol. 362., pp. 1281-1291.
Burdick et al., "Engineered Microenvironments for Controlled Stem Cell Differentiation," Tissue Engineering, vol. 15, 205-219 (2009).
Pires et al., "Self-assembly of Collagen Peptides into Microflorettes via Metal Coordination," J. Am. Chem. Soc., vol. 131, 2706-2712 (2009).
Fischbach et al., "Cancer cell angiogenic capability is regulated by 3D culture and integrin engagement," Proc. Natl. Acad. Sci. U.S.A., vol. 106, 399-404 (2009).
Przybyla et al., "Metal-Triggered Radial Self-Assembly of Collagen Peptide Fibers," J. Am. Chem. Soc., vol. 130, 12610-12611 (2008).
Pomerantz et al., "Nanofibers and Lyotropic Liquid Crystals from a Class of Self-Assembling β-Peptides," Angew. Chem. Int. Ed., vol. 47, 1241-1244 (2008).
Murasato et al., "Self-Assembly of Nanofiber with Uniform Width from Wheel-Type Trigonal-β-Sheet-Forming Peptide," Biomacromolecules, vol. 9, 913-918 (2008).
Molchanova et al., "Effects of Growth Factors on Multipotent Bone Marrow Mesenchymal Stromal Cells," Biology Bulletin, vol. 35, 555-570 (2008).
Dvir-Ginzberg et al., "Regulation of Cartilage-specific Gene Expression in Human Chondrocytes by SirT1 and Nicotinamide Phosphoribosyltransferase," Jour. of Biol. Chem. vol. 283, No. 52, 36300-36310 (2008).
Dong et al., "Self-Assembly of r-Helical Coiled Coil Nanofibers," J. Am. Chem. Soc., vol. 130, 13691-13695 (2008).
Diana et al., "Structural Determinants of the Unusual Helix Stability of a De Novo Engineered Vascular Endothelial Growth Factor (VEGF) Mimicking Peptide," Chemistry, vol. 14, 4164-6 (2008).
Cejas et al., "Thrombogenic collagen-mimetic peptides:Self-assembly of triple helix-based fibrilsdriven by hydrophobic interactions," Proc. Natl. Acad. Sci. U.S.A., vol. 105, 8513-8518 (2008).
Kong et al., "Microenvironmental regulation of biomacromolecular therapies," Nat. Rev. Drug Discovery, vol. 6, 455-463 (2007).
Haines-Butterick et al., "Controlling hydrogelation kinetics by peptide design for three-dimensional encapsulation and injectable delivery of cells," Proc. Natl. Acad. Sci. U.S.A., vol. 104, 7791-7796 (2007).
Cejas et al., "Collagen-Related Peptides: Self-Assembly of Short, Single Strands into a Functional Biomaterial of Micrometer Scale," J. Am. Chem. Soc., vol. 129, 2202-3 (2007).
Cai et al., "Suppression of Hepatocyte Growth Factor Production Impairs the Ability of Adipose-Derived Stem Cells to Promote Ischemic Tissue Revascularization," Stem Cells, vol. 25, 3234-3243 (2007).

(Continued)

*Primary Examiner* — Karen Cochrane Carlson
(74) *Attorney, Agent, or Firm* — Barnes & Thornburg LLP

(57) ABSTRACT

Described herein are conjugates of collagen peptides and metal binding agents and compositions resulting therefrom, useful in various tissue engineering and regeneration applications, in cell culture, cell adhesion, cosmetic surgery, construction of artificial skin substitutes, management of severe burns and burn surgery, reconstruction of bone and a wide variety of dental, orthopedic and surgical purposes, as drug delivery vehicles and in delivering populations of cells to a site of disease or injury.

24 Claims, 42 Drawing Sheets

(56) References Cited

OTHER PUBLICATIONS

Rele et al., "D-Periodic Collagen-Mimetic Microfibers," J. Am. Chem. Soc., vol. 129, 14780-14787 (2007).
Sieminski et al., "The Stiffness of Three-dimensional Ionic Self-assembling Peptide Gels Affects the Extent of Capillary-like Network Formation," Cell Biolchem. Biophys., vol. 49.2, 73-83 (2007).
Alavi et al., "Cell Survival in a Three-Dimensional Matrix," Methods in Exzymology, vol. 426, 85-101 (2007).
Ramachandran et al., "Peptide-Based Viscoelastic Matrices for Drug Delivery and Tissue Repair," Biodrugs, vol. 20, 263-69 (2006).
Kotch et al., "Self-assembly of synthetic collagen triple helices," Proc. Natl. Acad. Sci. U.S.A., vol. 103, 3028-3033 (2006).
Zimenkov et al., "Rational Design of a Reversible pH-Responsive Switch for Peptide Self-Assembly," J. Am. Chem. Soc., vol. 128, 6770-6771 (2006).
Griffith et al., "Capturing complex 3D tissue physiology in vitro," Nat. Rev. Mol. Cell Biol., vol. 7, 211-224 (2006).
Lazar et al., "Helix-Turn-Helix Peptides That Form α-Helical Fibrils: Turn Sequences Drive Fibril Structure," Biochemistry, vol. 44, 12681-12689 (2005).
Lavik et al., "Fabrication of degradable polymer scaffolds to direct the integration and differentiation of retinal progenitors," Biomaterials, vol. 26, 3187-3196 (2005).
Koide et al., "Triple Helical Collagen-Like Peptides: Engineering and Applications in Matrix Biology," Tissue Res., vol. 46, 131-41 (2005).
Horch et al., "Tissue Engineering of Cultured Skin Substitutes," J. Cell. Mol. Med., vol. 9, No. 3, 592-608 (2005).
D'Andrea et al, "Targeting angiogenesis: Structural characterization and biological properties of a de novo engineered VEGF mimicking peptide," Proc. Natl. Acad. Sci. U.S.A., vol. 102, 14215-20 (2005).
Paramonov et al., "Synthesis of Collagen-like Peptide Polymers by Native Chemical Ligation," Macromolecules, vol. 38, 7555-7561 (2005).
Brey et al., "Therapeutic Neovascularization:Contributions from Bioengineering," Tissue Eng, vol. 11, 567-84 (2005).
Zhou et al., "Helical Supramolecules and Fibers Utilizing Leucine Zipper-Displaying Dendrimers," J. Am. Chem. Soc., vol. 126, 734-735 (2004).
Oswald et al., "Mesenchymal Stem Cells Can Be Differentiated Into Endothelial Cells in Vitro," Stem Cells, vol. 22, 377-84 (2004).
Sieminski et al., "The relative magnitudes of endothelial force generation and matrix stiffness modulate capillary morphogenesis in vitro," Experimental Cell Research, vol. 297, 574-584 (2004).
Langer et al., "Designing materials for biology and medicine," vol. 428, 487-492 (2004).
Ryadnov et al., "Engineering the morphology of a self-assembling protein fibre," Nat. Mater., vol. 2, 329-332 (2003).
Ringe et al., "Stem cells for regenerative medicine: advances in the engineering of tissues and organs," Naturwissenschaften, vol. 89, 338-51 (2002).
Hartgerink et al., "Self-Assembly and Mineralization of Peptide-Amphiphile Nanofibers," Science, vol. 294, 1684-1688 (2001).
Persikov et al., "Amino Acid Propensities for the Collagen Triple-Helix," Biochemistry, vol. 39, 14960-7 (2000).
Kwak et al., "Triple Helical Stabilities of Guest-Host Collagen Mimetic Structures," Biorg. Med. Chem., vol. 7, 153-60 (1999).
Anderson et al., "Biodegradation and biocompatibility of PLA and PLGA microspheres," Adv. Drug Deliv. Rev., vol. 28, 5-24 (1997).
Sweeney et al., "Repair of critical size rat calvarial defects using extracellular matrix protein gels," J. Neurosurg, vol. 83, 710-715 (1995).
Bella et al., "Crystal and Molevular Structure of a Collagen-Like Peptide at 1.9 A Resolution," Science, vol. 266, 75-81 (1994).
Zhang et al., "Spontaneous assembly of a self-complementary oligopeptide to form a stable macroscopic membrane," Proc. Natl. Acad. Sci. U.S.A., vol. 90, 3334-3338 (1993).
Langer et al., "Tissue Engineering," Science, vol. 260, 920-926 (1993).
Peek et al., "Snythesis of redox derivatives of lysine and related peptides containing phenothiazine or tris(2,2'-bipyridine) ruthenium(II)," Int. J. Pept. Protein Res., vol. 38, 114-23 (1991).
Hubbell et al., "Endothelial Cell-Selective Materials for Tissue Engineering in the Vascular Graft via a New Receptor," Biotechnology (NY), vol. 9, 568-72 (1991).
Cowan et al., "The Polypeptide Chain Configuration of Collagen," Nature, vol. 196, 1062-4 (1955).
Supplementary European Search Report for EP 09747654, dated Aug. 9, 2012.
Xiao Mo et al: "Nanoparticle-Assisted Visualization of Binding Interactions between Collagen Mimetic Peptide and Collagen Fibers," Angewandte Chemie International Edition, vol. 45, No. 14, Mar. 27, 2006, pp. 2267-2270.
David E. Przybyla et al: "Metal-Triggered Radial Self-Assembly of Collagen Peptide Fibers," Journal of the American Chemical Society, vol. 130, No. 38, Sep. 3, 2008, pp. 12610-12611.
Marcos M. Pires et al: "Self-assembly of Collagen Peptides into Microflorettes via Metal Coordination", Journal of the American Chemical Society, vol. 131, No. 7, Feb. 25, 2009, pp. 2706-2712.
Daniel Gottlieb et al: "Self-assembled collagen-like peptide fibers as templates for metallic nanowires," Journal of Materials Chemistry, vol. 18, No. 32, Jul. 1, 2008, p. 3865.
Weibo Cai et al: "Metal-assisted Assembly and Stabilization of Collagen-like Triple Helices," Journal of the American Chemical Society, vol. 126, No. 46, Nov. 1, 2004, pp. 15030-15031.

\* cited by examiner

COLLAGEN PEPTIDE CONJUGATES AND USES THEREFOR

CROSS-REFERENCE TO RELATED APPLICATIONS

This application is a U.S. national application under 35 U.S.C. §371(b) of International Application Serial No. PCT/US2009/044093 filed May 15, 2009, which claims the benefit under 35 U.S.C. §119(e) of U.S. Provisional Patent Application Ser. No. 61/053,420, filed May 15, 2008, the disclosure of which is incorporated herein by reference.

GOVERNMENT RIGHTS

This invention was made with government support under grant number CHE0848325 awarded by the National Science Foundation. The government has certain rights in the invention.

TECHNICAL FIELD

The invention described herein pertains to conjugates of collagen peptides, and compositions resulting therefrom. In particular, the invention described herein pertains to conjugates of collagen peptides and metal binding agents and compositions resulting therefrom.

BACKGROUND AND SUMMARY OF INVENTION

Collagen is one of the most predominant components of the extracellular matrix, and is the main component of fascia, cartilage, ligaments, tendons, bone and skin. Along with soft keratin, it is responsible for skin strength and elasticity, it strengthens blood vessels and plays a role in tissue development. It is also present in crystalline form in the cornea and lens of the eye. The structural and mechanical properties of collagen arise from property of collagen peptides to form tough bundles called collagen fibers. Tropocollagen is a triple helix formed by collagen peptides, and is a subunit of larger collagen aggregates such as fibrils, which in turn form even larger aggregates such as fibers. Tropocollagen is approximately 300 nm long and 1.5 nm in diameter, and made up of three polypeptide strands, each possessing the conformation of a left-handed helix. Tropocollagen peptides each include a high content of three repeating Xaa-Yaa-Gly strands, where Pro-Hyp-Gly (Hyp=(2S,4R)-4-Hydroxyproline) is one of the more abundant repeating unit. These three left-handed helices are twisted together into a right-handed triple helix coiled coil, a quaternary structure stabilized by numerous hydrogen bonds. The tropocollagen subunits spontaneously self-assemble, with regularly staggered ends, into even larger arrays in the extracellular spaces of tissues. In the fibrillar collagens, the molecules are staggered from each other by about 67 nm, which is variable depending upon the degree of hydration. The triple-helices are also arranged in a hexagonal or quasi-hexagonal array in cross-section, in both the gap and overlap regions.

Twenty-nine types of collagen have currently been identified, though over 90% of the collagen in the body, however, are of type I, II, III, and IV, with type I being the most common. Type I collagen is found in skin, tendon, vascular, ligature, organs, and is the main component of bone; type II collagen is the main component of cartilage; type III collagen is the main component of reticular fibers, and is commonly found alongside type I; and type IV collagen forms the bases of cell basement membrane.

Though many tissues are composed primarily of type I collagen including tendon, ligament, skin, and bone, each of these structures also contains other collagen types, and also proteoglycans and glycosaminoglycans, and minerals in the case of bone. The dramatic difference in mechanical properties of each of these collagen structures has been reported to be primarily due to the molecular and macromolecular organization of collagen and the interplay of those substructures with other non-collagen type I components.

Though nearly 30 different types of natural collagen have been identified, the tertiary structures of each share the motif of the collagen triple helix. The collagen triple helix (CTH) motif is composed of three chains that each adopt a left-handed helix, which consists of 3 residues/turn (Bella et al., Science, 266:75-81 (1994); Cowan et al., Nature, 176:1062-4 (1955)). These chains come together to form a right-handed superhelix. A distinctive feature of collagen is the regular arrangement of amino acids in each of the three chains of these collagen subunits. The sequence often follows the pattern Xaa-Yaa-Gly, Gly-Pro-Xaa and/or Gly-Xaa-Hyp, where Xaa and Yaa may be any of various other amino acid residues. Proline or hydroxyproline constitute about ⅙ of the total sequence. There is some covalent crosslinking within the triple helices, and a variable amount of covalent crosslinking between tropocollagen helices forming well organized aggregates, called fibrils. Larger fibrillar bundles, or fibers, are formed from aggregates of fibrils and with the aid of and inclusion of other different classes of proteins, such as glycoproteins and proteoglycans. In addition, in certain specialized tissues like bone, the collagen triple helices lie in a parallel, staggered array with gaps of about 40 nm between the ends of the tropocollagen subunits. It has been reported that such gaps may serve as nucleation sites for the deposition of hydroxyapatite and other mineral components in long, hard, fine crystals. Type I collagen has also been reported to be largely responsible for the high tensile strength of bone.

Minimal peptide sequences based on the idealized proline-hydroxyproline-glycine (POG) sequence have been found to adopt the CTH motif (Persikov et al., Biochemistry, 39:14960-7 (2000)). Goodman and coworkers have found that six repeating units of POG are the minimum length required for triple helix formation at room temperature (Kwak et al., Bioorg Med Chem, 7:153-60 (1999)). Furthermore, increasing the number of repeating units was found to increase the triple helix stability.

Collagen has the ability to self-associate in vitro, forming gels that can act as a 3-dimensional substrate, and provide mechanical and biological signals for cell growth. Research on collagen fibrillogenesis with and without additional extracellular matrix components has been directed to a better understanding of the interrelationship between collagen and other extracellular matrix molecules in tissues. However, natural collagen matrices, such as MATRIGEL, are inherently heterogeneous materials that routinely vary in composition, thus complicating the analysis of bioassays. Furthermore, those matrices do not easily allow for the precise introduction of biomolecules, such as cell adhesion agents and growth factors. (see, e.g., Alavi et al., 426:85-101 (2007); Horch et al., J. Cell Mol. Med., 9:592-608 (2005); Ramachandran et al., Biodrugs, 20:263-69 (2006)). The use of natural collagen for tissue engineering is limited due to the difficulty in the precise control of scaffold morphology and limited ability to introduce chemical diversity.

Thus, of interest are synthetic collagen fibers that can be used not only to mimic native collagen but also to enhance its biological roles (Koide, T., Connect. Tissue Res., 46:131-41 (2005)). Self-assembling synthetic peptides have been explored as an alternative source of collagen material in an attempt to mimic and expand on the properties associated with collagen. Several self-assembling collagen mimetic peptides have been described (Paramonov et al., Macromolecules, 38:7555-7561 (2005); Kotch et al., Proc. Natl. Acad. Sci. USA, 103:3028-3033 (2006); Rele et al., J. Am. Chem. Soc., 129:14780-14787 (2007); Cejas et al., Proc. Natl. Acad. Sci. USA, 105:8513-8518 (2008); Przybyla et al., J. Am. Chem. Soc., 130:12610-12611 (2008); Pires et al., J. Am. Chem. Soc., 131:2706-2712 (2009)). To date, however, these collagen based self-assembling systems have not been exploited as 3-dimensional scaffolds for cell encapsulation and cell culture.

Another approach is to create synthetic collagen fibers that can be used to mimic native collagen and also to enhance its biological roles by generating small collagen peptides that self-assemble into collagen fibers. However, only self-assembling collagen fibers employing linear growth through incorporation of a variety of N and C-terminal functional groups has been reported. Specifically, electrostatic interactions (Koide, T., Connect. Tissue Res., 46:131-41 (2005)), π-π stacking (Koide, T., Connect. Tissue Res., 46:131-41 (2005); Cejas et al., J. Am. Chem. Soc., 129:2202-3 (2007)), a modified cysteine knot (Kotch et al., Proc. Natl. Acad. Sci. USA, 103:3028-3033 (2006)), and native chemical ligation (Paramonov et al., Macromolecules, 38:7555-7561 (2005)) have been implemented.

In addition, scaffolds composed of either non-bioactive polymers or naturally derived biopolymers have been reported (Fischbach et al., Proc. Natl. Acad. Sci. U.S.A., 106:399-404 (2009); Griffith & Swartz, Nature Rev. Mol. Cell. Biol., 7:211-224 (2006); Lavik et al., Biomaterials, 26:3187-3196 (2005)). Covalently cross linked polymers based on polyethylene oxide (PEO), poly(L-lactide) (PLLA), and poly(lactide-co-glycolic acid) (PLGA) have also been reported (Langer et al., Vacanti, Science, 260:920-926 (1993); Anderson et al., Adv. Drug. Deliv. Rev., 28:5-24 (1997); Langer et al., Nature, 428:487-492 (2004); Kong et al., Nat. Rev. Drug Discovery, 6:455-463 (2007)). Further avenues include peptide-based materials that mimic aspects of the 3-dimensional matrix of cells, such as self-assembling peptide amphiphiles (Hartgerink et al., Science, 294:1684-1688 (2001)), α-helices (Ryadnov et al., Nat. Mater., 2:329-332 (2003); Zhou et al., J. Am. Chem. Soc., 126:734-735 (2004); Lazar et al., Biochemistry, 44:12681-12689 (2005); Zimenkov et al., J. Am. Chem. Soc., 128:6770-6771 (2006); Dong et al., J. Am. Chem. Soc., 130:13691-13695 (2008)), β-sheets (Zhang et al., Proc. Natl. Acad. Sci. USA, 90:3334-3338 (1993); Haines-Butterick et al., Proc. Natl. Acad. Sci. USA, 104:7791-7796 (2007); Murasato et al., Biomacromolecules, 9:913-918 (2008)), and β-amino acid helices (Pomerantz et al, Angew. Chem. Int. Ed., 47:1241-1244 (2008); Angew. Chem., 47:1241-1244 (2008)).

While these strategies have been successful in generating collagen peptide fibers, there is still a need to control the three-dimensional architecture of collagen networks, a desirable feature for tissue engineering.

Described herein are synthetic collagen conjugates. In one aspect, the conjugates are capable of spontaneous self-assembly, or self-assembly under mild conditions, into triple helical configurations, also referred to as CTHs. It is appreciated that such triple helical configurations or CTHs are analogous to tropocollagen. In another aspect, the CTHs formed from the conjugates described herein are also capable of aggregating in the presence of metal ions to form fibrils, fibers, and/or more complex bundled structures. In another embodiment, the synthetic collagen conjugates described herein for 3-dimensional structures or aggregates with myriad morphologies, including particle morphologies, mesh morphologies, or mesh morphologies with embedded particulate regions. Illustrative particle morphologies include, spheres, nanospheres, hollow microspheres, open curved tubes, layered sheets, C-types, microdisks, nanodisks, shaped flakes, florettes, cages, meshes, anemones, microflorettes, and the like. Illustrative mesh morphologies include a wide range of porosity. Each of those aggregates may have nanometer and/or micrometer scale features. It has been discovered herein that the morphologies of the aggregates are controlled, at least in part, by the nature of the metal, the nature of the synthetic collagen conjugates, and the relative concentration of the metal.

Accordingly, described herein are synthetic collagen conjugate aggregates with ordered structures and with tunable shapes, sizes, and tertiary structure. Without being bound by theory, it is believed herein that the core elements of the aggregates should be composed of short, readily synthesized monomers that are capable of self-assembling either spontaneously or under mild conditions, and are also capable of forming larger aggregates under the influence of an external stimulus, such as in the presence of a metal ion. In addition, described herein are synthetic collagen conjugate aggregates with tunable physical properties, such as mechanical strength, tensile strength, porosity, and the like.

In another embodiment, the synthetic collagen conjugates described herein are covalent conjugates of one or more metal binding moieties and a peptide. It is understood that the any or all of the metal-binding moieties may be directly attached to the peptide, or optionally covalently attached to the peptide through a divalent linker. In one aspect, the peptide is formed from and analogous to collagen-like material. It is appreciated that such peptides may possess similar physical and biomechanical properties to natural collagen, thereby generating a scaffold that may more closely mimic the extracellular matrix (ECM). In another aspect, the conjugate includes one or more metal-binding moieties, and a peptide comprising tripeptides of glycine, tripeptides of glycine and proline, tripeptides of glycine and hydroxyproline, and tripeptides of glycine, proline and hydroxyproline. In another aspect, the one or more metal-binding moieties are covalently attached to the peptide. In another aspect, the synthetic collagen conjugates described herein are capable of forming type II helix. Without being bound by theory, it is believed herein that three-dimensional, collagen-peptide assemblies could be obtained by the appropriate positioning of metal-binding ligands within collagen triple helices, with the underlying design criteria being to incorporate metal binding sites into small collagen peptides and use metal-ligand interactions to drive aggregation. It is appreciated however that the modified peptides should be able self assemble or assemble under mild conditions into triple helices.

Several non-limiting illustrative designs are described herein (see, FIG. 1, illustrated with a polyPOG peptide core). In one embodiment, one or more metal binding moieties are incorporated at both of the termini of one or more of the peptides forming the CTH (FIG. 1A, linear aggregation). In one variation, one or more metal binding moieties are incorporated within the interior of the one or more of the peptides forming the CTH (FIG. 1A, radial aggregation). In another variation, one or more metal binding moieties are incorporated within the interior, and at either one of or, alternatively, at both of the termini of one or more of the peptides forming the CTH (FIG. 1A, crosslinked aggregation). In another embodiment synthetic collagen conjugates are described that are capable of aggregating in a linear manner. In another embodiment synthetic collagen conjugates are described that are capable of aggregating in a radial manner. In another embodiment synthetic collagen conjugates are described that are capable of aggregating in both a linear and a radial manner, resulting in a cross-linked aggregate.

Also described herein are uses for synthetic collagen conjugates in 3-dimensional cell culture, for cell adhesion, in tissue engineering and regeneration, in cosmetic surgery, in the construction of artificial skin substitutes, in the management of severe burns and burns surgery, in reconstruction of bone and in a wide variety of dental, orthopedic and surgical purposes. Also described herein are uses for synthetic collagen conjugates as drug delivery vehicles. Also described herein are uses for synthetic collagen conjugates for delivering populations of cells to a site of disease or injury. Also described herein are methods for treating diseases and/or injuries that include administration of the compounds and compositions, and/or the resulting aggregated prepared therefrom, described herein to a patient in need of relief from the disease or injury. In one embodiment, the methods are used for directing cell adhesiveness. In another embodiment, methods are used to deliver populations of cells. It is understood that the aggregates described herein are advantageously compatible with living cells.

In another embodiment, the aggregates described herein are reversible and may be converted back to smaller subunits such as triple helical structures. It is appreciated that such reversibility may be advantageous to allow for the release of drugs and/or cells from the interior of the aggregate structure after administration. It is further appreciated that such a reversible property is precluded in most covalently cross-linked polymers.

In another embodiment, synthetic collagen conjugate aggregates are described herein where one or more un-coordinated, uncomplexed, or unbound metal binding moiety is used to deliver a drug. The unbound metal binding moiety may be used for binding and temporal release of biologically relevant molecules, such as growth factors, associated with the unbound metal binding moiety. It is understood that the unbound metal binding moiety may be on the surface or in the interior of the aggregate.

As used herein, associated refers to molecules that are covalently attached, complexed, ionically bonded, attached via a conjugate such as avidin-streptavidin, biotin-streptavidin, and the like.

In another embodiment, synthetic collagen conjugate aggregates are described herein and used to stabilize and/or deliver a cell or population of cells. In another embodiment, synthetic collagen conjugate aggregates are described herein where one or more un-coordinated, uncomplexed, or unbound metal binding moiety is used to stabilize and/or deliver a cell or population of cells. The unbound metal binding moiety may be used for binding and temporal release of a cell using a cell adhesion agent or peptide associated with the unbound metal binding moiety. In yet another embodiment, it was envisioned that collagen peptide biomaterials may be used as delivery vehicles for in vivo cell-based therapies with regenerative applications. It is understood that the unbound metal binding moiety may be on the surface or in the interior of the aggregate. In each of the embodiments described herein, cells may be a population of exogenously grown cells.

In another embodiment, synthetic collagen conjugate aggregates are described herein where one or more un-coordinated, uncomplexed, or unbound metal binding moiety is used as a scaffold and/or vehicle for stem cell differentiation and cell growth into tissue. The unbound metal binding moiety may be used for binding and temporal release of a cell using a cell adhesion agent or peptide associated with the unbound metal binding moiety. It is understood that the unbound metal binding moiety may be on the surface or in the interior of the aggregate. Without being bound by theory, it is believed herein that the physical properties of synthetic collagen peptide aggregates play a role in cell growth and differentiation, and that these properties may be modified in a predetermined way as described herein.

In another embodiment, methods are described for promoting tissue regeneration using synthetic collagen conjugate aggregates. In another embodiment, methods are described for promoting the growth and differentiation of stem cells, including adult stem cell, using synthetic collagen conjugate aggregates. In another embodiment, methods are described for promoting the growth of blood vessels using synthetic collagen conjugate aggregates. In one aspect, the methods comprise the step of administering one or more synthetic collagens, either alone or in combination with other components to the patient, where the one or more synthetic collagens promote healing, tissue regeneration, or prevent injury of the tissue in the patient. The methods and compositions described herein can be used to treat any condition where the tissue is damaged, including damaged connective tissue, such as cartilage, muscle tissue, and bone tissue.

DETAILED DESCRIPTION

Figure 1:
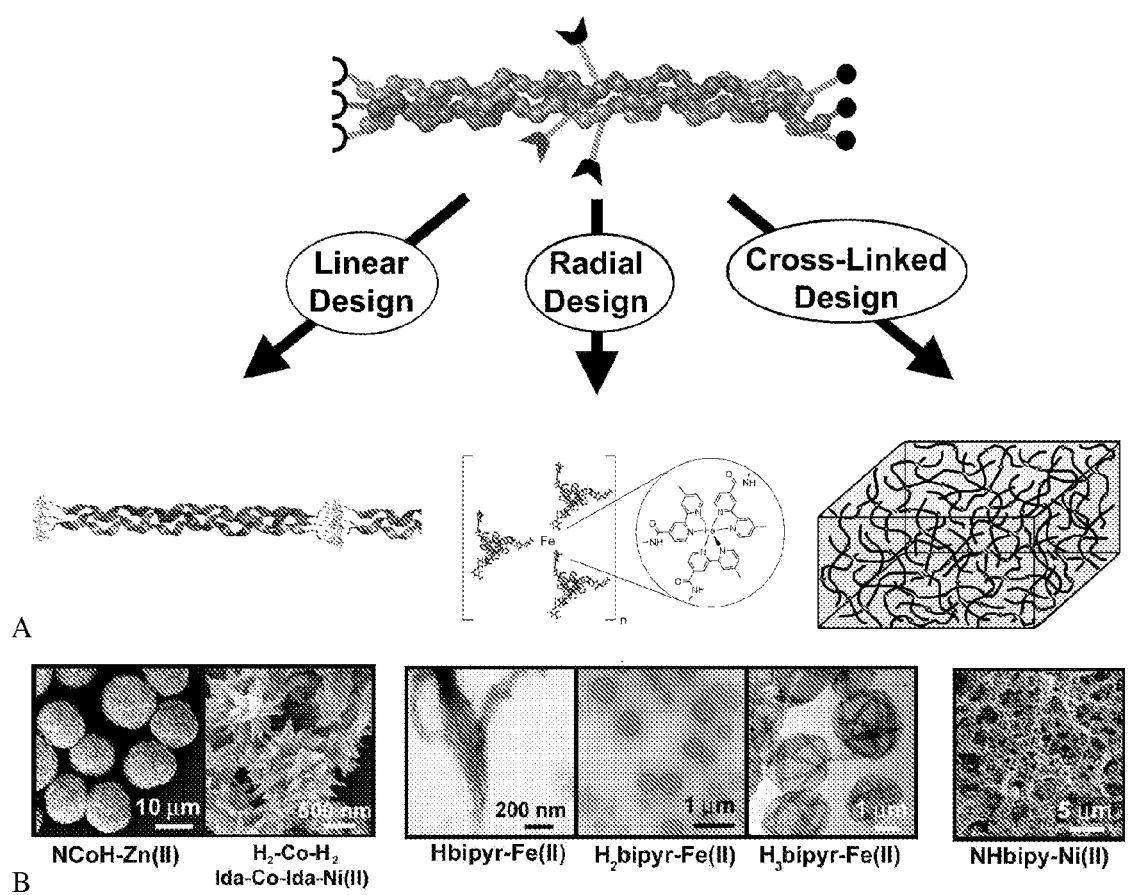
FIG. 1. (A) Overall strategies for self-assembling collagen triple helical peptides using metal-ligand interactions through linear, radial and crosslinked growth mechanisms; (B) SEM images of the structures formed from NCoH, Ida-Co-Ida/$H_2$—Co—$H_2$ and NHbipy, TEM images of the structures formed from H-byp, H-byp$_2$, and AFM image of the structures formed with H-byp$_2$ all with the added metal ions shown. Incorporation of two, H-(byp)$_2$, or three, H-(byp)$_3$, bipyridyl-groups into the radial design led to the formation of nano-scale disks and micro-scale hollow spheres.

In one illustrative embodiment of the invention, a synthetic collagen conjugate capable of forming a type II helix, such as a polyproline or proline rich type II helix, is described. The conjugate is formed from one or more metal-binding moieties, and a peptide. In one aspect, the peptide includes a plurality of glycine residues, a plurality of proline residues, and/or a plurality of hydroxyproline residues. In another aspect, the one or more metal-binding moieties are covalently attached to the peptide. In another aspect, the covalent attachment of each metal-binding moiety may be direct or optionally through a divalent linker. In one variation, the peptide includes a plurality of tripeptides of glycine and praline, a plurality of tripeptides of glycine and hydroxyproline, and/or a plurality of tripeptides of glycine, proline and hydroxyproline.

In another embodiment, synthetic collagen conjugates are described herein where at least one of the metal-binding moieties is covalently attached to a non-terminal amino acid of the peptide. In one variation, at least one of the metal-binding moieties is covalently attached to the N-terminus of the peptide, and at least one of the metal-binding moieties is covalently attached to the C-terminus of the peptide. In another variation, at least one of the metal-binding moieties is covalently attached to a non-terminal amino acid of the peptide, at least one of the metal-binding moieties is covalently attached to the N-terminus of the peptide, and at least one of the metal-binding moieties is covalently attached to the C-terminus of the peptide.

In another embodiment, synthetic collagen conjugate of the formula

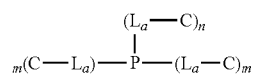

and pharmaceutically acceptable salts, hydrates, and solvates thereof are described. P illustratively is a trivalent peptide or peptide amide comprising plurality of tripeptides of glycine; each L is an independently selected linker; each C is independently selected in each instance from the consisting of hydrogen, pharmaceutically acceptable cations, metal-binding moieties, and protecting groups; a is an integer, independently selected in each instance from the group consisting of 0 and 1; m is an integer, independently selected in each instance from the group consisting of 0 and 1; and n is an integer from 0 to about 5; providing that at least one of m or n is not 0. In one variation, the peptide includes a plurality of glycine residues, a plurality of proline residues, and/or a plurality of hydroxyproline residues. In another variation, the peptide includes a plurality of tripeptides of glycine and praline, a plurality of tripeptides of glycine and hydroxyproline, and/or a plurality of tripeptides of glycine, proline and hydroxyproline.

In another embodiment, n is 1. In another embodiment, m is 1. In another embodiment, m is 1 and n is 1. In another embodiment of each of the synthetic collagen conjugates described herein, the peptide is at least 18 amino acids in length, or between 18 and 54 amino acids in length.

In another embodiment of each of the synthetic collagen conjugates described herein, the conjugate is self assembling, and capable of forming a triple helix. In another embodiment of each of the synthetic collagen conjugates described herein, the triple helix is capable of aggregating in the presence of a transition metal.

In another embodiment of each of the synthetic collagen conjugates described herein, the peptide comprises at least about 25%, at least about 30%, or about 33% glycine. In another embodiment of each of the synthetic collagen conjugates described herein, the peptide comprises at least about 5% or about 8% or about 9% proline. In another embodiment of each of the synthetic collagen conjugates described herein, the peptide comprises a nonapeptide, and octadecapeptide, or two nonapeptides where every third amino acid is glycine. In another embodiment of each of the synthetic collagen conjugates described herein, the peptide comprises a plurality of divalent tripeptides selected from Xaa-Yaa-Gly, Gly-Pro-Xaa and/or Gly-Xaa-Hyp, or a combination thereof, where each Xaa and Yaa is independently selected in each instance from the group consisting of naturally occurring amino acids and derivatives of naturally occurring amino acids, such as hydroxylysine.

In another embodiment of each of the synthetic collagen conjugates described herein, the metal-binding moieties is selected from bipyridinyls, amino bis(acetic acid)s, $His_x$, where x is an integer from 2 to 4, such as $His_2$, $His_3$, or an amide thereof, or a pharmaceutically acceptable salt thereof. Illustratively, the amino bis(acetic acid) is Asp-N,N-bis acetic acid, Glu-N,N-bis acetic acid, Orn-N,N-bis acetic acid, or Lys-N,N-bis acetic acid, or a pharmaceutically acceptable salt or the foregoing.

In another embodiment of each of the synthetic collagen conjugates described herein, the conjugate also includes a drug, where the drug is associated with the conjugate, such as being covalently attached to the peptide, optionally through a divalent linker. Illustratively, the drug is a cell adhesion agent, a growth factor, an integrin binding domain peptide, or an RGD peptide or RGD-like peptide, such as an REDV peptide, an RGD peptide or a YIGSR peptide. Illustrative growth factors include but are not limited to vascular endothelial growth factor (VEGF), transforming growth factor (TGF-beta), bone morphogenetic protein 2 (BMP-2), epidermal growth factor (EGF), fibroblast growth factor (FGF), or hepatocyte growth factor (HGF), or a pharmaceutically effective fragment thereof.

Also described herein are conjugates useful for treating bone or cartilage diseases or defects. Illustrative drugs include bone antiresorptive agents, such as bisphosphonates, sodium alendronate, risedronate, ibandronate, and the like, selective estrogen receptor modulators (SERMs), such as raloxifene, peptide hormones, such as parathyroid hormone (PTH), or a fragment thereof such as PTH (1-34), and others.

Also described herein are conjugates useful as diagnostic or imaging agents, where a diagnostic or imaging agent is associated with, such as being covalently attached to, the peptide, optionally through a divalent linker. Illustrative imaging agents include NBD fluorophore, and the like.

Also described herein are conjugates useful for delivering cells or populations of cells. Illustrative population of cells include but are not limited to adipose derived stem cells (ASC), human umbilical vein endothelial cells (HUVEC, commercially available from ATCC), mesenchymal stem cells (MSC, commercially available from Cambrex), and the like, and combinations thereof.

It is to be understood that each of the embodiments described herein may be used in combination. For example, aggregates of conjugates described herein may be used to deliver both cells and drugs, such as a combination of an osteoblast progenitor cell population and the corresponding growth and/or differentiating factor.

As used herein, the term metal-binding moiety generally refers to a polydentate compound or compound fragment that includes organic functional groups that are capable of binding to, complexing with, or coordinating to a transition metal. Illustrative metal-binding moieties include bipyridyl groups, polyacids, polyhistidine, and the like. The groups may be directly attached to the peptide or may be attached via a divalent linker as described herein. Illustrative metal binding moieties include chelating agents, such as but not limited to polyamines, such as ethylenediamine, 1,4,7,10-tetraazacyclododecane-N,N',N'',N'''-tetraacetic acid (DOTA), 1,4,7-tris (carboxymethyl)10-(aminoethyl)-1,4,7,10-tetraazacyclododecane (DO3A-EA), and variations DO3A, APA-DO3A, polyoximes and polyimines, such as iminodiacetate (IDA), and the like, polyheteroaromatic compounds, such as pyridine, bipyridyl groups, terpyridine, and the like, polythiols, such as DOTA, cysteinamine, and the like, polyacids, such as amino bis(acetic acid)s, EDTA, and the like, dipeptides, such as bishistidine, ethylene dicytsteine, bis(beta-aminoalanine), and the like, tripeptides, such as trishistidine, and the like.

In another embodiment, one or more of the one or more metal-binding moieties are covalently attached to the peptide with a divalent linker. Such divalent linkers may be independently selected in each instance and include one or more divalent fragments selected independently in each instance from the group consisting of alkylene, heteroalkylene, cycloalkylene, cycloheteroalkylene, arylene, and heteroarylene each of which is optionally substituted. As used herein, the terms heteroalkylene and cycloheteroalkylene include the corresponding alkylene or cycloalkylene where one or more carbon atoms in any of the linear, branched, or cyclic portions of the divalent fragment are replaced by a heteroatom, each of which may be optionally substituted. Illustrative heteroatoms include oxygen, nitrogen, phosphorus, sulfur, and the like.

In each of the embodiments described herein, additional components may be optionally admixed or co-administered with the one or more synthetic collagens. Illustratively, the compounds described herein may be administered in combination with one or more other matrix forming materials, including but not limited to other naturally occurring or synthetic collagens, such as those described herein, and the like.

Illustratively, the compounds described herein may be administered in combination with one or more other components, including but not limited to, such as hydroxyapatite, hyaluronan, collagen, and the like Illustratively, the compounds described herein may be administered in combination with one or more an exogenous populations of cells, such as but not limited to adipose derived stem cells, human umbilical vein endothelial cells, mesenchymal stem cells, osteoblasts, chondrocytes, and the like.

The compounds and compositions described herein may be administered in a variety of dosage forms, such as any dosage form adapted for topical administration, including but not limited to powders, gels, creams, pastes, ointments, plasters, lotions, topical liquids, transdermal patches, and the like.

The compounds and compositions described herein may be administered in a flowable formulation that may be introduced, such as by injection, into a defect or cavity, such as a bone defect, periodontal defect, and the like. In such flowable formulations, the compositions may also include other components, such as poloxamers, including poloxamers that are liquids at ambient temperatures, and exhibit more gel-like characteristics at the body temperature of the patient.

In another embodiment, the synthetic collagen conjugates described herein are prepared by the methods described herein, or alternatively are prepared at least in part using known peptide syntheses, such as but not limited to solid phase peptide synthesis.

In another illustrative embodiment, the peptide is (Pro-Hyp-Gly)$_9$. It is appreciated that this illustrative peptide sequence readily self assembles, and forms a triple helix with high thermal stability.

In another embodiment, both the C terminus and the N terminus of a peptide include a metal binding moiety. In one aspect, one terminus of the peptide is covalently attached to L-N(CH$_2$CO$_2$H)$_2$, or a salt thereof where L is a linker. In another aspect, one terminus of the peptide is covalently attached to His-His-NH$_2$. In another aspect, one terminus is covalently attached to His-His-NH$_2$, and the other terminus is covalently attached to Ac-Hi-His. In another aspect, one terminus is covalently attached to Ac-Pro-Lys(N—(CH$_2$CO$_2$H)$_2$), or a salt thereof. In another aspect, one terminus is covalently attached to Lys(N—(CH$_2$CO$_2$H)$_2$)-Gly-Nh$_2$, or a salt thereof.

In one illustrative example, L-N(CH$_2$CO$_2$H)$_2$ corresponds to a nitrilotriacetic acid (NTA) unit, for example, compound NCoH. Upon formation of the triple helix, a clustering of six histidines at one end of the triple helix and three NTAs at the other end results.

In another embodiment, a non-terminal residue of the peptide is covalently attached to L-bipyridinyl, or a salt thereof where L is a linker. In another embodiment, two non-terminal residues of the peptide are covalently attached to L-bipyridinyl, or a salt thereof where L is a linker. In another embodiment, three or at least three non-terminal residues of the peptide are covalently attached to L-bipyridinyl, or a salt thereof where L is a linker.

In another embodiment, a non-terminal residue of the peptide is covalently attached to L-bipyridinyl, or a salt thereof where L is a linker; and each terminal residue is covalently attached to metal binding moiety selected from L-N(CH$_2$CO$_2$H)$_2$, His-His-NH$_2$. Ac-Pro-Lys(N—(CH$_2$CO$_2$H)$_2$), Lys(N—(CH$_2$CO$_2$H)$_2$)-Gly-Nh$_2$, or a salt of the foregoing.

Introduction of a transition metal in each of the foregoing embodiments results in directional aggregation of individual triple helices into a bundle that grows in both length and girth. In one embodiment, a process for aggregating synthetic collagen conjugate triple helices is described. The process includes the step of treating a solution of the synthetic collagen conjugate triple helix with a transition metal salt. The solution is illustratively at a concentration in the range from about 10 µM to about 10 mM, or about 100 µM to about 5 mM, or at a concentration greater than about 100 µM. The process is illustrative performed at near neutral pH, such as at a pH in the range from about 6 to about 8, from about 7 to about 8, from about 6.5 to about 7.5, from about 6.8 to about 7.2, from about 7 to about 7.5, or from about 7 to about 7.2. The process may be buffered using any suitable buffer for the desired pH, such as MOPS. The process is illustratively performed below the melting temperature of the triple helical form of the synthetic collagen conjugate, such as below about 50° C., below about 40° C., below about 30° C., below about 25° C., or at about ambient temperature. The process may be performed at lower temperature, but it is to be appreciated that the reaction times are much longer.

In another embodiment, the metal is a transition metal, including but not limited to nickel, cobalt, copper, zinc, ruthenium, and the like. The transition metal may be used in one or more oxidation states, such as Ni(II), Co(II), Cu(II) and Zn(II), Ru(II), and the like. In another embodiment, the ratio of metal ion to compound is in the range from about 0.1:1 to about 5:1, from about 0.1:1 to about 2:1, or from about 0.2:1 to 1:1. It is understood that the nature of metal and/or the ratio of metal ion to compound may affect the morphology, the mechanical properties, and like properties of the resulting synthetic collagen. In one aspect, the stiffness of the synthetic collagen is altered by the nature of metal and/or the ratio of metal ion to compound.

Figure 2:
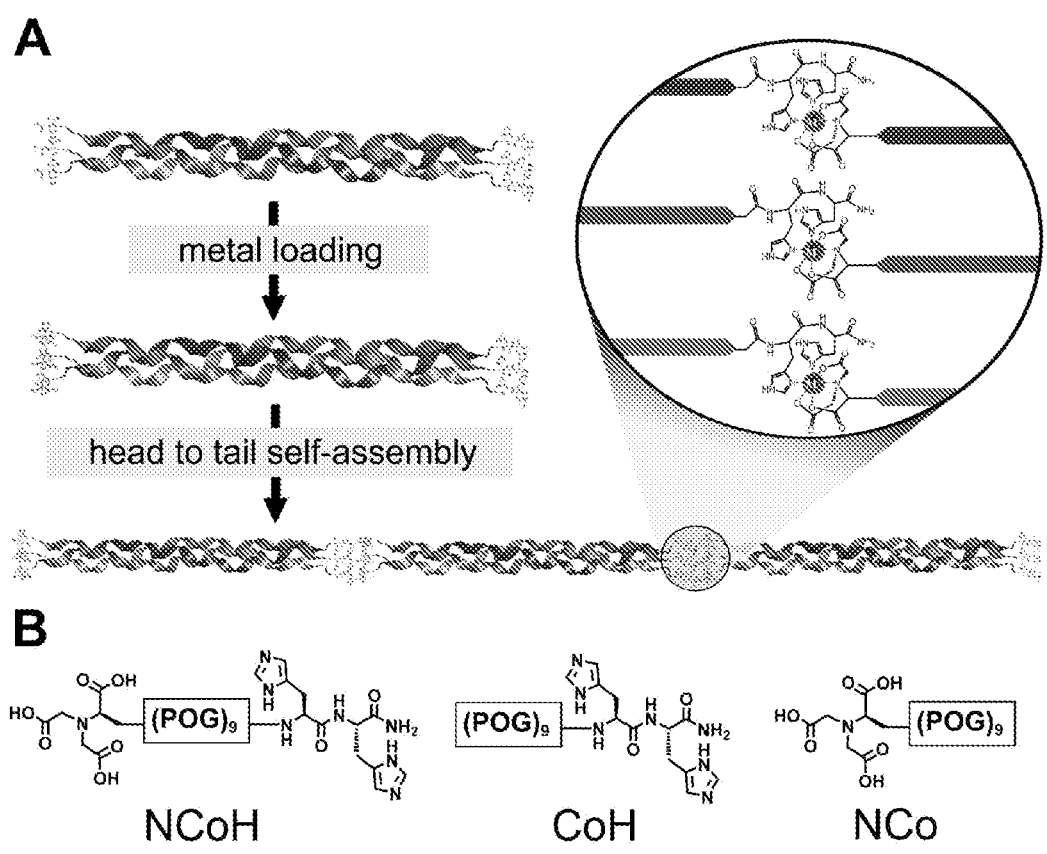
FIG. 2. (A) Schematic representation of the design of the NCoH peptide and one possible means for aggregation; following the triple helix formation, the addition of metal ions would trigger an initial aggregate directed by the NTA and His2 moieties; (B) Structures of peptides NCoH, CoH, and NCo.

In another embodiment, synthetic collagen conjugates having a central collagen-based core composed, illustratively, of nine repeating units of the tripeptide Pro-Hyp-Gly and two different metal binding moieties at each terminus. In one example, NCoH (FIG. 2) is described having a nitrilotriacetic acid (NTA) unit at the N-terminus and a His$_2$ unit at the C-terminus. Triple helix formation of the individual NCoH strands results in clustering of six histidines at one end of the triple helix and three NTA's at the alternate ends. For this design, this asymmetry of the metal ligands at the different termini was included to maintain a continuous register of Pro-Hyp-Gly across the growing aggregate (FIG. 2A). It is understood that head-to-head, tail-to-tail, and/or head-to-tail aggregation is possible. The introduction of the appropriate transition metal may result in directional aggregation of individual triple helices. Two control peptides were also prepared containing either an N-terminal NTA (NCo) or a C-terminal His$_2$ (CoH).

Figure 3:
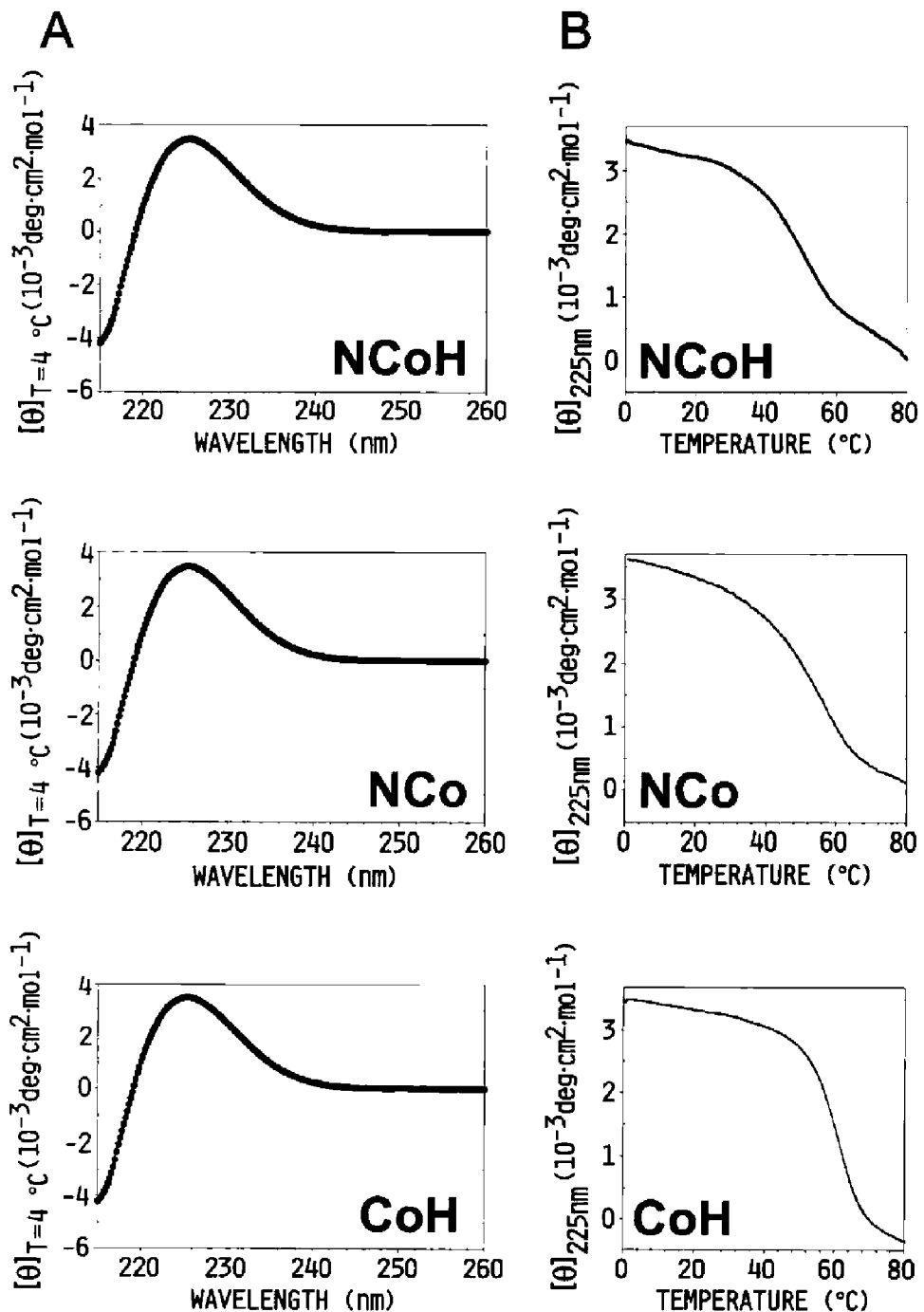
FIG. 3. Circular dichroism spectroscopy analysis of NCoH, NCo, and CoH; (A) CD spectroscopy of the specified peptides (500 μM) were measured at 4° C. in 20 mM MOPS buffer, pH 7.4; (B) Thermal denaturation of the specified peptide triple helices was monitored at 225 nm between 0 and 80° C.

Circular dichroism (CD) is used to verify that end modifications did not preclude NCoH from forming the expected collagen triple helix and to determine its thermal stability. CD spectrum of NCoH displayed a maximum molar ellipticity at 225 nm that is indicative of the polyproline type II (PPII) helical structure of collagen-like peptides (FIG. 3). Cooperative triple helix unfolding was observed for NCoH with a melting temperature (Tm) of approximately 50° C. It is possible that the decrease in stability of the triple helix of NCoH as compared to the analogous peptide (Pro-Hyp-Gly)$_9$ (Tm~67° C.) is likely a result of electrostatic repulsion at neutral pH due to the NTA termini. Both control peptides (NCo and CoH) also exhibited a PPII CD profile at 4° C. and each displayed somewhat higher melting temperatures than NCoH (58 and 61° C., respectively). Without being bound by theory, the homotrimerization of individual strands of collagen-like peptides into triple helices may enhance the proper positioning of groups the metal binding ligands at each separate terminus and, therefore, may allow the propagation of NTA/histidine association between adjoining triple helices.

Figure 4:
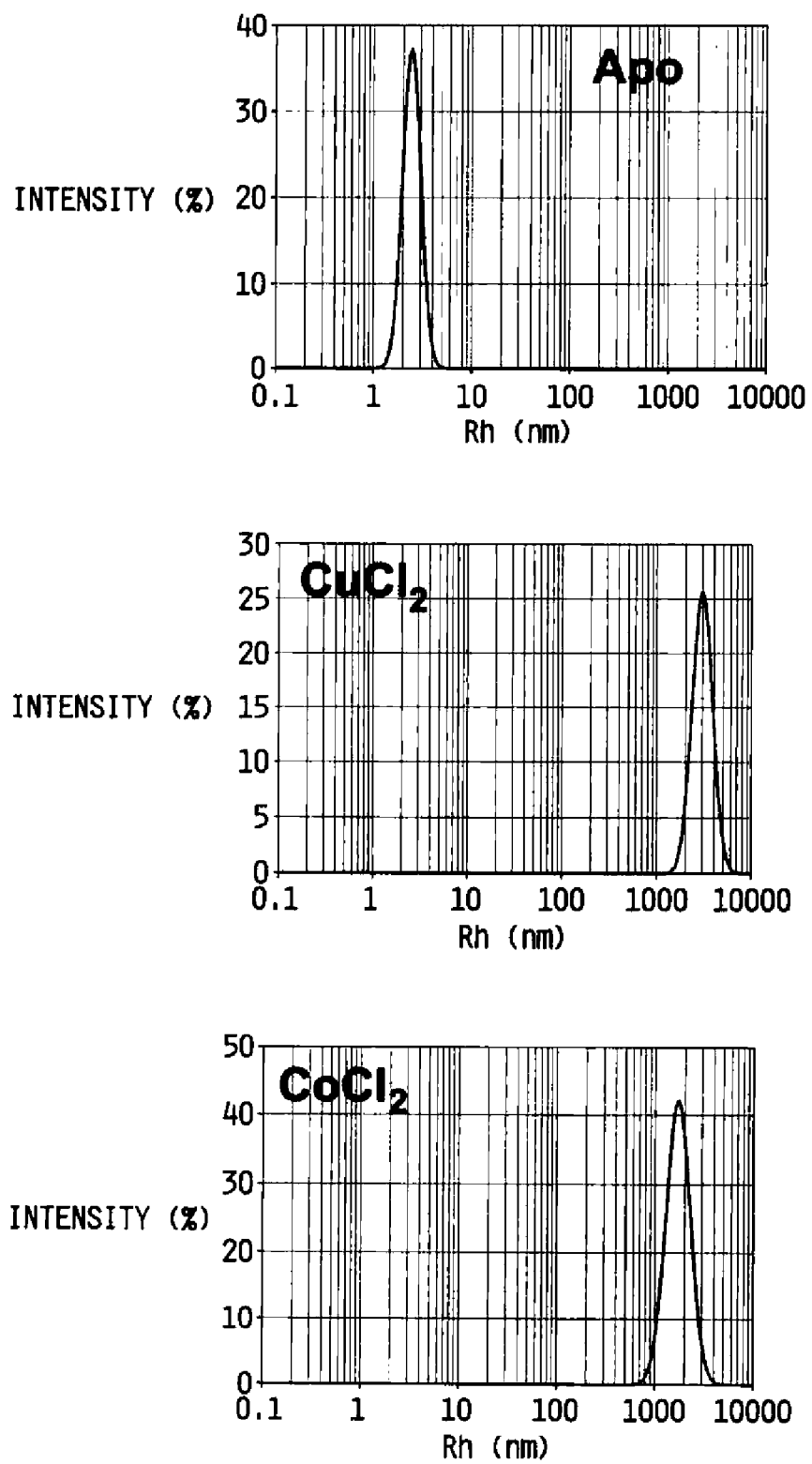
FIG. 4. Dynamic light scattering analysis of a metal screen using the NCoH peptide. Hydrodynamic radius measurements were obtained using 200 μM of peptide with 100 μM of specified metal ion in 20 mM MOPS (pH 7.4).
Figure 4:
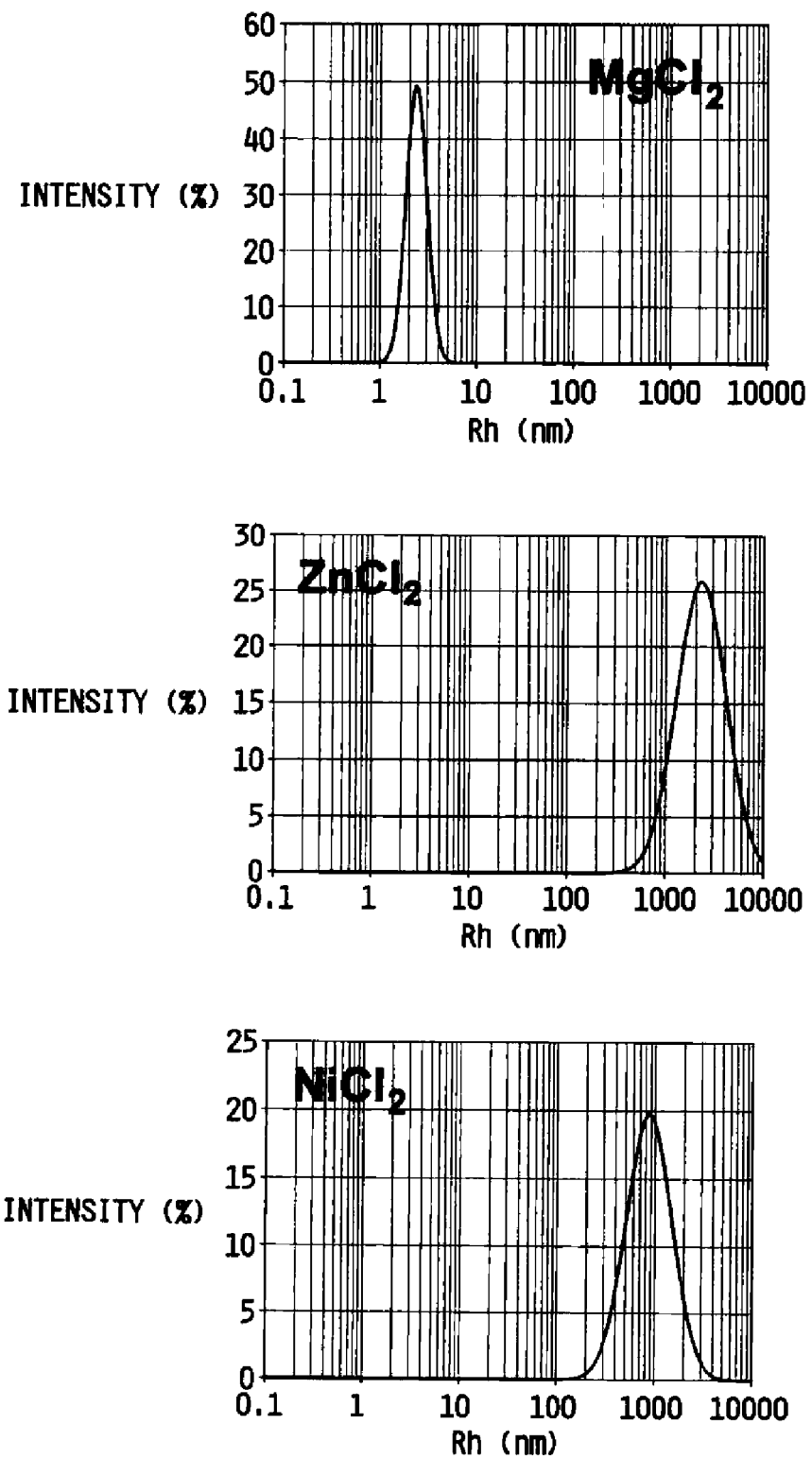

In another embodiment, a relationship between the aggregate capability and the degree of covalent attachment of metal binding moieties is described. In one example, the effect of different transition metal ions on buffered solutions of NCoH is described. Significant turbidity was observed within the solutions following the addition of metal ions such as Zn(II), Co(II), Ni(II), and Cu(II), but not with Mg(II). Dynamic light scattering (DLS) experiments were used to probe the size of the aggregates in solution. DLS revealed that addition of Zn(II), Co(II), Ni(II), and Cu(II) to NCoH each generated particles in solution with a hydrodynamic radius that was greater than 1 µm, whereas addition of Mg(II) to NCoH provided a hydrodynamic radius that was similar to that observed for the apo-peptide (FIG. 4). The two control peptides, NCo and CoH, showed no evidence of aggregate formation by DLS with Cu(II). Without being bound by theory, this observation may indicate that triple helices containing either NTA units or His residues at a single termini are not sufficient for the formation of aggregates in solution.

Figure 5:
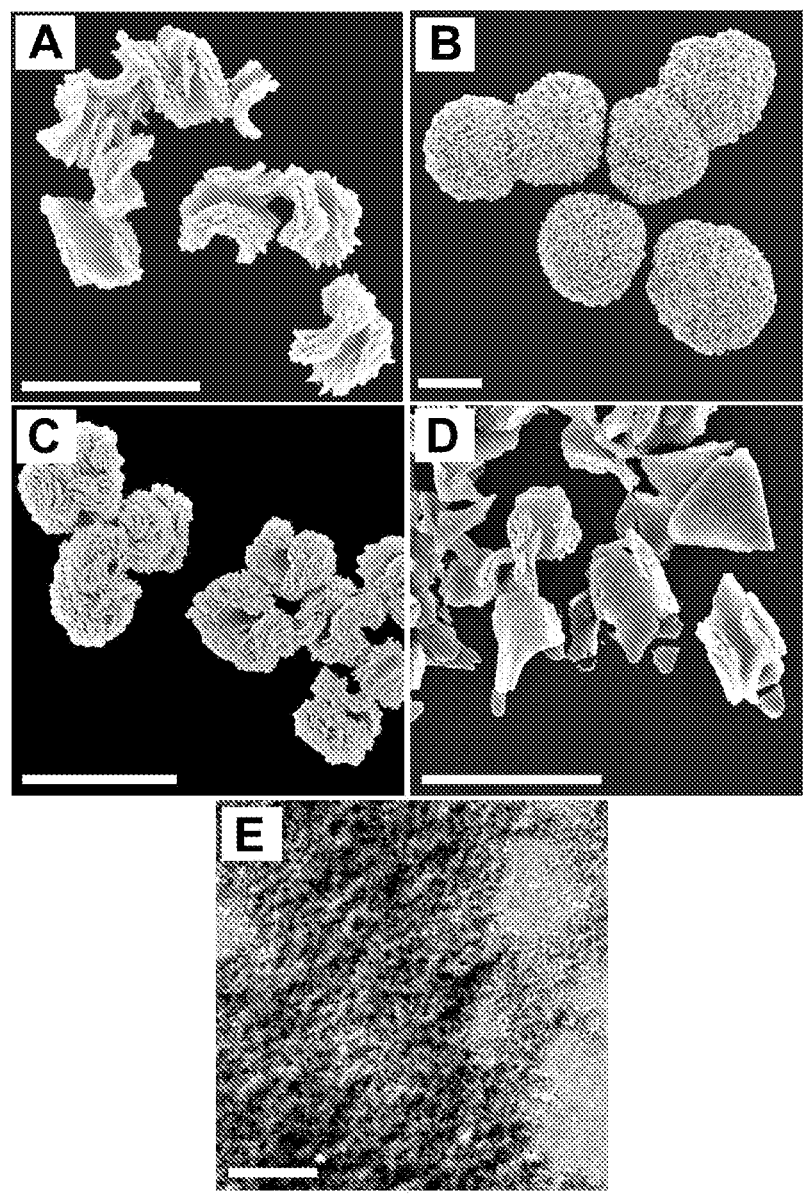
FIG. 5. Effect of metal ion concentration on particle morphology. Scanning electron microscopy images of NCoH peptide (1 mM) with varying concentrations of $ZnCl_2$: (A) 200 μM $ZnCl_2$; (B) 400 μM $ZnCl_2$; (C) 600 μM $ZnCl_2$; (D) 800 μM $ZnCl_2$; (E) 1 mM $ZnCl_2$. Scale bar=5 μm.

In another embodiment, a relationship between the aggregate morphology and the molar ratio of the metal is described. Illustratively, NCoH was incubated with various ratios of ZnCl$_2$ (FIG. 5). Scanning electron microscopy (SEM) analysis revealed that the structural morphology was dependent on the amount of metal ions in solution. For instance, when 0.4 equiv of ZnCl$_2$ was added to NCoH, micrometer-sized spherical particles were observed that resembled florettes (FIG. 5B). When the ZnCl$_2$ ratio was halved from this amount (to 0.2 equiv), the formation of open curved tubes was observed, composed of what appears to be layered sheets (FIG. 5A). Structures formed from increased ratios of ZnCl$_2$ to peptide (0.6 and 0.8 equiv) also deviated from spheres, with the former displaying "C-type" structures (FIG. 5C) and the latter showing irregularly shaped flakes (FIG. 5D). The addition of an equimolar amount of metal ions as compared to that of NCoH resulted in much smaller and finer structures (FIG. 5E).

Figure 6:
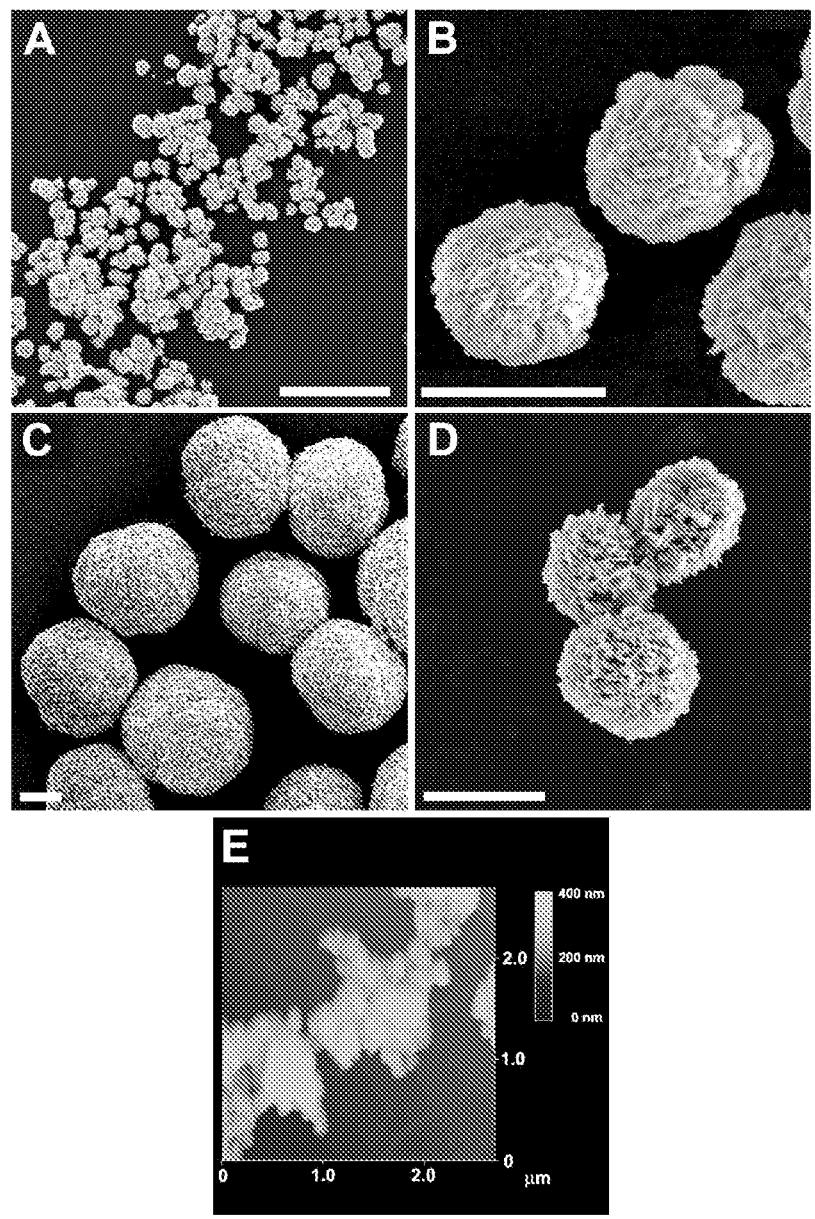
FIG. 6. SEM images of NCoH peptide (1 mM) with 400 μM $CuCl_2$ (A, scale bar=100 μm; B, scale bar=5 μm), 400 μM $ZnCl_2$ (C, scale bar=5 μm), and 400 μM $CoCl_2$ (D, scale bar=5 μm). (E) AFM image of NCoH peptide (1 mM) with 400 μM $NiCl_2$.

In another embodiment, a relationship between the aggregate morphology and the nature of the metal is described. Illustratively, SEM images of solutions composed of NCoH (1 mM) and ZnCl$_2$ (400 µM) confirmed that the aggregates that formed in solution were spherical in nature (FIG. 6C). Similarly, SEM images of solutions composed of NCoH (1 mM) and CuCl$_2$ (400 µM) confirmed that the aggregates that formed in solution were also spherical in nature (FIG. 6A). Closer examination by SEM demonstrated that these particles were also not smooth, but resembled micrometer-sized florettes (FIG. 6B). Treatment of NCoH with CoCl$_2$ (400 µM) followed by SEM imaging (FIG. 6D) also demonstrated the formation of microflorettes. Although the overall shape of these structures was similar, there were reproducible variations in size with the different metal ions. For instance, Zn(II) ions generated the largest florettes, with many reaching 10-15 µm in diameter. In one embodiment, NCoH assembled in the presence of NiCl$_2$ resulted in a completely different aggregate morphology. Imaging by atomic force microscopy (AFM) showed that the assembled structures were much smaller than those found with other metal ions (FIG. 6E). Examination of the AFM image revealed that the material is composed of interconnected and irregularly shaped nano sized spheres (50-250 nm).

Figure 7:
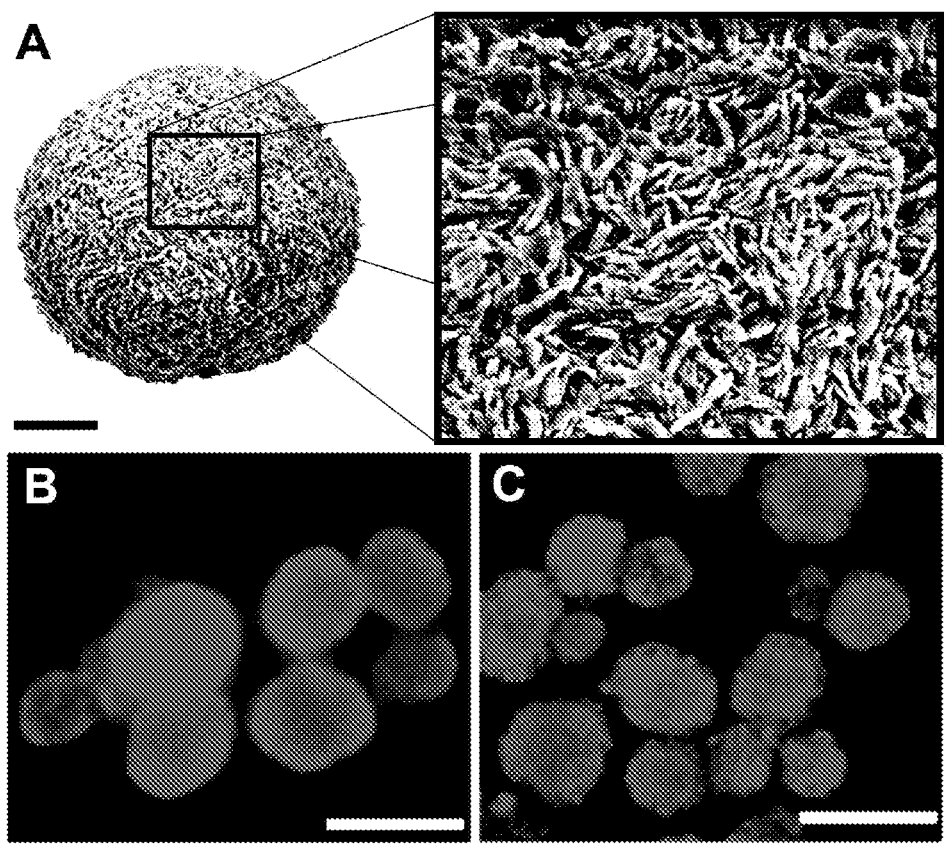
FIG. 7. (A) SEM image of the surface of the Zn(II)-based microflorettes (scale bar=5 μm) prepared from NCoH (1 mM) and ZnCl$_2$ (400 μM). Imaging of Zn(II)-based microflorettes treated with Congo red by (B) fluorescence microscopy (scale bar=20 μm) and (C) confocal microscopy (scale bar=20 μm).

Higher resolution images of the Zn(II)-based particles were obtained (FIG. 7A). Illustratively, a densely packed arrangement of individual, ruffled segments on the exterior of the particles was observed with a thickness of the surface-exposed segments of approximately 150 nm. Without being bound by theory, it is believed herein possible that the ruffled surface of the particles may endow particularly advantageous physical and biophysical properties to these particles, probably due to the extended surface area generated by the observed protrusions.

In another embodiment, synthetic collagen conjugates with associated diagnostic agents are described herein. To probe the nature of the interior of the particles, Zn(II)-based microflorettes were treated with the fluorescent collagen-binding dye Congo red. Fluorescence microscopy confirmed that Congo red became associated with the particles (FIG. 7B). Confocal microscopy was used to image the interior of the particles and demonstrated that the microflorettes were stained throughout with Congo red (FIG. 7C), confirming the presence of collagen-like material throughout the interior of the microflorettes.

Figure 8:
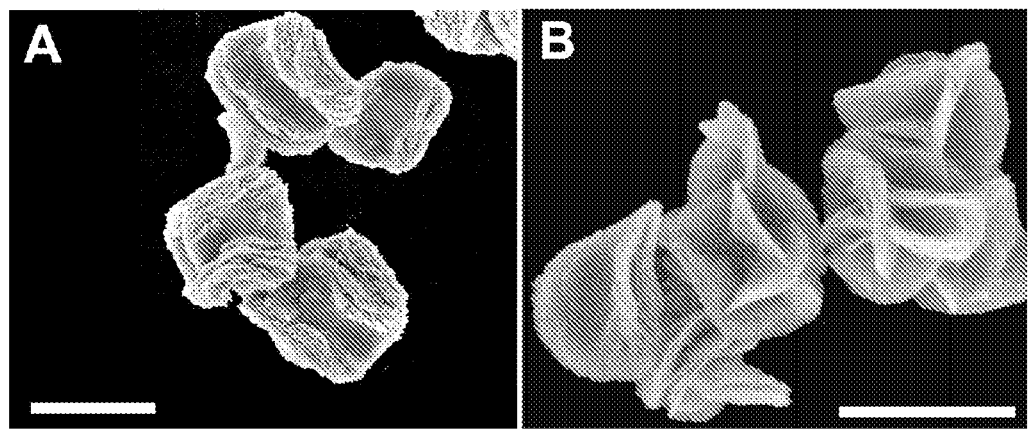
FIG. 8. SEM imaging of the NCoH peptide (1 mM) at 4° C. with (A) 400 μM ZnCl$_2$ (scale bar=5 μm) and (B) 400 μM CuCl$_2$ (scale bar=5 μm).

In another embodiment, a relationship between aggregate formation and temperatures is described. The Zn(II)-promoted aggregation experiment is described herein, using the same conditions that had previously produced microflorettes, except at 4° C. to slow down the formation of the structures. The particles that were generated after 24 h were visualized by SEM (FIG. 8A). Interestingly curved layered sheets were observed with a sheet thickness of approximately 60 nm. The addition of Cu(II) to NCoH at 4° C. was also monitored after 24 h, and layered sheet like structures of about the same thickness were also observed (FIG. 8B). Without being bound by theory, it is possible that these structures constitute folding intermediates for the microflorettes and that sheet formation plays a significant role.

Figure 9:
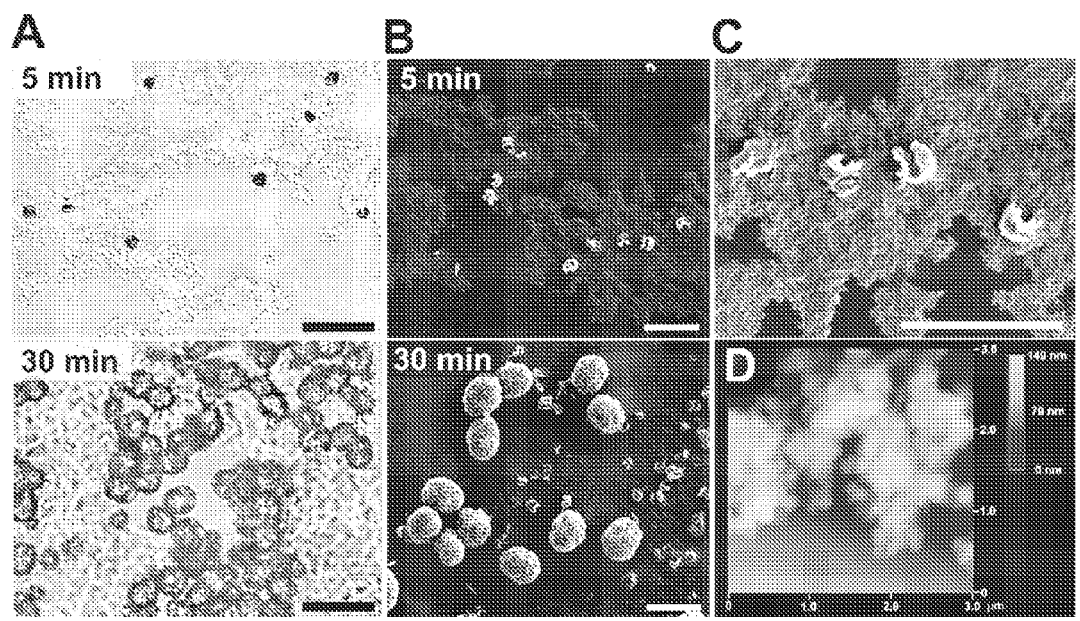
FIG. 9. (A) Light microscopy imaging of NCoH peptide (1 mM) and 400 μM ZnCl$_2$ at specified time points at room temperature (scale bar=20 μm). (B and C) SEM imaging of the NCoH peptide (1 mM) and 400 μM ZnCl$_2$ at specified time points at room temperature (scale bar=10 μm). (C) Close-up of the SEM data at 5 min shown in (B) (scale bar=10 μm). (D) AFM imaging of the background material formed from the NCoH peptide (1 mM) and 400 μM ZnCl$_2$ after 5 min at room temperature.

In another embodiment, a relationship between aggregate formation and reaction time is described. To probe the mechanism of growth, the structures formed at various time points at room temperature were visualized. For instance, the material formed after 5 min with Zn(II) and NCoH was found by light microscopy to be composed of about 1 µm particles with an ill-defined background material (FIG. 9A upper). Visualization of this 5 min experiment by SEM demonstrated that the particles after 5 min were composed of curved sheets similar to those observed with Zn(II) at 4° C. (FIG. 9B, C upper). By 30 min, many mature microflorettes had emerged with diameters greater than 5 µm while a significant amount of the background material had disappeared (FIG. 9A, B lower). Without being bound by theory, it is believed herein that the aggregation process may consist of multiple intermediates starting as an initial amorphous state, going through curved sheets, before finally equilibrating into highly structured microflorettes. Further AFM imaging of the amorphous background material observed by light microscopy and SEM revealed that this material is composed of interconnected and irregularly shaped nano sized spheres (50-250 nm) (FIG. 9D). These structures are similar to the nano spheres observed with NCoH and Ni(II). Without being bound by theory, it is possible that the Ni(II)-promoted nanospheres (FIG. 6E) are trapped in this form, whereas the structure of the Zn(II)-promoted nano spheres may be more dynamic and "evolve" into curved sheet structures followed by the florettes. In another embodiment, aggregation may be temporally controlled.

Figure 10:
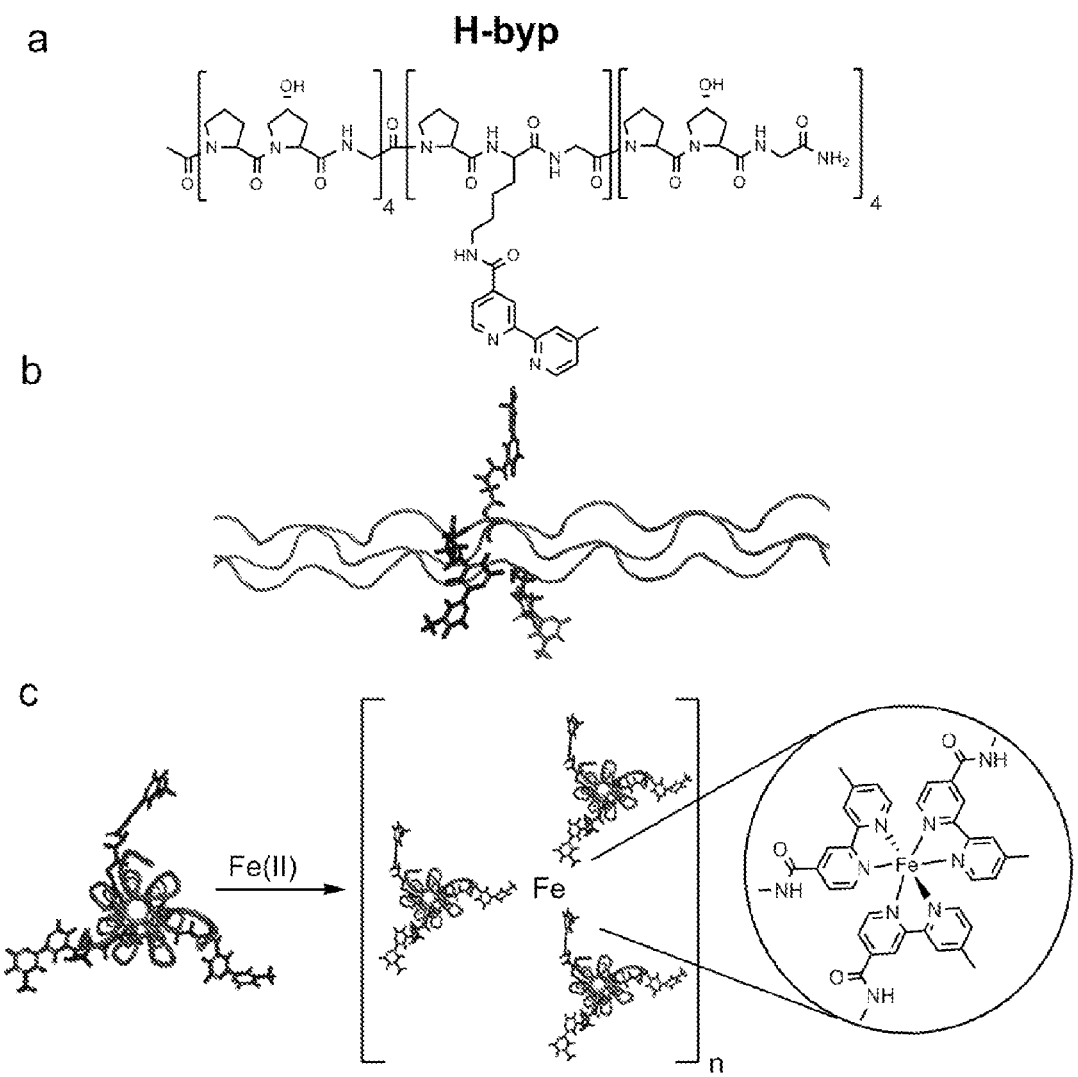
FIG. 10. Collagen-mimetic peptide, triple helix, and metal-triggered aggregation: (a) amino acid sequence of H-byp; (b) side view of H-byp after triple helix formation (peptide, red; bipyridine modification, blue); (c) top view of a single triple helix followed by metal-triggered aggregation.

In another embodiment, a synthetic collagen conjugates capable of aggregating in a radial manner is described. Illustratively, at least one metal binding moiety is covalently attached to a non-terminal residue, optionally through a linker. In one example, one, two, or three bipyridyl-modified lysine residues replace hydroxyproline residues (e.g., compounds H-byp, H-byp$_2$, H-byp$_3$). The position of the three bipyridyl ligands in the center of the triple helix yields three potential directions for radial growth (FIG. 10$b$). Upon the addition of metal ions, multiple triple helices may self assemble in a radial direction, potentially yielding three-dimensional collagen networks (FIG. 10$c$).

The circular dichroism (CD) spectrum of H-byp was examined to determine if the peptide formed a stable triple helix and to investigate the effect of added metal ions. The CD spectrum of H-byp (250 µM) displayed a typical collagen triple helix profile with a maximum at 225 nm, and addition of metal ion, such as Fe(II), had no effect on the CD spectrum, which may be taken to confirm that a triple helix was stable under these conditions. Thermal denaturation studies were performed with H-byp to determine the stability of its triple helix. Although somewhat less stable then (POG)$_9$ (Tm of 67° C.), a Tm of 56° C. was observed for H-byp. However, in the presence of the metal ion Fe(II), the Tm increased to 63° C. Without being bound by theory, it is believed herein that the increase in thermal stability with added metal ion is indicative of metal-promoted aggregation aggregation of multiple triple helixes or to intrastrand coordination within a single triple helix. Upon addition of EDTA (100 mM) the Tm returned to 57° C., indicating that the aggregation is also reversible.

Figure 11:
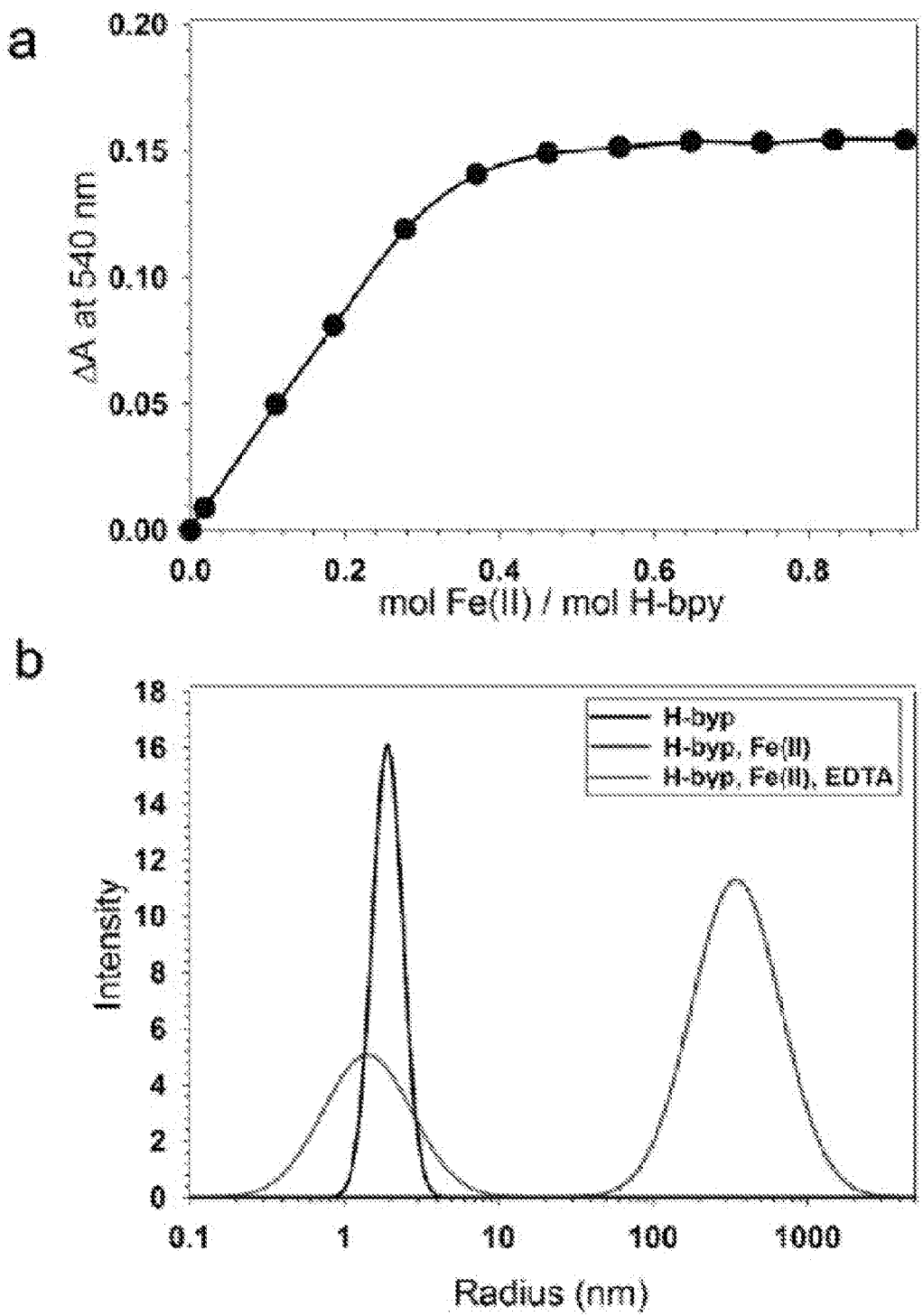
FIG. 11. (a) UV-vis titration of H-byp (54 μM) with Fe(II); (b) dynamic light scattering of H-byp (1 mM), in 10 mM HEPES pH 7.0 (black), with Fe(II) (500 μM) (red), and with Fe(II) (500 μM) and EDTA (100 mM) (green).

Dynamic light scattering (DLS) was used to measure the degree of aggregation upon addition of a metal. A solution of H-byp (1 mM) was preheated to 70° C. followed by addition of Fe(II) (0.5 mM) and 4 day incubation at 20° C. A hydrodynamic radius of approximately 3 nm (FIG. 11). was observed for H-byp, consistent with other collagen triple helical peptides (Cejas et al., J. Am. Chem. Soc., 129:2202-3 (2007)). However, in the presence of Fe(II) a broad distribution of radii were observed with a mean radius of 500 nm. At lower peptide concentrations (250 and 50 µM) larger assemblies were also observed (mean radii of 200 and 150 nm, respectively) in conjunction with monomeric triple helices. Also, the reversibility of the aggregate was observed by adding the metal chelator EDTA. Cu(II) was also shown to cause aggregation of H-bpy.

Figure 12:
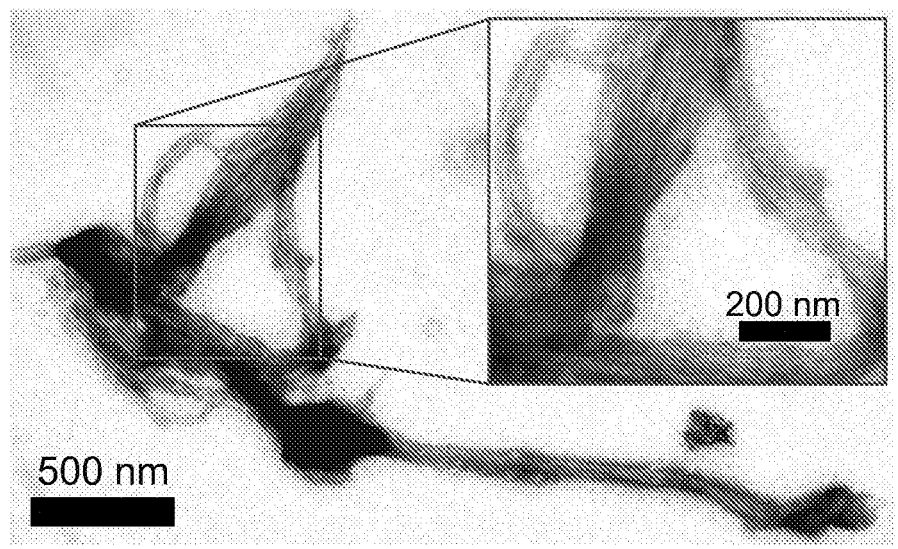
FIG. 12. TEM image of H-byp (2 mM), Fe(II) (0.3 mM), in HEPES (10 mM pH 7.0).

TEM was used to visualize the morphology of the assembled aggregates (H-byp (2 mM) preheated to 70° C. followed by the addition of Fe(II) (0.3 mM) and a 4 day incubation at 4° C.). Fibers were consistently observed with lengths on the order of 3-5 µm, and a number of the fibers displayed extensive branching (FIG. 12). Closer inspection of an unbranched region (see inset FIG. 12) appeared to show bundles of thinner fibers of approximately 10 nm in width. In the absence of Fe(II), no peptide aggregation or fiber formation was observed, consistent with the DLS observations. The fiber morphology is lost at higher concentrations of Fe(II) (1 mM). Without being bound by theory, it is believed herein that saturation of the bipyridyl ligand with metal ions limits peptide aggregation and fiber growth.

Figure 13:
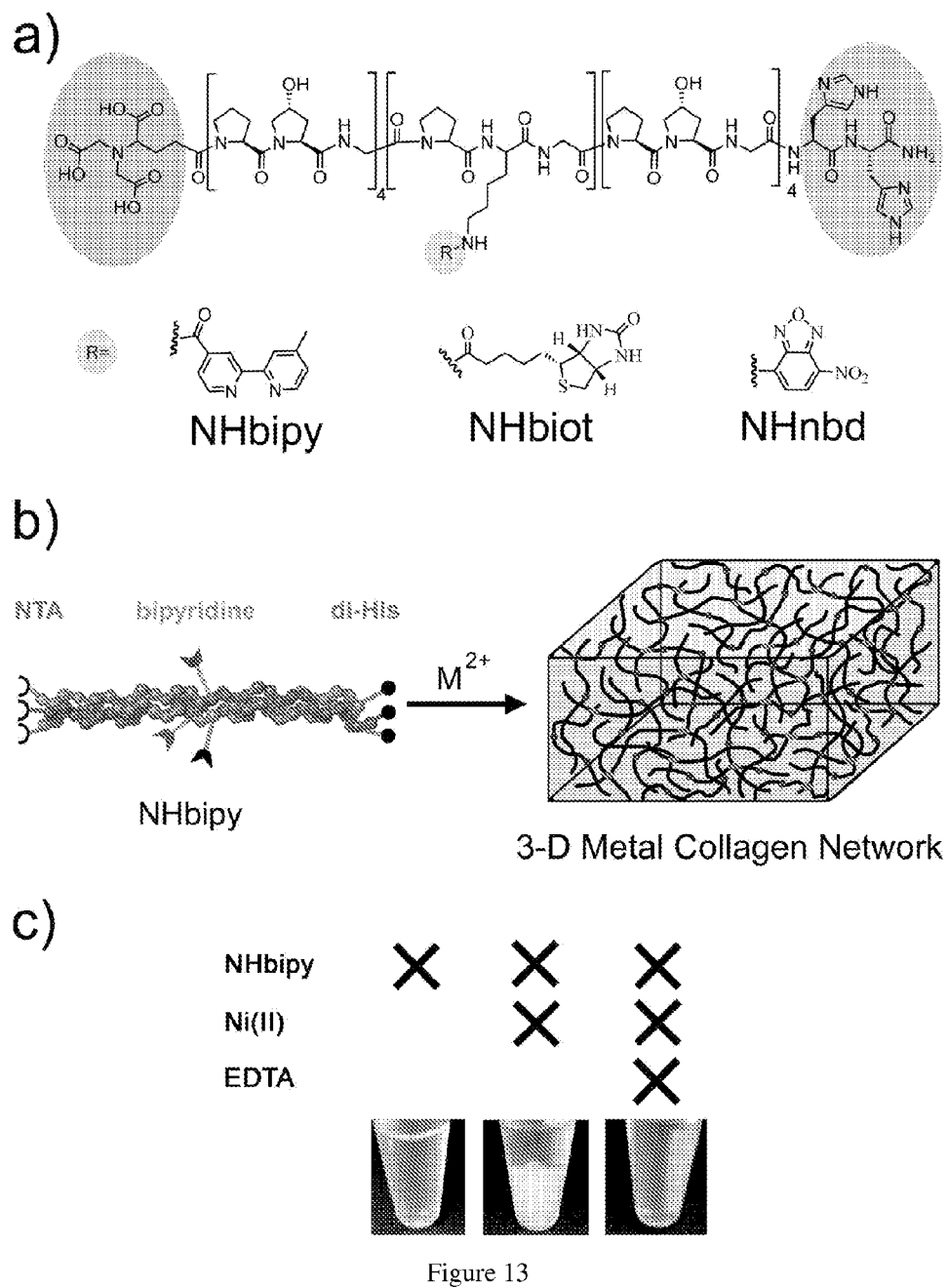
FIG. 13. a) General structure of peptides NHbipy, NHbiot, and NHnbd. b) Schematic representation of the triple helical NHbipy and its aggregation into a highly cross-linked 3-dimensional scaffold following the addition of metal ions. c) Visualization of solution turbidity upon addition of NiCl$_2$ (2 mM) to a solution containing NHbipy (1 mM). The addition of EDTA (1 mM) causes the disappearance of the turbidity.

In yet another embodiment, a crosslinked aggregate (FIG. 13) featuring both linear and radial growth, prepared from a single synthetic collagen conjugate is described. having nitrilotriacetic acid (NTA) unit at the N-terminus of the peptide, a His$_t$ sequence at the C-terminus and a bipyridyl moiety at a central position (e.g., NHbipyr). It is appreciated that the multi-directionality of the metal ligands may provide the opportunity for the formation of extensively crosslinked synthetic collagen conjugate materials. NHbipy assembles in the presence of metal ions under physiological conditions. In addition its subsequent disaggregation using a mild chelating agent, may endow this illustrative system and others described herein with temporal control of the construction of the scaffold. This modular system may also be expanded to allow for the incorporation of other collagen peptides via the NTA/histidine strategy for fluorescent tracking of the polymer and for the interaction with streptavidin. For example, it is demonstrated herein that this synthetic collagen conjugate scaffold encapsulates and maintains human endothelial cells with no observable cytotoxic effects. Therefore, this illustrative scaffold and others described herein may have applications in tissue engineering and regenerative medicine.

CD showed that NHbipy displays a maximum absorption at 225 nm, a value that may be indicative of a polyproline helix found in collagen model peptides. Thermal denaturation demonstrate that the NHbipy forms a stable triple helix at room temperature with a melting temperature of approximately 40° C. These findings may support the premise that both the NTA/His$_2$ and bipyridine modifications do not preclude the peptide from adopting a triple helical structure.

In another embodiment, aggregates of NHbipy are described. Addition of Ni$^{II}$ to the NHbipy solution a turbid solution (FIG. 13c). The image was taken approximately five seconds following the addition of the metal ion, which may indicate that the aggregation process is extremely rapid. Similar results are also observed for Co$^{II}$, Zn$^{II}$, and Cu$^{II}$.

Figure 14:
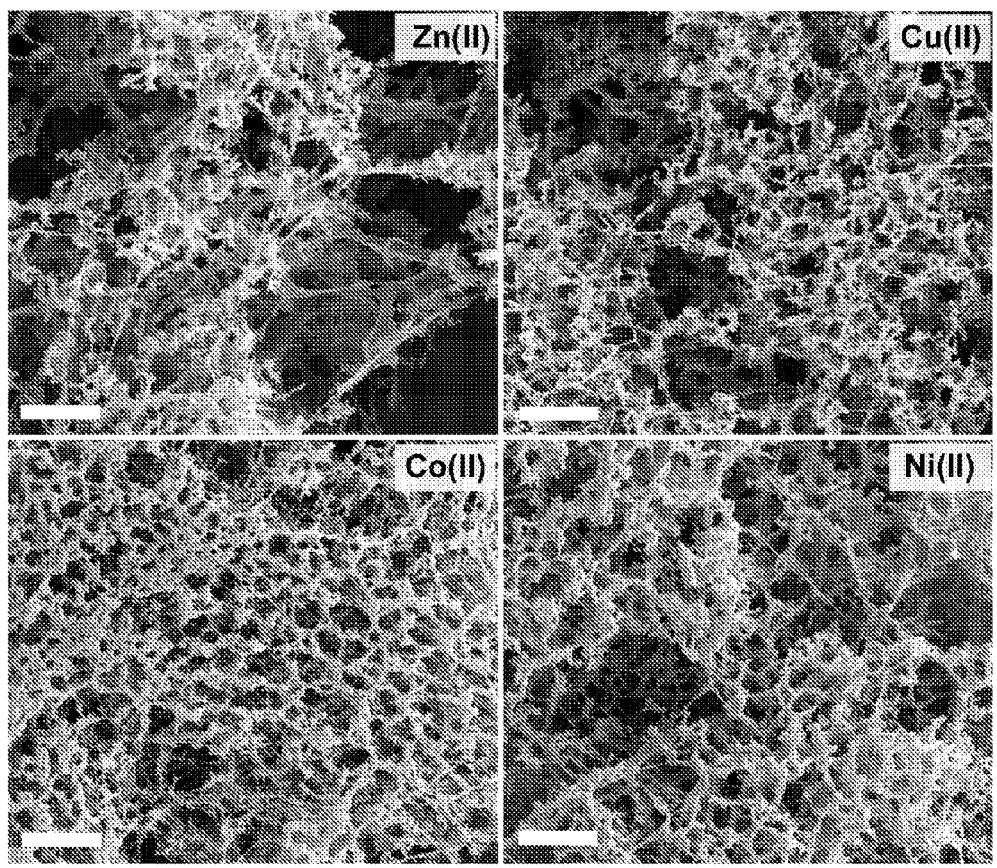
FIG. 14. SEM images of NHbipy peptide (1 mM) with 2 mM of specified metals (scale bar=5 μm).

SEM analysis (FIG. 14) showed that the architecture of the network was composed of highly cross-linked strands. However, variation in overall architecture is observed when the metal ion is varied. Thus, Zn$^{II}$ appears to generate a less dense and more fibrous scaffold. On the other hand, Co$^{II}$, Cu$^{II}$, and Ni$^{II}$ all result in a more cross-linked scaffold as compared to Zn$^{II}$, with internal pores on the order of approximately 5-20 µm. It is also to be understood that the relative metal to peptide ratio may or may not have an effect on the cross-linked scaffold formed. In one illustrative example, with Ni$^{II}$ to NHbipy ratios ranging from 0.4 to 4, it is found that the overall morphology of the mesh remained consistent.

Figure 15:
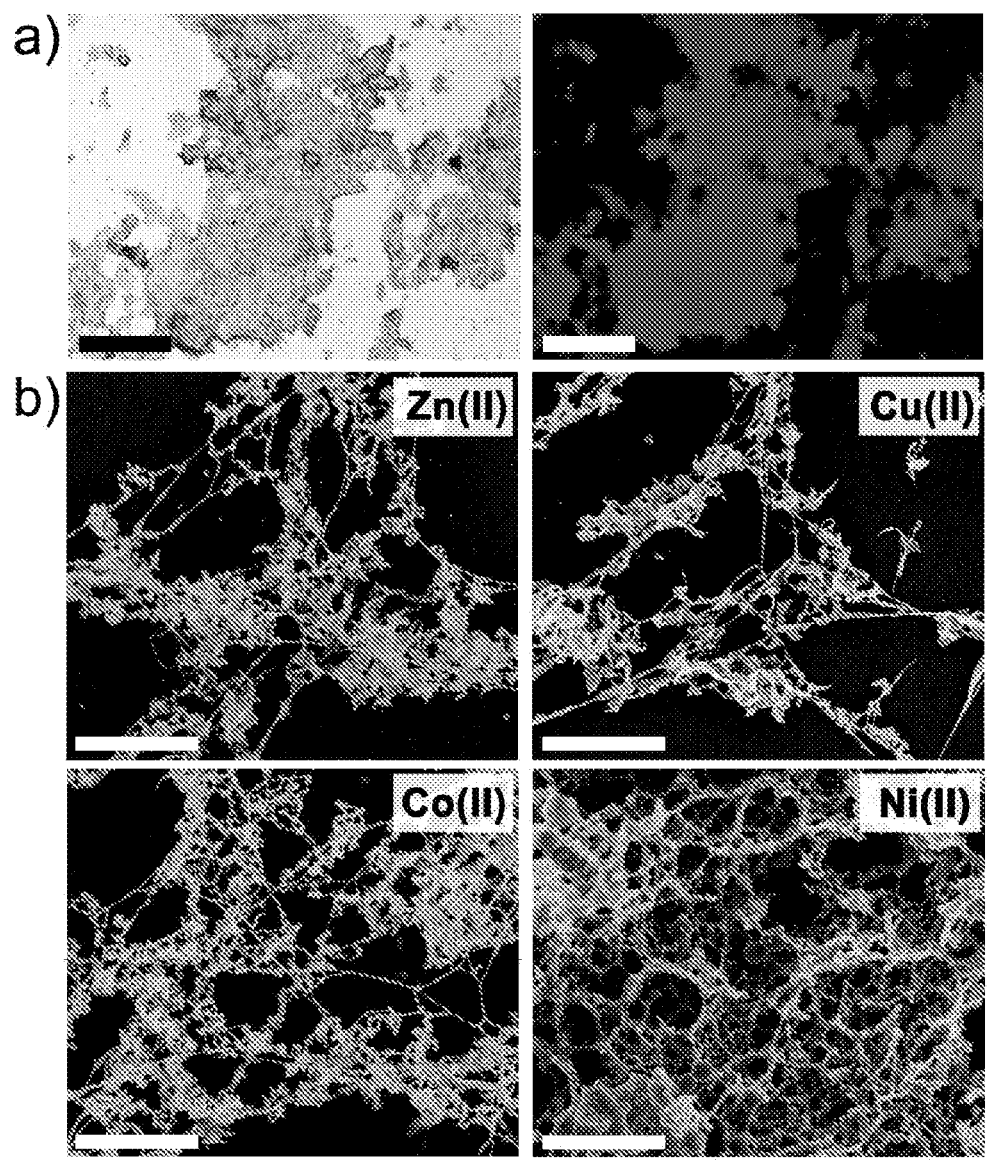
FIG. 15. Incorporation of two distinct metal ions into the NHbipy scaffold. a) Microscopy images of NHbipy (1 mM) with dual metal combination RuII/NiII (1 mM each) (left) fluorescence microscopy (right) bright field microscopy (scale bar=50 μm). b) SEM images of NHbipy (1 mM) with dual metal combinations: RuII/ZnII), RuII/CuII, RuII/NiII, RuII/CoII, 1 mM each (scale bar=4 μm).

In another embodiment, aggregates formed from two or more different metal ions are described. Such aggregates may have tunable affinities for different metal ions, and are therefore also referred to herein as tunable aggregates. In one illustrative example, NHbipy contains both a bipyridine and an NTA/histidine metal binding moiety, it is appreciated that two distinct metal ions may be bound within the assembled network. Dual or multiple ligand aggregation may be used to gain more control over the architecture of the scaffold. In an illustrative example, Ru$^{II}$, a metal that coordinates bipyridine, but may leave the NTA/histidine ligands unbound, was used. The Ru$^{II}$ complex was generated by heating NHbipy (1 mM) with Ru$^{II}$ (1 mM) at 90° C. for 3 h). The peptide solution was then allowed to cool and refold into a triple helix (monitored by CD), followed by the addition of 1 mM of Ni$^{II}$, Zn$^{II}$, Co$^{II}$, or Cu$^{II}$, all metals with an affinity for the NTA/histidine ligands. The scaffolds were first examined by fluorescent microscopy (FIG. 15a) and a red fluorescent scaffold was observed that may be indicative of a (bipy)$_3$Ru$^{II}$ complex (Juris et al., Coor. Chem. Rev., 84:85-277 (1988)).

In another embodiment, the dual metal scaffolds may be further characterized using energy dispersive X-ray (EDX) spectroscopy. Thus, in an illustrative example, it is observed that Ru$^{II}$ was present along with the other respective metal ion. The structure of these materials was characterized by SEM (FIG. 15b) and compared to those obtained with single metals to determine if the dual metal scaffolds contained different architectures. The addition of Ru$^{II}$ was found to effect the scaffold shape when compared to those generated with the single metals Cu$^{II}$, Zn$^{II}$, and Co$^{II}$. In these cases the dual metal materials were found to consist of long rope-like strands with significantly reduced cross-linking. On the other hand, the Ru$^{II}$—Ni$^{II}$ scaffold appear to more closely resemble that obtained with Ni$^{II}$ alone, but with a somewhat more open morphology.

In one embodiment, peptides used in synthetic collagen conjugate may be synthesized using standard Fmoc-based solid phase chemistry. Illustratively, the NTA moiety are incorporated into the N-terminus via a side chain-linked Fmoc-Glu. Following Fmoc deprotection, the terminal amino group was doubly alkylated with tert-butyl bromoacetate to afford the protected NTA unit. Concomitant cleavage from the resin and deprotection of the peptides is accomplished using a TFA cocktail. Peptides described herein are purified to homogeneity using RP-HPLC and characterized with analytical RP-HPLC and MALDI-TOF mass spectroscopy. In an alternative embodiment, peptides used in synthetic collagen conjugate may be synthesized using standard solid-phase synthesis on a Chem Matrix rink amide resin via HBTU coupling using for example, Lys(Mtt)-OH in the central position. The removal of the Mtt protecting group is performed on the solid support with DCM/TFA (98:2), and the free amine is subsequently coupled with 4'-methyl-2,2'-bipyridine-4-carboxylic acid. The peptide is cleaved from the resin with TFA/TIPS/H$_2$O (95:2.5:2.5), purified to homogeneity by reverse phase HPLC, and characterized by MALDI-TOF mass spectroscopy.

In another embodiment, synthetic collagen conjugate that aggregate to form for example, microflorettes and/or meshes are described herein. Such aggregates may be used as delivery vehicles for cells or populations of cells. In one variation, the aggregates also include one or more drugs or compounds to be delivered in conjunction with the cell, such as for example one or more growth factors, cell adhesion peptides, and the like. Illustrative cells that may be delivered in the aggregates described herein include stem cells that may be associated with, bound to, or encapsulated within the aggregates.

In another embodiment, the cells to be delivered are mesenchymal stem cells. In that embodiment, additional growth factors, such as but not limited to bone morphogenetic protein 2 (BMP-2) may also be delivered. It is understood that BMP-2 may be used for differentiating adult mesenchymal stem cells to osteoblasts. In one variation, epidermal growth factor (EGF) may also be delivered. It is appreciated that EGF may stimulate osteogenesis. These and other growth factors may be associated with the synthetic collagen conjugate in a variety of ways. For example, the synthetic collagen conjugate may include His-tagged BMP-2 and/or EGF using for example lysine residues in non-terminal positions of the peptide portion of the synthetic collagen conjugate. Depending upon the morphology, the aggregates may either be present on the surface of the cell to be delivered, such as MSCs, such as in the case where the aggregate is a microflorettes or similar structure, or the cells may be encapsulated in the aggregate, such as where the aggregate is a mesh.

In one illustrative example, RGD peptides are associated with the synthetic collagen conjugate, such as in NHrgd. As a control the microstructures with growth factor-supplemented media are used, or with no growth factor as a negative control. Osteogenic differentiation is examined by monitoring alkaline phosphatase activity, an early marker for bone differentiation, and calcium content. Quantitative reverse transcription-polymerase chain reaction is used to examine transcript levels of bone-specific genes, such as alkaline phosphatase, bone sialoprotein, collagen I, osteocalcin, and osteopontin. The effect of temporal delivery of the His-tagged growth factors BMP-2 and EGF, through bound synthetic collagen conjugate microstructures, on the efficiency of bone marrow MSC differentiation is described.

Human bone marrow-derived MSC have also been shown to differentiate along chondrogenic pathways in the presence of the growth factor TGF-β1. To study MSC differentiation with TGF-β1, the synthetic collagen conjugate meshes with a high density of cells are used. His-tagged TGF-β1 is incorporated with the synthetic collagen conjugate mesh, as well as synthetic collagen conjugates containing cell adhesion peptides. In a typical set of experiments, for instance, the NHbipy and NHrgd peptides are combined with variously His-tagged TGF-β1 and MSC cells in growth factor free media. Addition of Ni(II) is used to trigger the spontaneous (within 1 minute) formation of the mesh. Cell growth is monitored with time (days to months) by dissolving the mesh with an excess of EDTA, followed by counting live cells. To monitor chondrogenesis, sulfated glycosaminoglycans levels within the cells are measured by using a known spectrometric assay with 1,9-dimethyl-methylene blue (Stone et al., Annals of Clinical Biochemistry, 31:147-152 (1994)). Quantitative reverse transcription-polymerase chain reaction is used to examine transcript levels of cartilage-specific genes, such as Sox 9, collagen II, and aggrecan (Dvir-Ginzberg et al., Journal of Biological Chemistry 283.52: 36300-36310 (2008)). To ensure that the cells are not undergoing hypertrophy or becoming bone, transcript levels of collagen X, collagen I, Runx2 and alkaline phosphatase are examined (Dvir-Ginzberg et al., Journal of Biological Chemistry 283.52: 36300-36310 (2008)).

In another embodiment, scaffolds that may be useful for blood vessel formation are described herein. Proper microvasculature is essential for normal tissue function. Therefore, there is strong interest in controlling the synthesis of capillary-like networks in vitro for applications in tissue regeneration. Normal primary HUVEC are a well studied cell line that have been shown to form blood vessels when introduced into compatible 3-dimensional environments with the addition of the appropriate growth factors, such as VEGF. In one embodiment, the mesh formed with the NHbipy peptide is used as a 3-D scaffold for encapsulated HUVEC. The effect of differing rates of variously His-tagged VEGF proteins from the meshes on blood vessel formation is described. Comparison to mesh-encapsulated HUVEC supplemented with soluble VEGF in the media, and HUVEC cells grown in MATRIGEL supplemented with VEGF, is undertaken. The blood vessels that are formed are visualized with light microscopy after treatment of the material with EDTA to remove the synthetic collagen conjugate mesh. These illustrative experiments and others described herein may indicate that the NHbipy peptide mesh with cell adhesion peptides and growth factors are suitable scaffolds for blood vessel formation with HUVEC.

Figure 16:
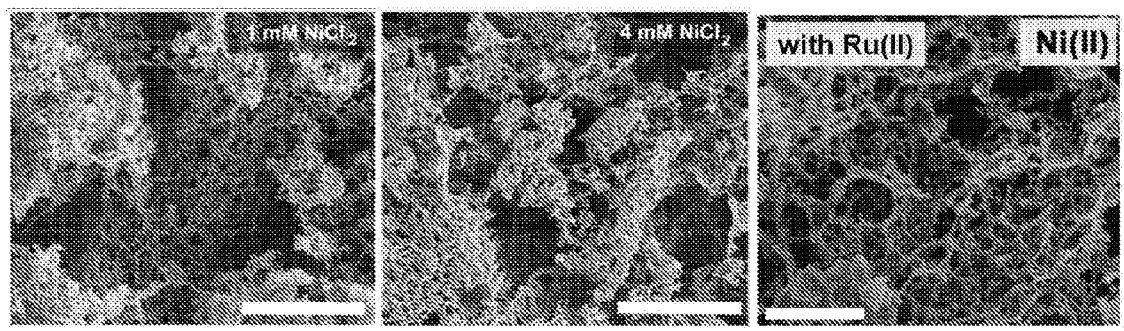
FIG. 16. Formation of NHbipy peptide (1 mM) meshes in the presence of varying amounts of Ni(II) (left and center), and with first addition of Ru(II) (0.5 mM), followed by addition of Ni(II) (0.5 mM) (right) as imaged by SEM. Scale bar=50 μm.

In another embodiment, the physical properties of synthetic collagen conjugate microstructures and their effect on cell binding, differentiation and blood vessel growth are described herein. Physical properties of scaffolds for 3-D cell growth have been found to play an important role, such as the size of pores in the 3-D materials and the stiffness of this material (Sieminski et al., Cell Biochem Biophys 49.2: 73-83 (2007); Sieminski et al., Experimental Cell Research, 297.2: 574-584 (2004)). In one embodiment, the pore sizes within synthetic collagen conjugate meshes by SEM after the addition of cell adhesion containing peptides, His-tagged growth factors and cells is described. Illustratively, it has been discovered that the pore size within the mesh may be increased by varying the NHbipy to Ni(II) ratio (FIG. 16, left and center) or to use two different metal ions in the biomaterial synthesis, such as Ru(II) first followed by Ni(II) (FIG. 16, right). Cell growth, differentiation and tissue growth are monitored with these materials. Numerous studies have pointed to the link between tissue growth and 3-D scaffold stiffness.

In another embodiment, aggregates with high stiffness are described herein. Rheometry is used to measure the stiffness of the NHbipy mesh with and without added His-tagged growth factors and cell adhesion peptides. The factors that may effect stiffness, include but not limited to the metal ion used—Ni(II), Co(II), Cu(II) and Zn(II), with or without Ru(II), the ratio of metal ion to peptide (0.2:1 to 1:1), the overall concentration of the peptide/metal in solution (0.5 to 5 mM), and combinations thereof. The stiffness of the material is measured by rheometry and the data is related to cell binding, growth and differentiation data.

In another embodiment, synthetic collagen conjugate microflorettes are described herein, containing different levels of variously His-tagged growth factors (VEGF, FGF and HGF) and covalently linked cell adhesion peptides, bound to ASC. In one embodiment, ASCs have been isolated according to published procedures, and are cultured in EGM-2 media with or without supplemental growth factors (Cai et al., Stem Cells, 25.12: 3234-3243 (2007)). At passage 3 the cells are detached from the flask with brief trypsin treatment, washed twice with PBS and suspended in saline. The cell suspension is treated with the NCoH microflorettes containing His-tagged growth factors. A full range of functionalized microflorettes alone is evaluated in rats. In one aspect, microflorettes displaying minimal toxicity are used.

Figure 17:
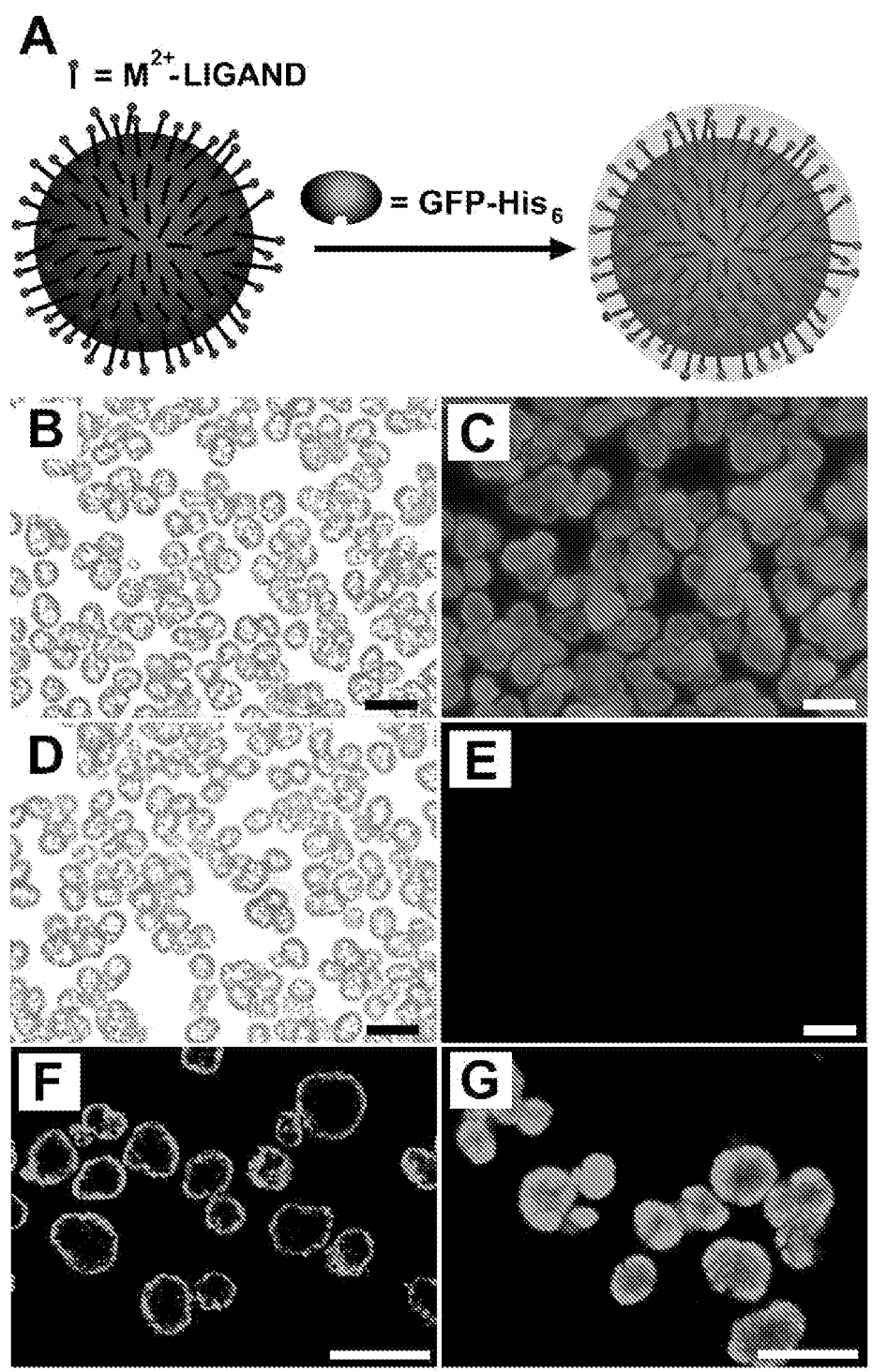
FIG. 17. Protein incorporation of collagen microspheres during and after aggregation. (A) Schematic diagram showing the post-aggregation derivatization of the outer-sphere of the collagen particles with His-tagged GFP. Microspheres formed from NCoH (1 mM) and ZnCl$_2$ (400 μM) were incubated with His-tagged GFP (B and C) and native GFP (D and E). Scale bar, 20 μm. Transmission images (B and D) show the particle morphology while the fluorescence microscopy images (C and E) show the distribution of GFP-emitted fluorescence. (F) Confocal microscopy delineates the localization of GFP-His$_6$ after post-aggregation functionalization of the microspheres. 20 μm. (G) Confocal microscopy delineates the localization of GFP-His$_6$ when functionalization occurs during the formation of microspheres. Scale bar, 20 μm.

In another embodiment, described herein are the binding and temporal release of biologically relevant molecules. Molecular gradients play a vital role in cell signaling, growth and differentiation. The ability to control the delivery of specific growth signals at specific times may have strong potential for improving cell survival and function in vitro and in vivo. An illustrative feature of the collagen biomaterials described herein is the presence of metal/ligands on the surface, and within the scaffolds. For instance, metal-loaded NTA units may be available on the periphery of the microflorettes and the microspheres. These ligands may provide the opportunity to introduce growth factors and cell adhesion peptides that could be released in a spatially or temporally distinct fashion for cell growth/differentiation and tissue engineering/regeneration (FIG. 17A). For instance, RGD peptides have been shown to promote endothelial cell binding due to RGD-cell integrin interactions (Hubbell et al., Biotechnology (NY), 9:568-72 (1991)), and many growth factors, such as FGF and VEGF, have proven successful for tissue engineering (Brey, E. M., et al., Tissue Eng, 11:567-84 (2005)). In one aspect, these peptides and protein may be incorporated into the microstructures if they also contain a metal ligand, such as a His-tag, at their termini. In one embodiment, collagen biomaterial scaffolds are described herein that possess metal/ligands on the surface. In another embodiment, collagen biomaterial scaffolds are described herein that possess metal/ligands within the scaffolds.

In another embodiment, the effect of different transition metal ions on solutions of the peptides is described (10 mM MOPS buffer, pH 7.0). Illustratively, significant turbidity is observed within the solutions of NCoH, Ida-Co-Ida/$H_2$—Co—$H_2$ and NHbipy following the addition of metal ions such as Zn(II), Co(II), Ni(II), and Cu(II). This turbidity could be rapidly reversed upon the addition of an excess of EDTA, demonstrating the reversibility of the metal-promoted self assembly. In one embodiment, dynamic light scattering (DLS) experiments were used to probe the size of the peptide aggregates in solution after addition of metal ions. For example, DLS revealed that addition of metal ions such as Zn(II), Co(II), Ni(II), and Cu(II) to NCoH, Ida-Co-Ida/$H_2$—Co—$H_2$ and NHbipy generated particles in solution with a hydrodynamic radius that was greater than 1 μm (beyond the detection limit of the instrument), whereas the H-byp-based peptides with the addition of metal ions such as Fe(II) generated particles in solution with a hydrodynamic radius that spanned from 250 nm to 1 μm. These assemblies were also found to be fully reversible upon the addition of excess EDTA.

Figure 18:
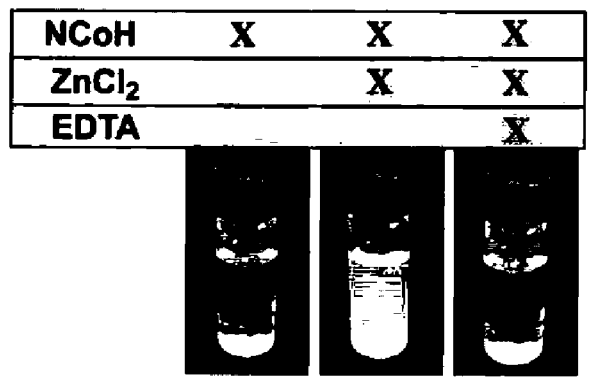
FIG. 18. Reversibility of solution turbidity and particle formation. (A) Visualization of solution turbidity containing NCoH (250 μM) in 20 mM MOPS, pH 7.4, and 1 mM Zn(OAc)$_2$. The addition of EDTA (10 mM final concentration) causes the disappearance of the turbidity. (B) Solution turbidity was monitored by measuring optical intensity at 313 nm for the above solution of NCoH and Zn(OAc)$_2$. At the specified time intervals, EDTA was added (10 mM final concentration), followed by further addition of Zn(OAc)$_2$ (final concentration 3 mM). (C) DLS analysis of chelation competition experiments using the NCoH peptide. Hydrodynamic radius measurements were obtained using 200 μM of peptide with 100 μM of ZnCl$_2$ in 20 mM MOPS (pH 7.4) followed by the addition of EDTA (10 mM final concentration).
Figure 18:
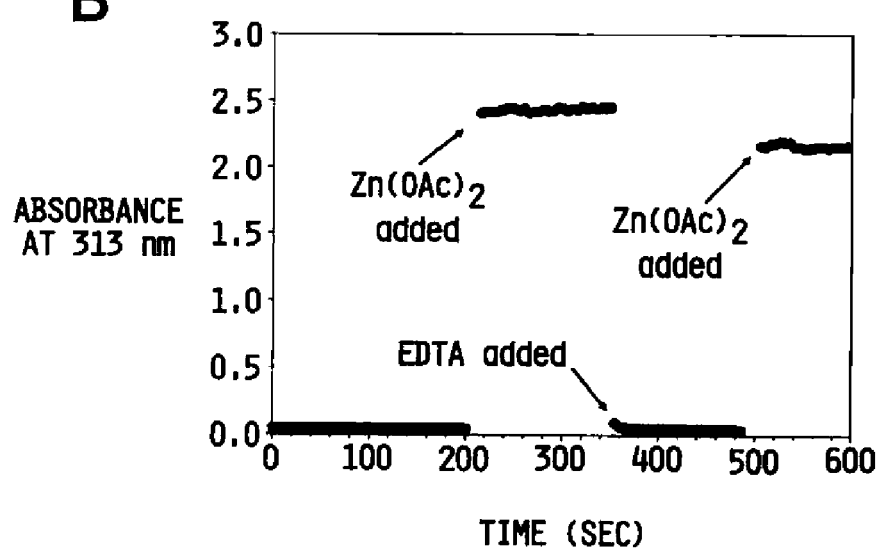
Figure 18:
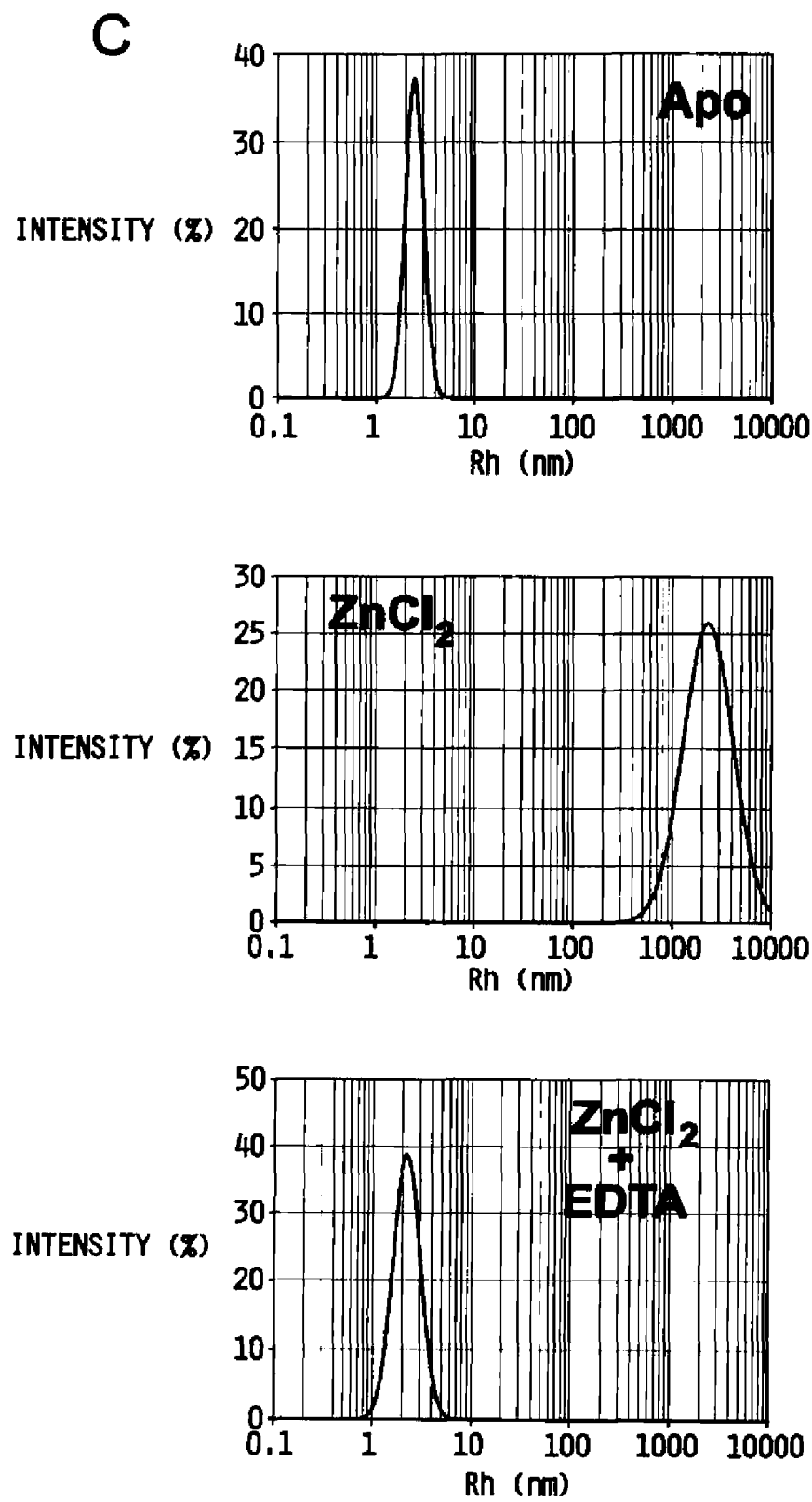

In another embodiment, chelation competition experiments are described herein. Illustratively, these chelation competition experiments were performed using EDTA. In one embodiment, these experiments are useful to demonstrate that the metal ion was mediating the aggregation of the individual peptides. Illustratively, when excess EDTA was added to the turbid solution containing $Ni^{II}$, the turbidity was found to disappear within minutes (FIG. 13c). Without being bound by theory, it is envisioned that, if metal coordination is an intrinsic component of the aggregates, it may be possible to sequester the metal ions with externally added ligands, leading to disruption of aggregation. It was found that addition of an excess of EDTA to a solution of the $ZnCl_2$-generated particles caused a rapid disappearance of solution turbidity (FIG. 18A,B). Full reversibility was observed after addition of the EDTA; reintroduction of metal ions to this same solution yielded a turbid solution once again and this cycle could be repeated. DLS experiments after the addition of EDTA to the $ZnCl_2$-generated particles provided data that was consistent with the metal-free NCoH triple helical peptide (FIG. 18C). Electron-dispersive X-ray (EDX) analysis confirmed the presence of Zn(II) and Cu(II) ions in the NCoH-based particles. These data together may possibly indicate that the metal ion is a key mediator in the formation of the synthetic collagen conjugate assemblies.

Figure 19:
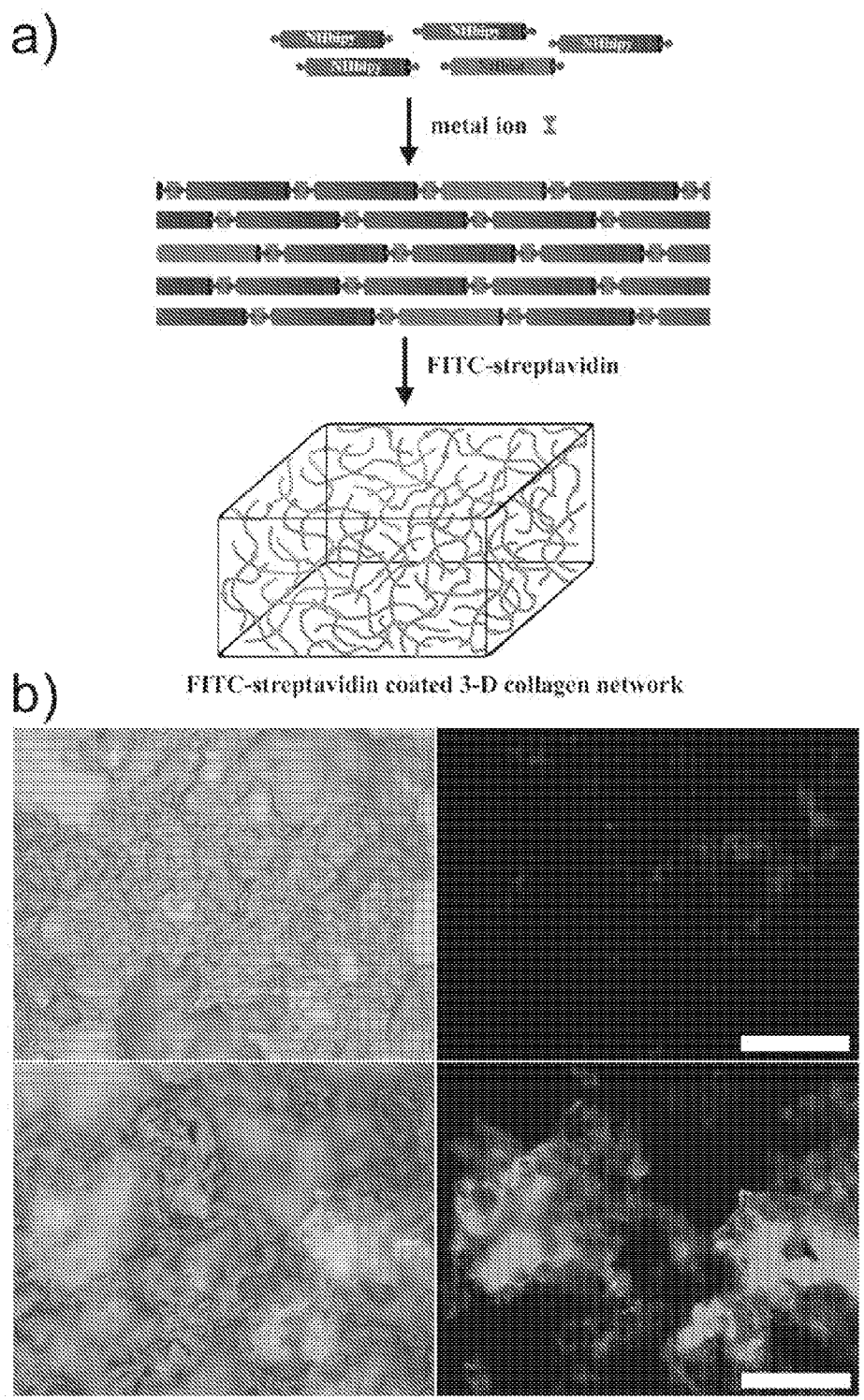
FIG. 19. a) Overall strategy for incorporation of biofunctionality within the three-dimensional matrix of NHbipy, NHbiot, and NiII. B) Bright field (left) and fluorescence (right) microscopy images displaying fluorescence due to binding of FITC-streptavidin with increasing amounts of NHbiot [0% (top right), 16% (bottom right)] (scale bar=200 μm).

In another embodiment, described herein is a general method that may allow for the display of biofunctional moieties within the 3-dimensional framework of the scaffold. In one illustrative embodiment, a peptide was synthesized with a biotin handle (NHbiot—FIG. 13) in place of the bipyridine. Since NHbiot retains the NTA/histidine metal binding moieties, it was expected to be reliably incorporated into the growing biopolymer of NHbipy, thus decorating the scaffold with biotin. Varying concentrations of NHbiot were co-incubated with NHbipy and metal ions to generate scaffolds with the potential of displaying increasing density of biotin moieties. These scaffolds were treated with fluorescein-labeled streptavidin and fluorescence microscopy images indicated with NHbiot was incorporated in the matrix (FIG. 19). It is appreciated that other functionalities may be incorporated into the 3-dimensional matrix and that these functional groups are surface exposed to interact with their respective binding partner.

In one illustrative embodiment, the pre-formed NCoH/Zn(II) microspheres were treated with both His-tag GFP and native GFP. After extensive washing, fluorescence microscopy confirmed that His-tagged GFP was bound to the particles (FIGS. 17B and C), but native GFP was not (FIGS. 17D and E). Confocal microscopy on the His-tagged GFP microspheres demonstrated that the GFP was bound to the surface of the particle (FIG. 17F). In an alternate experiment, His-tagged GFP was included in the synthetic collagen conjugate solution prior to the addition of metal ions. After addition of $ZnCl_2$, identical collagen microflorettes were obtained as described above, except that GFP was found throughout the particle and not only on the surface as determined by confocal microscopy (FIG. 17G).

Figure 20:
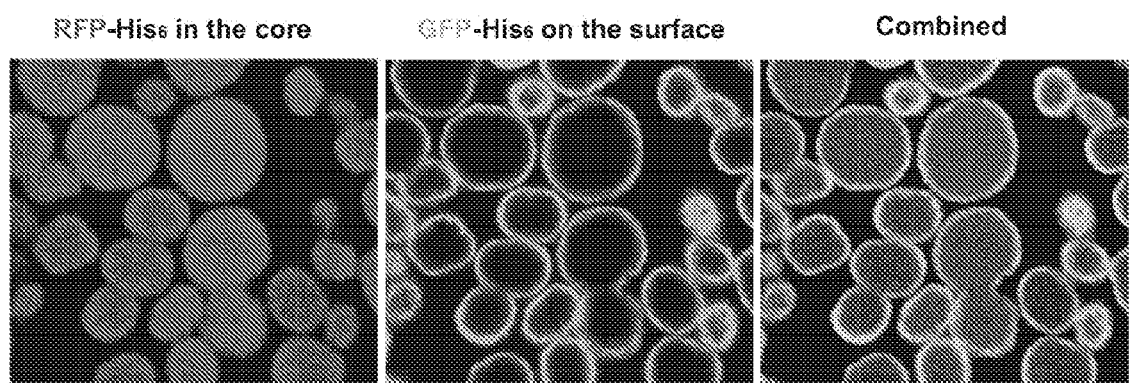
FIG. 20. Confocal microscopy images of fluorescent protein modifications of microspheres. RFP imbedded microspheres were constructed by added ZnCl$_2$ (400 μM) to a solution containing 1 mM NCoH peptide, 0.3 μM of His-tagged RFP in 20 mM MOPS (pH 7.4). Microspheres were washed 2×, incubated with 0.3 μM of His tagged GFP for 1 h, washed 1×. Confocal microscopy analysis was performed on the final microstructures.

In another illustrative example, in order to confirm that different proteins may be incorporated into distinct regions of the microflorettes, His-tagged red fluorescent protein (RFP) was used during the synthesis of the particles, and His-tagged GFP was added after aggregation. Confocal microscopy was used to evaluate the intra-particle distribution of the proteins (FIG. 20). Red fluorescence (left panel) was observed to localize throughout the particle and green fluorescence (center panel) was localized on the surface of the particles. Overlay of the red and green channel demonstrated that dual incorporation was accomplished. These experiment may confirm that RFP was incorporated within the core of the microflorettes, whereas GFP was associated with the exterior portion of the particles. Similar His-tagged GFP experiments were performed with the meshes obtained from the NHbipy peptide and have also confirmed that it is possible to take advantage of the unsatisfied metal/ligand pair within these biomaterials as well.

In another embodiment, the release of growth factors and other bound proteins from the microspheres is described herein with controlled degradation of aggregates. Illustratively, this release of growth factors and other bound proteins from the microspheres may have utility for tissue growth applications. Thus, in the case of the His-tagged fluorescent proteins, their release was monitored from the microstructures by fluorescence spectroscopy in the presence of low concentrations of EDTA and imidazole (approx. 0.1 mM and 2 mM respectively), and in the presence of cell growth media, such as RPMI-1640 and DMEM media. It was found that the addition of excess EDTA (10 mM) to the microspheres resulted in complete dissolution of the particles and release of GFP into solution within 10 sec.

In another embodiment, described herein are other means of temporal control with these microstructures, in addition to the sub-particle localization. In one illustrative embodiment, the nature of the ligand that is bound to the biologically relevant molecule, and the role that the length of the His-tag has on temporal release of bound molecules from the microflorettes and meshes are described herein. In an illustrative example, an active peptide form of the growth factor VEGF, QK (Diana et al., Chemistry, 14:4164-6 (2008); D'Andrea et al., Proc Natl Acad Sci USA, 102:14215-20 (2005)), (Ac-KLTWQELYQLKYKGI-NH$_2$) is used, with no His-tag and with 3 to 6 His moieties and a Gly$_2$ spacer at the N- or C-terminus. These peptides may be prepared synthetically and each incorporated either within (during synthesis) or on the exterior (after synthesis) of the microflorettes and the meshes using the procedures described herein. Release of the His-tagged peptides from the microstructures in the presence of cell growth media and serum is monitored with time by LC/MS. It is appreciated that a range of temporal release capabilities from the microstructures may be in the range from days to week to months.

In another embodiment, described herein is the incorporation of the optimized ligands from the peptides described herein into growth factors, such as the growth factors vascular endothelial growth factor (VEGF), transforming growth factor (TGF-β, bone morphogenetic protein 2 (BMP-2), epidermal growth factor (EGF), fibroblast growth factor (FGF) and hepatocyte growth factor (HGF) through incorporation of the relevant length His-tag. This is accomplished by either cloning the genes of interest into existing expression vectors containing 6 His residues (such as the pET vector series from Invitrogen) or by using PCR to incorporate the desired number of His residue (3-5) at the N- or C-terminus of the gene of interest, followed by incorporation into a suitable expression vector. The release of the variously His-tagged growth factors incorporated either on the interior or exterior of the microstructures is monitored over time (days to months) in the presence of cell growth media and serum with commercially available ELISA assays (R&D Systems). This same technique is also evaluated for the incorporation of cell adhesion molecules, such as RGD and YIGSR, into the microstructures through His-based ligands. In one embodiment, the growth factors described herein include, but are not limited to, VEGF, TGF-β, BMP-2, EGF, HGF, and the like.

In another embodiment, compounds, compositions, and methods are described comprising exogenous populations of cells that may be delivered to a patient using the compounds and compositions described herein.

In another embodiment, aggregates of synthetic collagen conjugate having microflorette morphology are described as delivery vehicles for human adipose derived stem cells (ASC). Adult stem cells have great potential for use in regenerative medicine and tissue replacement after injury or disease because of their capacity to differentiate into a wide variety of cell types (Oswald et al., Stem Cells, 22:377-84 (2004); Ringe et al., Naturwissenschaften, 89:338-51 (2002)). For example, mesenchymal stem cells derived from bone marrow have the ability to produce mesenchymal tissues such as bone, cartilage, fat, tendon and muscle, and marrow stroma can also differentiate into neural cells and endothelial cells (Molchanova et al., Biology Bulletin, 35:555-570 (2008)). Illustratively, human ASC possess the ability to differentiate into multiple mesenchymal cell types in vitro, including endothelial cells. It is believed herein that ASC may be induced into functional endothelial cells in vitro when treated with soluble VEGF and FGF.

In another embodiment, evaluation of the synthetic collagen conjugate microstructures using stem cell differentiation is described herein. Illustratively, the ability to induce specific differentiation of human stem cells into a variety of cell types may be a potential means to generate a reliable and personalized source of cells for tissue engineering and transplantation purposes (Burdick et al., Tissue Engineering, 15: 205-219 (2009)). One such example are bone marrow-derived MSC. MSC are fairly well characterized and have been differentiated into adipogenic, osteogenic and chondrogenic cells depending on the environmental stimuli (Molchanova et al., Biology Bulletin, 35.6: 555-570 (2008)).

In another embodiment, covalent modification with cell adhesion molecules is described herein. In one illustrative example, covalent modification with RGD-based peptides is described. The central bipyridyl-moiety of NHbipy is replaced with small peptide sequences that mimic full-length integrin binding domains critical for cell adhesion and growth. By controlling the ratios of NHbipy to synthetic collagen conjugates containing cell adhesion peptides control of the effective concentrations of the cell adhesion molecules is accomplished. It is to be understood that a variety of cell adhesion peptides may be simultaneously incorporated into the collagen networks creating a heterogeneous 3-dimensional cell adhesion environment.

RGD-based peptides have been used extensively to promote endothelial cell binding due to RGD-cell integrin interactions (Hubbell et al., Biotechnology (NY), 9:568-72 (1991)). RGD modifications may also promote platelet adhesion and aggregation because platelets also express integrin receptors that recognize RGD sequences. In one aspect, the binding of His-tagged REDV and YIGSR is described. These two peptides promote endothelial cell adhesion, but not platelet binding. Accordingly, the following synthetic collagen conjugates were synthesized: NHrgd, NHred and NHyig. In each case the integrin binding domain peptides RGD, REDV and YIGSR are integrated attached to the central region of the NCoH synthetic collagen conjugate.

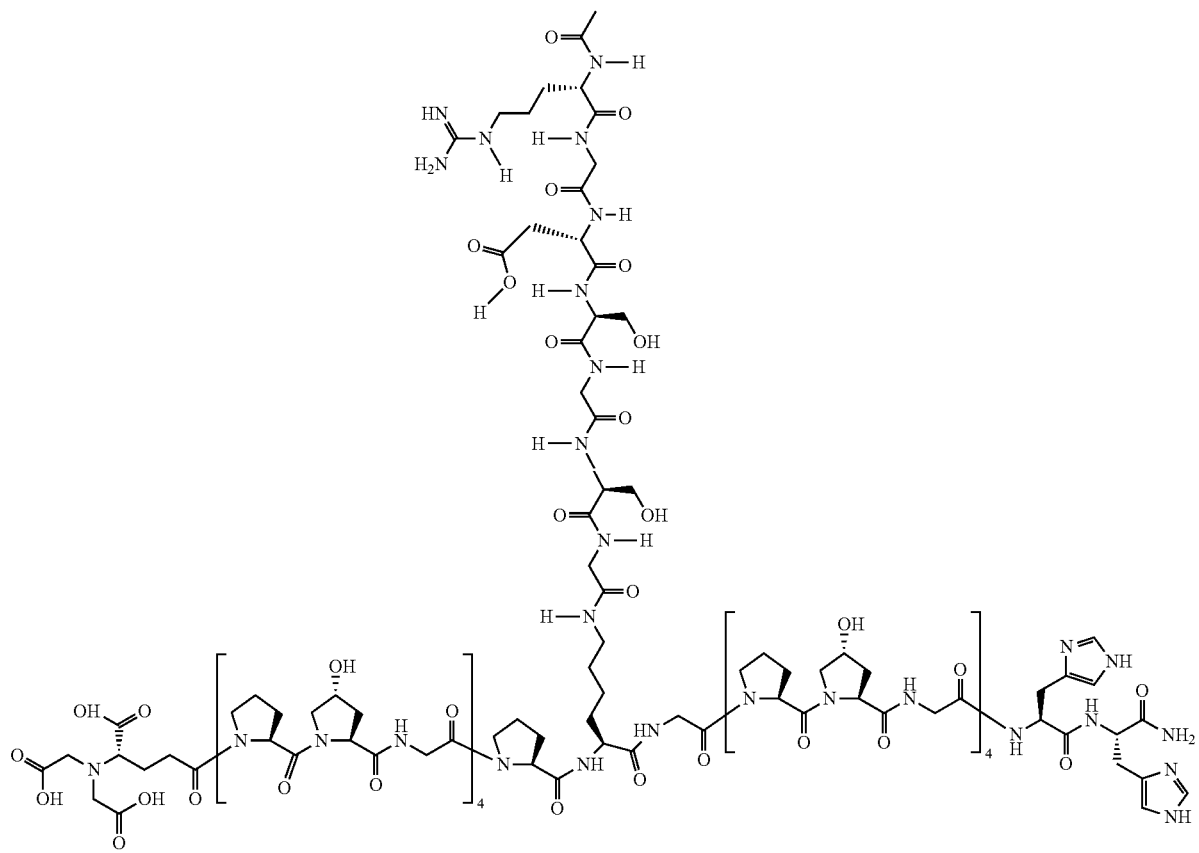

The integrity of the meshes and microflorettes formed was evaluated by SEM with increasing mol % of modified collagen-peptide to NHbipy. Also, the simultaneous use of both the His-tag and covalent modification of the microstructures was evaluated to allow for concurrent delivery and display of relevant biomolecules. For instance, both His-tagged VEGF and NHrgd are incorporated during the synthesis of the microstructures, and structural integrity of the material, cell binding and growth is monitored.

Figure 21:
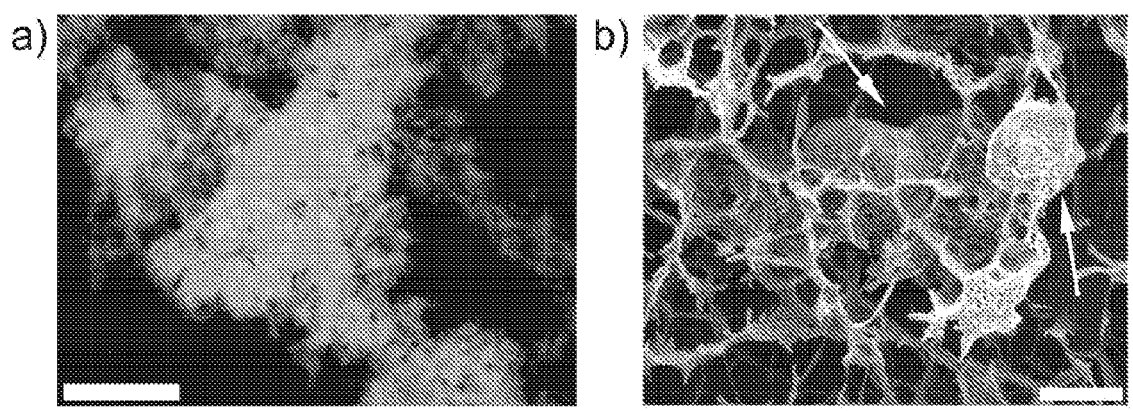
FIG. 21. Visualization of cell encapsulation within the NHbipy/NHnbd matrices. a) Fluorescence microscopy visualization of HeLa cells encapsulated within the NHbipy/NHnbd-Ni(II) matrix (scale bar=200 μm). b) Cryo-SEM image of HeLa cells encapsulated within the NHbipy/NHnbd-NiII matrix (scale bar=10 μm). A representative sectioned cell imbedded in the matrix is indicated by the arrow.

In one embodiment, described herein is the encapsulation of cells in media allowing for normal cell growth. In an illustrative example, NHbipy-based matrices were used. Previous results using NHbiot in combination with NHbipy may demonstrate that it is possible to incorporate other synthetic collagen conjugates with central modifications that contain NTA/histidine ligands at the ends. This strategy was extended to a new peptide (NHnbd—FIG. 13) that contains an NBD fluorophore anchored to the central lysine residue. NHnbd. It is appreciated that a wide variety of diagnostic and imaging agents may be used to label the assembled matrix, and, therefore, could be used to conveniently track the scaffold using standard fluorescence microscopy techniques. Upon the addition of metal ions to a solution containing NHbipy (1 mM) with a small fraction of NHnbd (20 μM) a highly fluorescent collagen network was constructed, further confirming that different collagen sequences may be incorporated into the scaffold (FIG. 21).

In another illustrative example, in order to demonstrate that the collagen metal framework was capable of cellular encapsulation, metal ions were added to a solution containing NHbipy/NHnbd and HeLa cells (stained with the Hoechst 33342 nuclear dye) in DMEM media with 10% serum. Fluorescence microscopy imaging (FIG. 21a) may indicate that the fluorescently labelled NHbipy scaffold formed, and was capable of efficiently encapsulating cells using various metal ions. With the matrix, HeLa cells (blue nuclei) were found to be fully surrounded by the fibrous collagen-based network (green) and remained associated within the assembled matrix (FIG. 21a). This was confirmed using cryo-SEM imaging of the $Ni^{II}$ matrix containing cells (FIG. 21b). In order to confirm the viability of cells within the $Ni^{II}$ matrix, an MTS assay and calcein-AM staining was performed on the encapsulated HeLa cells. It was observed that the cells within the scaffold were as viable as the cells cultured on normal tissue culture plates. Overall, these findings may indicate that HeLa cells continue to proliferate when encapsulated within the NHbipy scaffold even after several days of culture.

Figure 22:
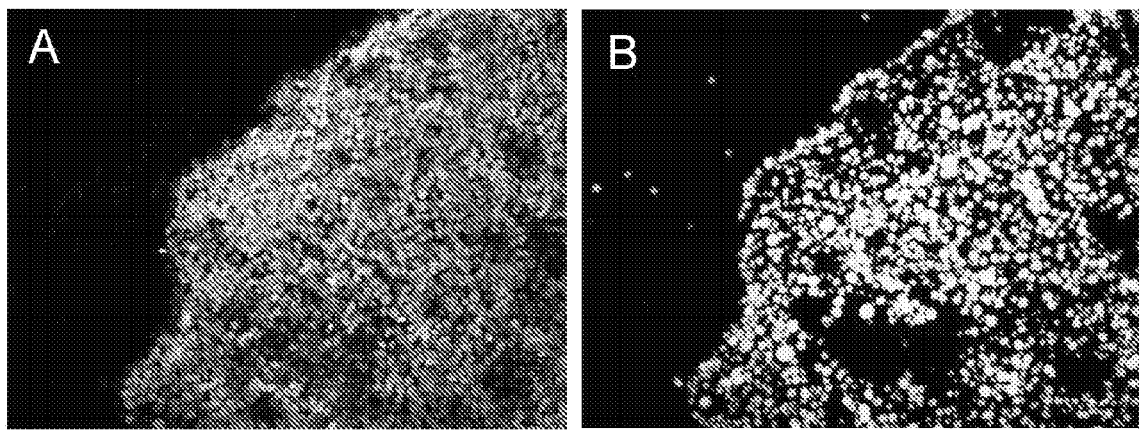
FIG. 22. A monolayer of HeLa cells was labeled with Hoechst 33342 prior to incubation with NCoH microflorettes (ZnII) containing NHnbd (2 mol %). Cells were incubated with fluorescently labeled microflorettes for 45 min in DMEM media, washed with PBS and visualized using fluorescence microscopy.

In additional illustrative examples, experiments with the microflorettes derived from the NCoH peptide focused on the association of the microstructures with cells in 2-D culture. For instance, a monolayer of HeLa cells labeled with Hoechst 33342 were treated with microflorettes that contained 2 mol % of NHnbd to allow for visualization, followed by extensive washing. The microstructures were found to be preferentially associated with regions of the plate containing cells (FIG. 22). Without being bound by theory, it is believed herein that the microflorettes may have inherent cell binding properties.

ILLUSTRATIVE EXAMPLES

The following illustrative examples describe particular embodiments of the invention. However, these examples are illustrative only, and should not be construed to limit the scope of either the specification or the claims.

Example

Materials. Rink Amide Chem Matrix resin was purchased from Matrix Innovation Inc. (Montreal, Canada). All amino acids and activating agents for peptide synthesis were purchased from Novabiochem (La Jolla, Calif.). FITC-labelled streptavidin was purchased from Anaspec (San Jose, Calif.). AFM wafers were purchased from Ted Pella, Inc. (Tustin, Calif.). CellTiter 96 AQeous One Solution Cell Proliferation Assay was purchased from Promega (Madison, Wis.). Fmoc-protected amino acids, Fmoc-Gly-OH, Fmoc-Pro-OH, Fmoc-Hyp(t-Bu)-OH, and Fmoc-Lys(Mtt)-OH (Mtt: 4-methyltrityl group) were purchased from Novabiochem. Activating agent HBTU was purchased from Novabiochem. Dichloromethane ($CH_2Cl_2$), N-methylpyrrolidone (NMP), dimethylformamide (DMF), N-ethyldiisopropylamine (DIEA), trifluoroacetic acid (TFA), triisopropylsilane (TIPS), and diethyl ether were purchased from Aldrich (St. Louis, Mo.). 4-(2-hydroxyethyl)-1-piperazineethanesulfonic acid (HEPES), iron(II) perchlorate hydrate (Fe$(ClO_4)_2 \cdot xH_2O$), zinc(II) chloride ($ZnCl_2$), copper(II) chloride ($CuCl_2$), and nickel(II) chloride ($NiCl_2$) were all purchased from Aldrich. All other chemicals were purchased from Sigma Chemical Co. (St. Louis, Mich.) and used without further purification. All peptide filtrations were performed using Nylon filters (0.45 μm) from Chrom Tech.

Example

4'-methyl-2,2'-bipyridine-4-carbaldehyde. The synthesis of 4'-methyl-2,2'-bipyridine-4-carbaldehyde was performed from a previously procedure (Peek et al., Int J Pept Protein Res, 38.2: 114-23 (1991)). In a 200 mL round-bottomed flask was 4'-methyl-2,2'-bipyridine (1.5 g, 8.14 mmol) in Dioxane (62.6 ml). Argon was bubble into the solution for 15 minutes before the addition of selenium dioxide (1.012 g, 9.12 mmol). Argon was bubbled for another 20 minutes before heating the solution at reflux for 24 hrs. After the flask was cooled to room temperature the solution was filtered and the solvent reduced. The remaining solid was dissolved in ethyl acetate and heated at reflux for 1 hr followed by a hot filtration. The filtrate was then washed with 0.1M sodium carbonate and extracted with 0.3 M sodium metabisulfate. The pH of the aqueous layer was adjusted to 10 with sodium bicarbonate and the product was extracted with DCM. The solvent was removed under vacuum and no further purification was need for the white solid. (Yield: 49.1%).

Example

4'-methyl-2,2'-bipyridine-4-carboxylic acid. The synthesis of 4'-methyl-2,2'-bipyridine-4-carboxylic acid was performed from a previously reported protocol (Peek et al., Int J Pept Protein Res, 38.2: 114-23 (1991)). In a 100 mL round-bottomed flask was 4-methyl-2-2-bipyridine-4-carbaldehyde (1.63 g, 8.22 mmol) in Ethanol/water (95 ml). Silver nitrate (1.446 g, 13.40 mmol) in water (1 ml) was added to the stirring solution. Sodium hydroxide (10 ml, 10.00 mmol) was added via an addition funnel over 20 minutes and the solution was stirred for 24 hrs. After stirring the black solution, the ethanol was removed under reduced pressure and the white solid was filtered. The solid was filtered with 1M NaOH and with water. The combined aqueous filtrate was extracted with DCM and then the pH of the aqueous layer was adjusted to 3. The white precipitate was filtered and dried under reduced pressure. No further purification was needed. (Yield: 50.1%).

Example

General Syntheses of Peptides

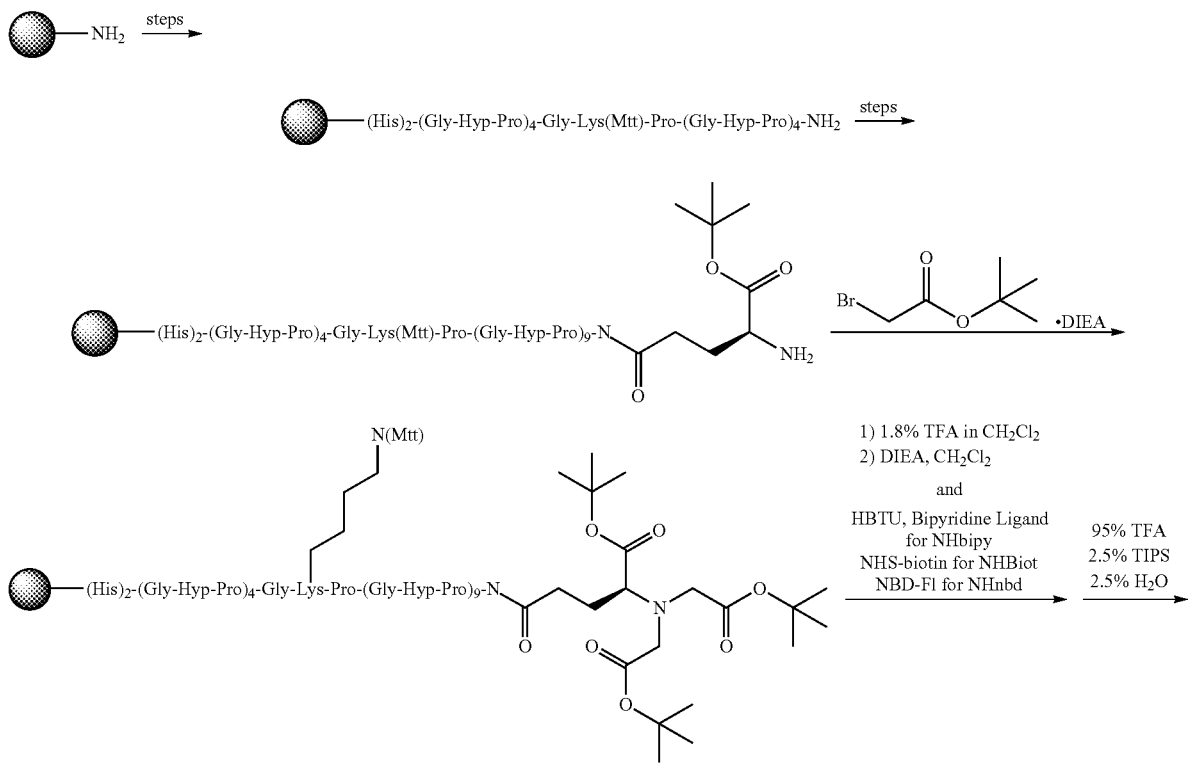

-continued

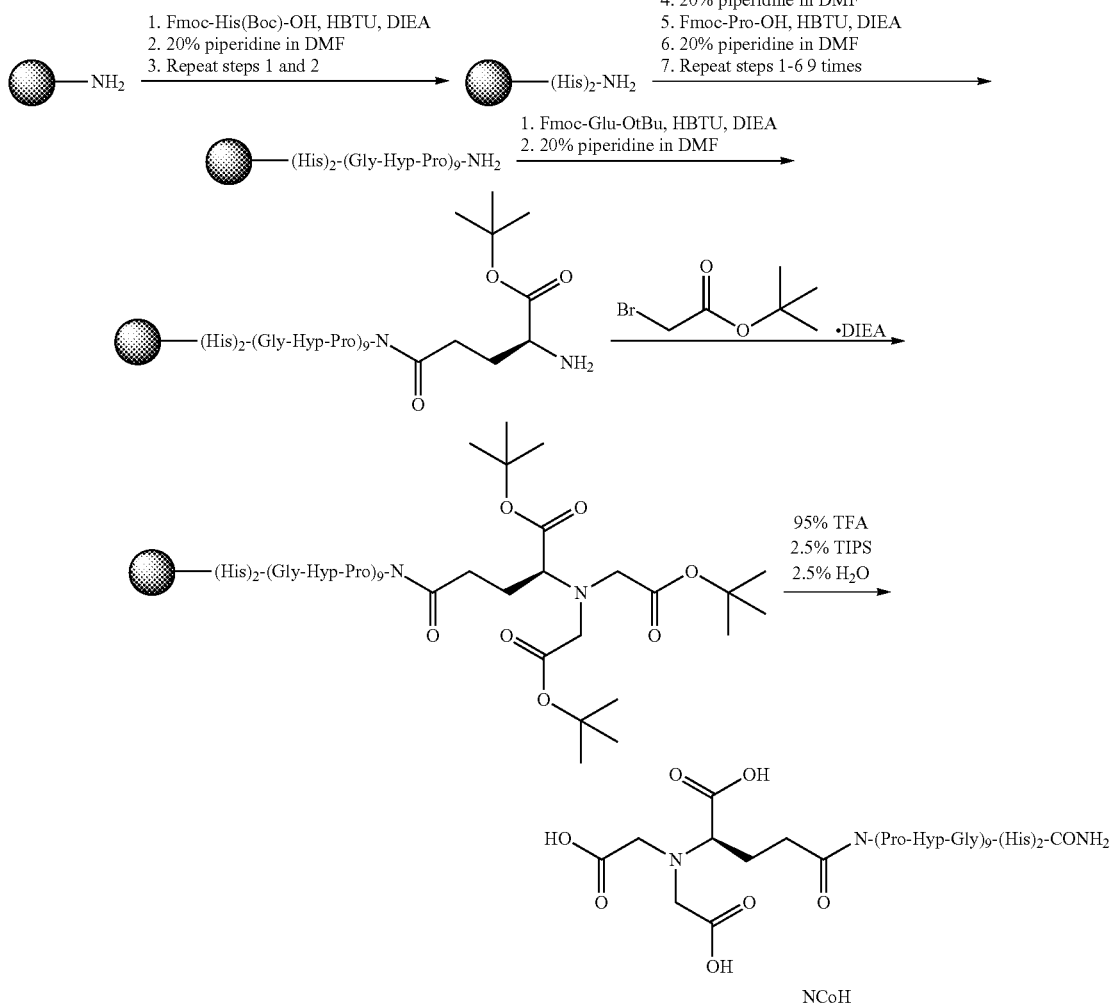

A 10 ml peptide synthesis flask was charged with 400 mg (0.20 mmol) of Rink Amide Chem Matrix resin. The resin was initially washed with $CH_2Cl_2$ (3×5 ml) and DMF (3×5 ml). Fmoc-protected amino acids (5 equiv, 1.0 mmol) in NMP (5 ml) were added to the reaction flask with HATU (5 equiv, 1.0 mmol) and DIEA (10 equiv, 2.0 mmol), and the flask was agitated for 3 h. The resin was washed with DMF, $CH_2Cl_2$, MeOH, $CH_2Cl_2$, and DMF (3×5 ml each). Piperidine (20% in NMP, 5 ml) was added to the reaction flask, the flask was agitated for 25 min, and the piperidine solution was drained. The resin was washed with DMF, $CH_2Cl_2$, and MeOH (2×5 ml each). These steps were repeated until all amino acids were coupled to the resin. For the final Fmoc deprotection, piperidine (20% in NMP, 5 ml) was added to the reaction flask, after 25 min the flask was drained. For peptides containing NTA units. Fmoc-Glu-OtBu (5 equiv, 1.0 mmol) in NMP (5 ml) was added to the reaction flask with HATU (5 equiv, 1.0 mmol) and DIEA (10 equiv, 2.0 mmol), and the flask was agitated for 3 h. The resin was washed with DMF, $CH_2Cl_2$, MeOH, $CH_2Cl_2$, and DMF (3×5 ml each). Piperidine (20% in NMP, 5 ml) was added to the reaction flask, the flask was agitated for 25 min, and the piperidine solution was drained. The resin was washed with DMF, $CH_2Cl_2$, and MeOH (2×5 ml each). The resin was treated with tert-butyl bromoacetate (5 equiv, 1.0 mmol) and DIEA (10 equiv, 2.0 mmol) in NMP (5 ml), and the flask was agitated for 6 h. The resin was washed with DMF and $CH_2Cl_2$ (2×5 ml each). For peptides not containing NTA units. The peptide was acetylated by adding 8.5% DIEA, 5% $Ac_2O$ in NMP (5 ml) to the flask and agitating it for 1 h. The Mtt-protecting group was removed by adding a solution containing 1.8% TFA in $CH_2Cl_2$ (5 ml) to the flask and the flask was agitated for 10 min. The solution was drained and the resin was washed with $CH_2Cl_2$ (2×5 ml each). A fresh deprotection solution was again added to the flask (1.8% TFA in $CH_2Cl_2$) and the procedure was repeated 10 times. For peptide NHbipy. The resin was treated with 4'-methyl-2,2'-bipyridine-4-carboxylic acid (5 equiv, 1.0 mmol), HATU (5 equiv, 1.0 mmol) and DIEA (10 equiv, 2.0 mmol) in NMP (5 ml) and the flask was agitated for 3 h. For peptide NHbiot. The resin was treated with NHS-activated biotin (5 equiv, 1.0 mmol) and DIEA (10 equiv, 2.0 mmol) in NMP (5 ml) and the flask was agitated for 15 h. For peptide NHnbd. The resin was treated with NBD-F (5 equiv, 1.0 mmol) and DIEA (10 equiv, 2.0 mmol) in NMP (5 ml) in the dark and the flask was agitated for 15 h. For the deprotection of all peptides. The resin was washed with DMF, CH$_2$Cl$_2$, MeOH (3×5 ml each). A trifluoroacetic acid (TFA) cocktail solution (95% TFA, 2.5% triisopropylsilane, 2.5% water, 5 ml) was added to the resin, and the mixture was agitated for 2 h. The resulting mixture was filtered and the solution was concentrated in vacuo to remove the TFA. The residue was triturated in cold diethyl ether, the precipitate was collected by centrifugation and dissolved in H$_2$O. The desired peptide was purified to homogeneity by reverse phase HPLC using a Vydac C18 column with an eluent consisting of solvent A (CH$_3$CN/0.1% TFA) and solvent B (H$_2$O/0.1% TFA) with a 60 min gradient consisting of 2 to 30% A, and a flow rate of 8 ml/min ($\lambda_{214\ nm}$ and $\lambda_{254\ nm}$). Purity of the peptides was verified by analytical reverse phase HPLC using a Vydac C18 column with an eluent consisting of solvent A (CH$_3$CN/0.1% TFA) and solvent B (H$_2$O/0.1% TFA) with a 30 min gradient consisting of 2 to 30% A, and a flow rate of 1 ml/min ($\lambda_{214\ nm}$). HPLC retention times: NCoH [21.61 min], NCo [24.67 min], CoH [21.69 min]. Each compound was characterized by MALDI-TOF mass spectrometry. NCoH [M+H]$^+$: 2941.37 (calculated) 2941.66 (found), CoH [M+H]$^+$: 2736.17 (calculated) 2737.98 (found), NCo [M]$^-$: 2665.10 (calculated) 2663.29 (found).

Example

Peptide Synthesis. The collagen-mimetic peptide H-byp, NH$_2$-(Pro-Hyp-Gly)$_4$-(Pro-Lys(Mtt)-Gly)-(Pro-Hyp-Gly)$_4$-COOH, was synthesized by standard solid phase synthesis on a rink amide Chem Matrix resin. In the manual synthesis, 3 equivalents of Fmoc-amino acids were treated with HBTU (3 equiv.) and diisopropylethylamine (DIEA) (2 equiv) in an NMP solution. For the N-terminal acetylation, the resin was treated with acetic anhydride and DIEA in DMF for 1 hr. The Mtt protecting group was removed using as described above using 1.8% TFA in DCM. The resin was treated with 2,2'-bipyridine-4,4'-carboxylic acid (3 equiv.), HBTU (3 equiv.), and DIEA (3 equiv.) in NMP. The peptide was cleaved from the resin by treatment for 2 h with TFA/TIPS/H$_2$O (95:2.5:2.5), followed by precipitation with diethyl ether.

Example

HPLC Purification. The crude H-byp peptide was purified by reverse phase (RP)HPLC on a Jupiter (21.2×250 mm, 10μ particle size, 300 Å pore size, Phenomenex) column. The peptide was eluted at 50° C. with a linear gradient of acetonitrile in water both containing 0.05% TFA. The gradient conditions were 2-25% acetonitrile over 40 min, and the eluent was monitored at 214 nm. Purity was determined by reverse phase analytical HPLC from a Jupiter (4.6×250 mm, 5μ particle size, 300 Å pore size, Phenomenex) column at 50° C., and showed a single major peak.

Example

Mass Spectroscopy Analysis. MALDI-TOF mass spectrometric measurements were performing on an Applied Biosystems Voyager—DE MALDI-TOF, and H-byp was prepared in an α-cyano-4-hydroxycinnamic acid matrix. MALDI-TOF mass spectrum (m/z): [M+Na]$^+$: 2697.25 (calculated) 2695.25 (observed).

Example

Figure 23:
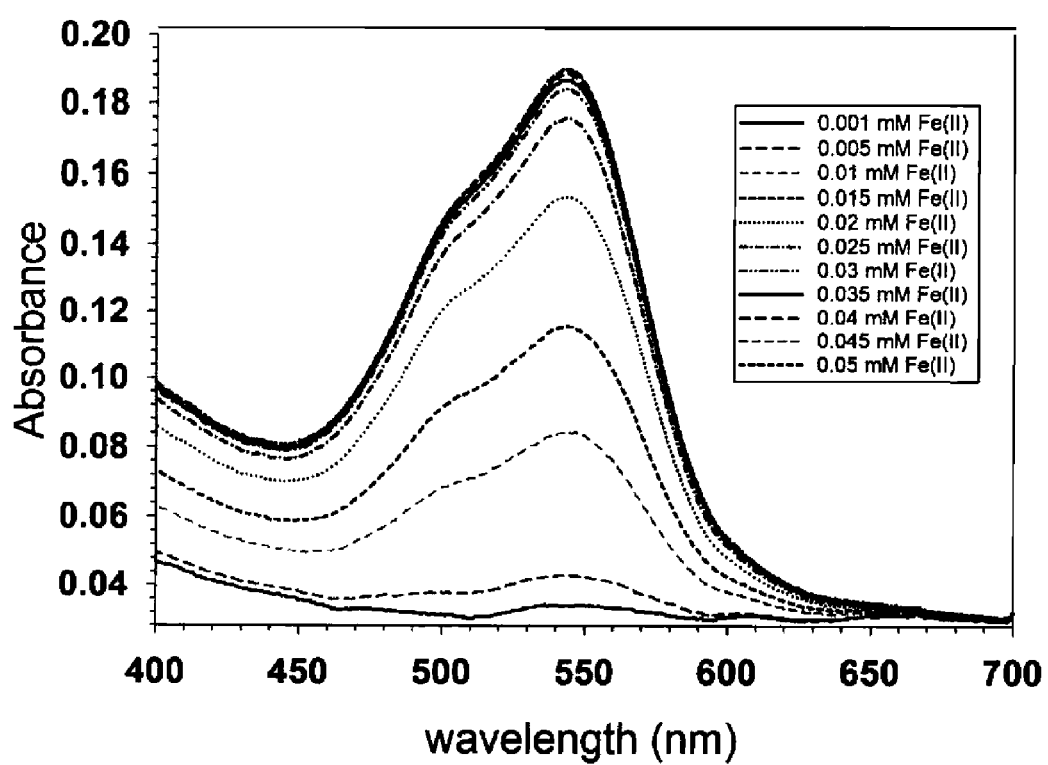
FIG. 23. UV-Vis spectra of titrated H-byp (54 μM) with Fe(II).
Figure 24:
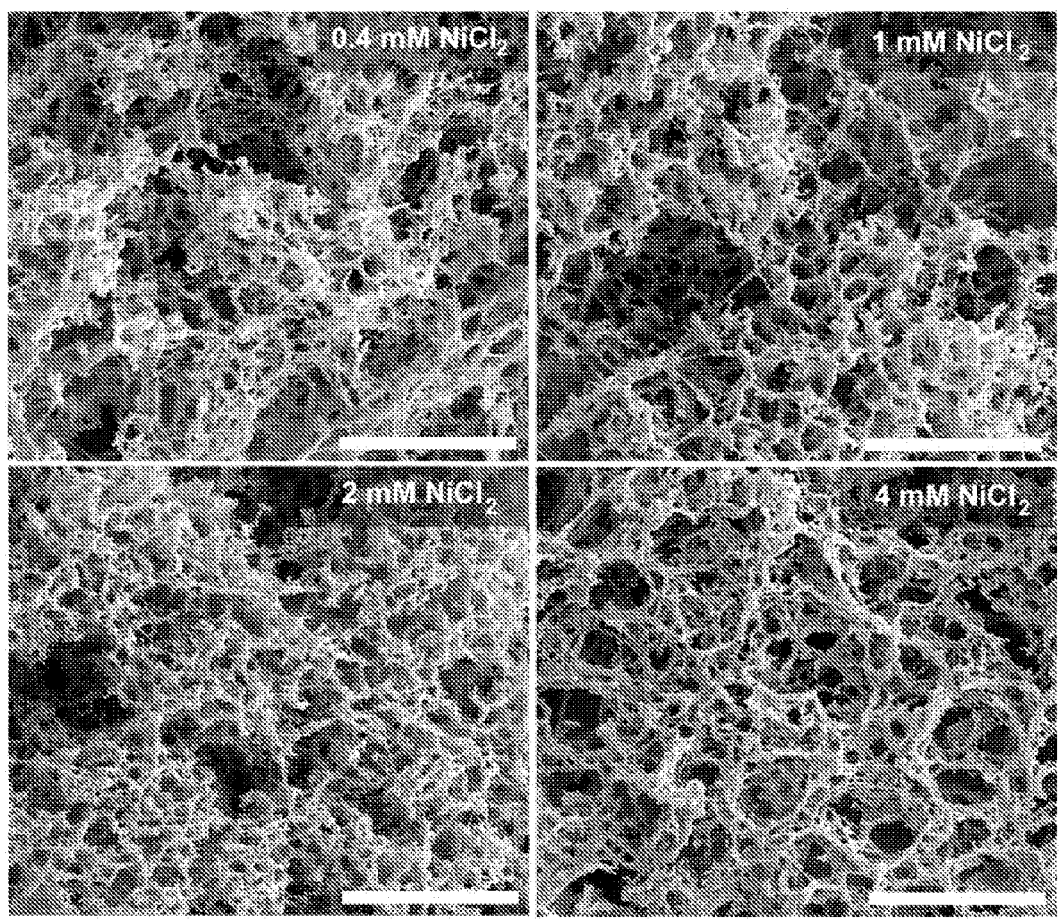
FIG. 24. Effect of metal ion concentration on scaffold morphology. SEM images of NHbipy peptide (1 mM) with various concentration of NiCl$_2$ were obtained (scale bar 10 μm).
Figure 25:
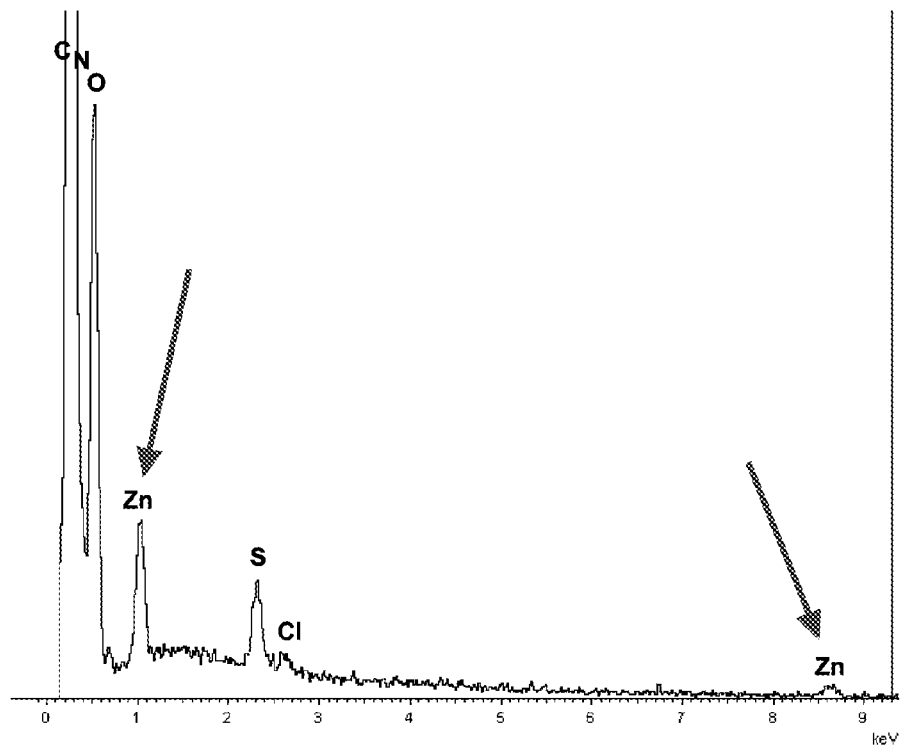
FIG. 25. Energy Dispersive X-Ray analysis of NCoH particles. EDX analysis revealed the presence of zinc(II) metal ions in particles assembled from NCoH and ZnCl$_2$ (top) and the presence of copper (II) metal ions in particles assembled from NCoH and CuCl$_2$ (bottom).
Figure 25:
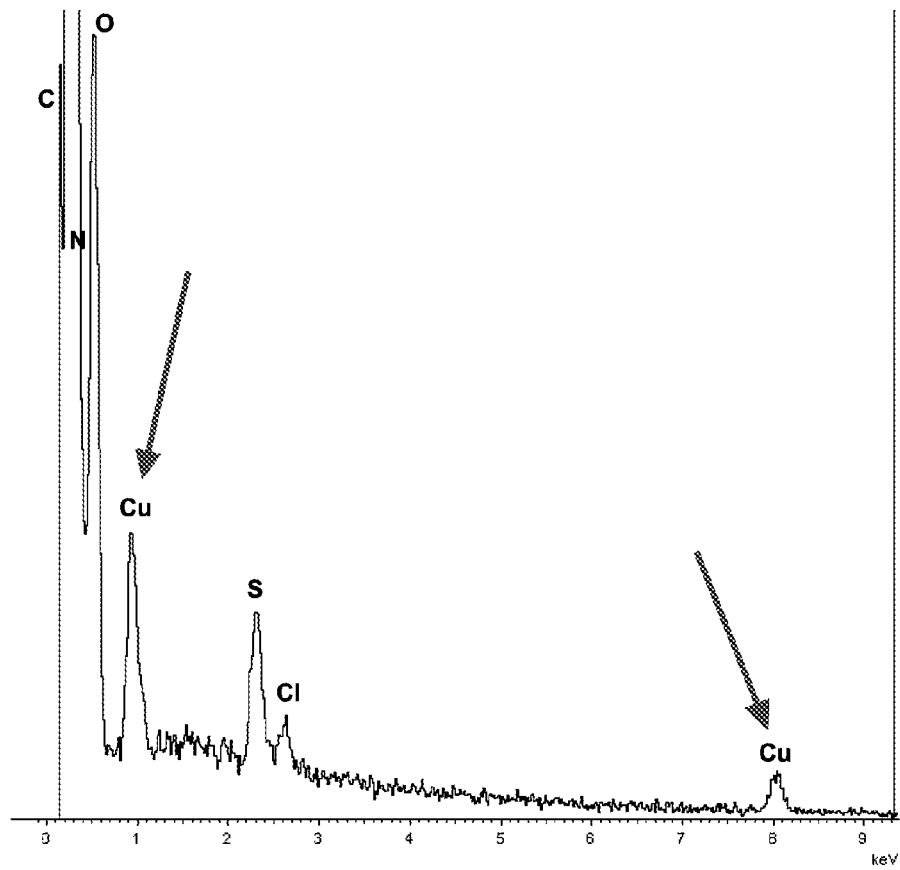
Figure 26:
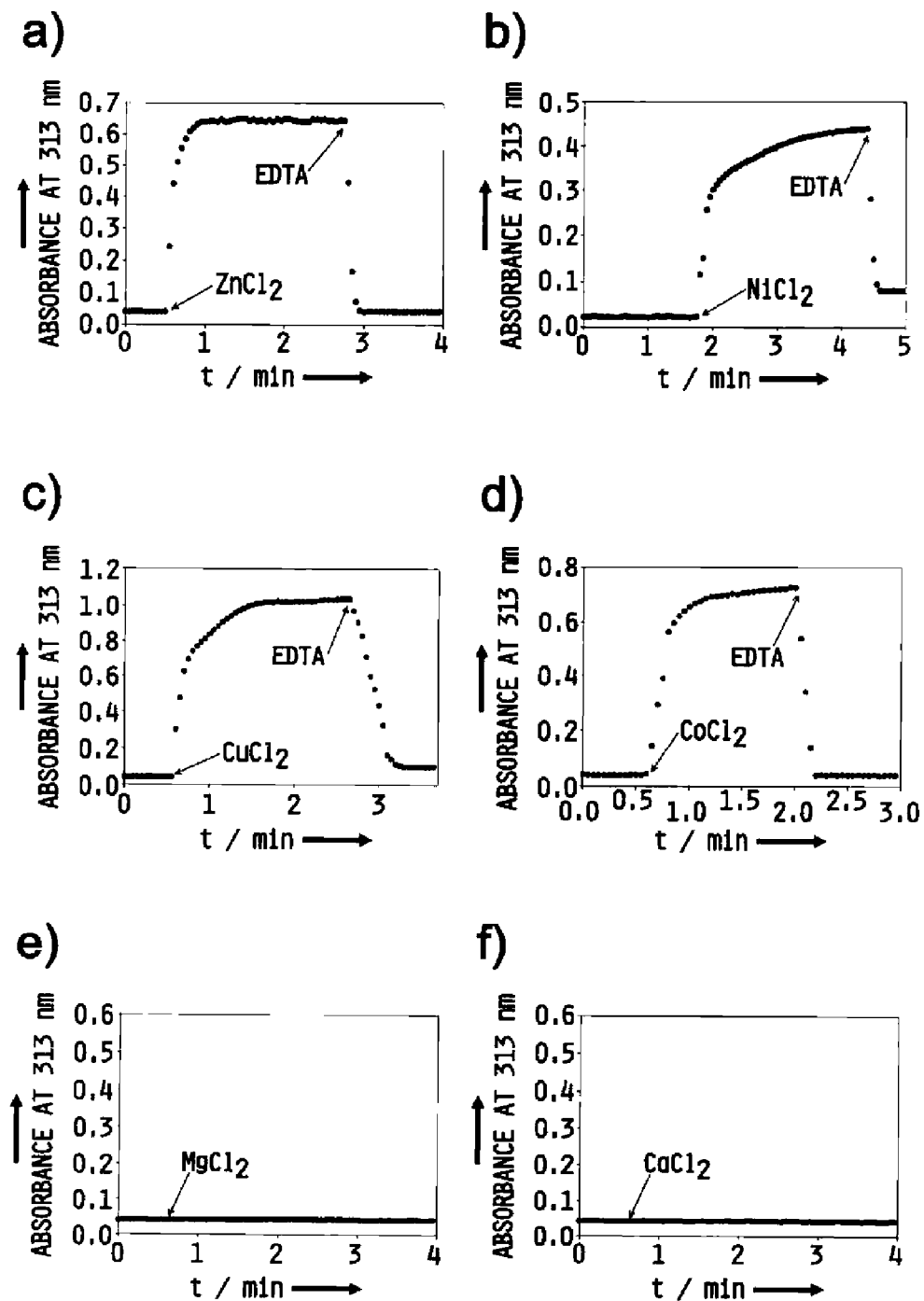
FIG. 26. Turbidity experiments using peptide NCoH. Solution turbidity was monitored by measuring optical intensity at 313 nm for solutions containing NCoH (125 μM) in 20 mM MOPS pH 7.4 and 1 mM of ZnCl$_2$ (a), NiCl$_2$ (b), CuCl$_2$ (c), CoCl$_2$ (d), MgCl$_2$ (e), and CaCl$_2$ (f).
Figure 27:
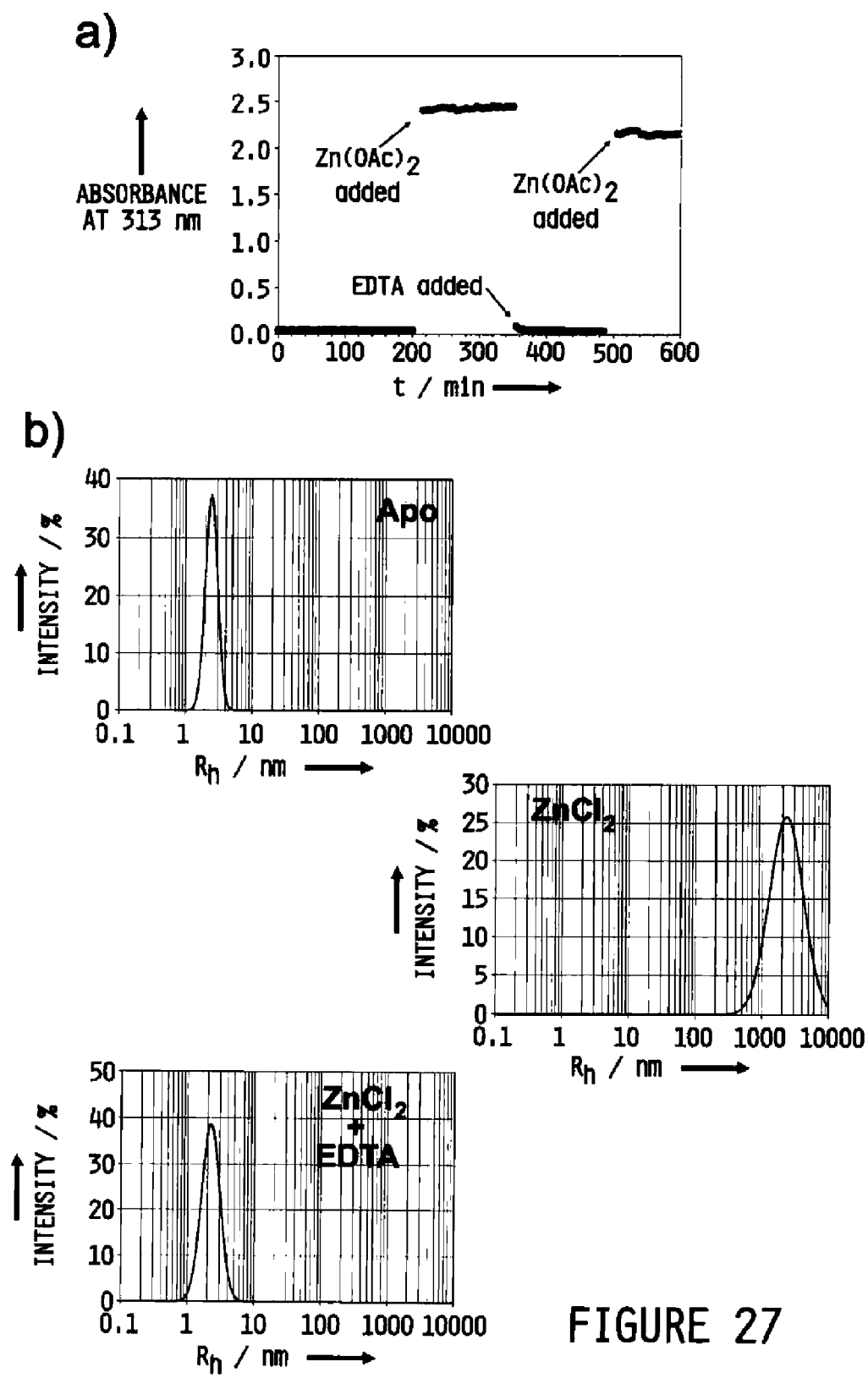
FIG. 27. Reversibility of solution turbidity. a) Solution turbidity was monitored by measuring optical intensity at 313 nm for solutions containing NCoH (250 μM) in 20 mM MOPS pH 7.4 and 1 mM of Zn(OAc)$_2$. At the specified time intervals, EDTA was added (10 mM final concentration), followed by the addition of Zn(OAc)$_2$ again (final concentration 3 mM). b) Dynamic light scattering analysis of chelation competition experiments using the NCoH peptide. Hydrodynamic radius measurements were obtained using 200 μM of peptide with 100 μM of ZnCl$_2$ in 20 mM MOPS (pH 7.4) followed by the addition of EDTA (10 mM final concentration).
Figure 28:
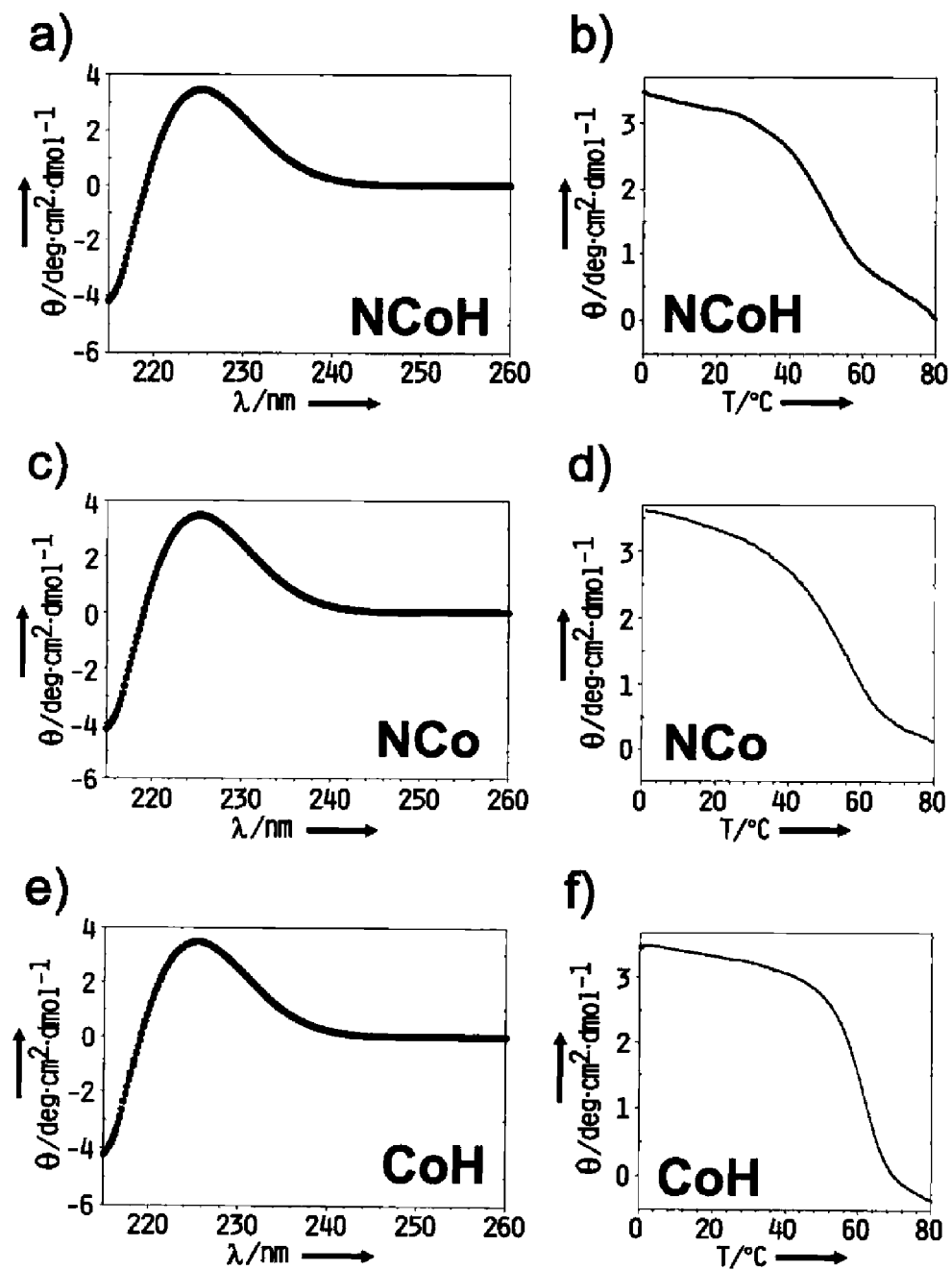
FIG. 28. Circular dichroism spectroscopy analysis of NCoH, NCo, and CoH. CD spectroscopy of specified peptides were measured at 4° C. [500 μM peptide concentration, 20 mM MOPS, pH 7.4] (a, c, e). Thermal denaturation of peptide triple helix formation was monitored at 225 nm between 0° C. to 80° C. (b, d, f).
Figure 29:
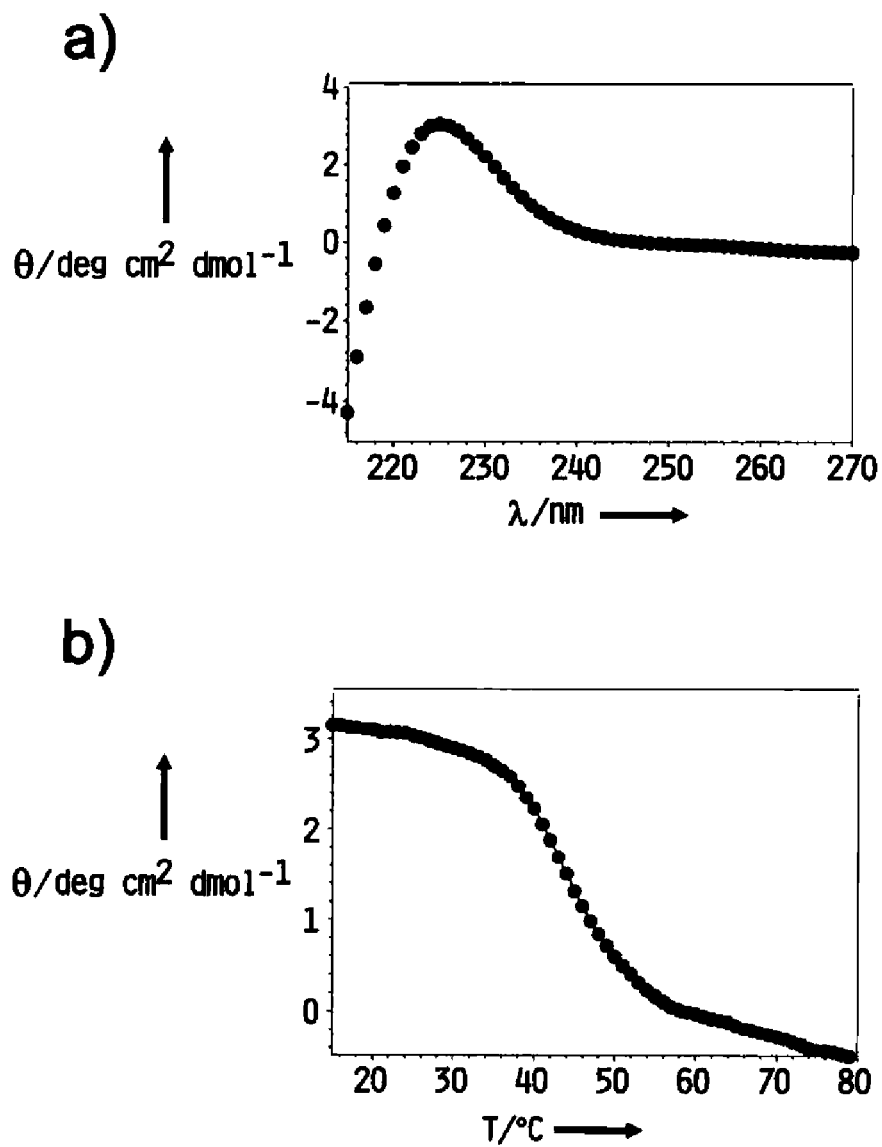
FIG. 29. a) CD spectrum of NHbipy (250 μM) was measured at 4° C. in 20 mM phosphate buffer. b) Thermal denaturation of triple helix was monitored at 225 nm from 0 to 85° C. c) Visualization of solution turbidity upon addition of NiCl$_2$ (2 mM) to a solution containing NHbipy (1 mM). The addition of EDTA (5 mM) causes the disappearance of the turbidity.
Figure 30:
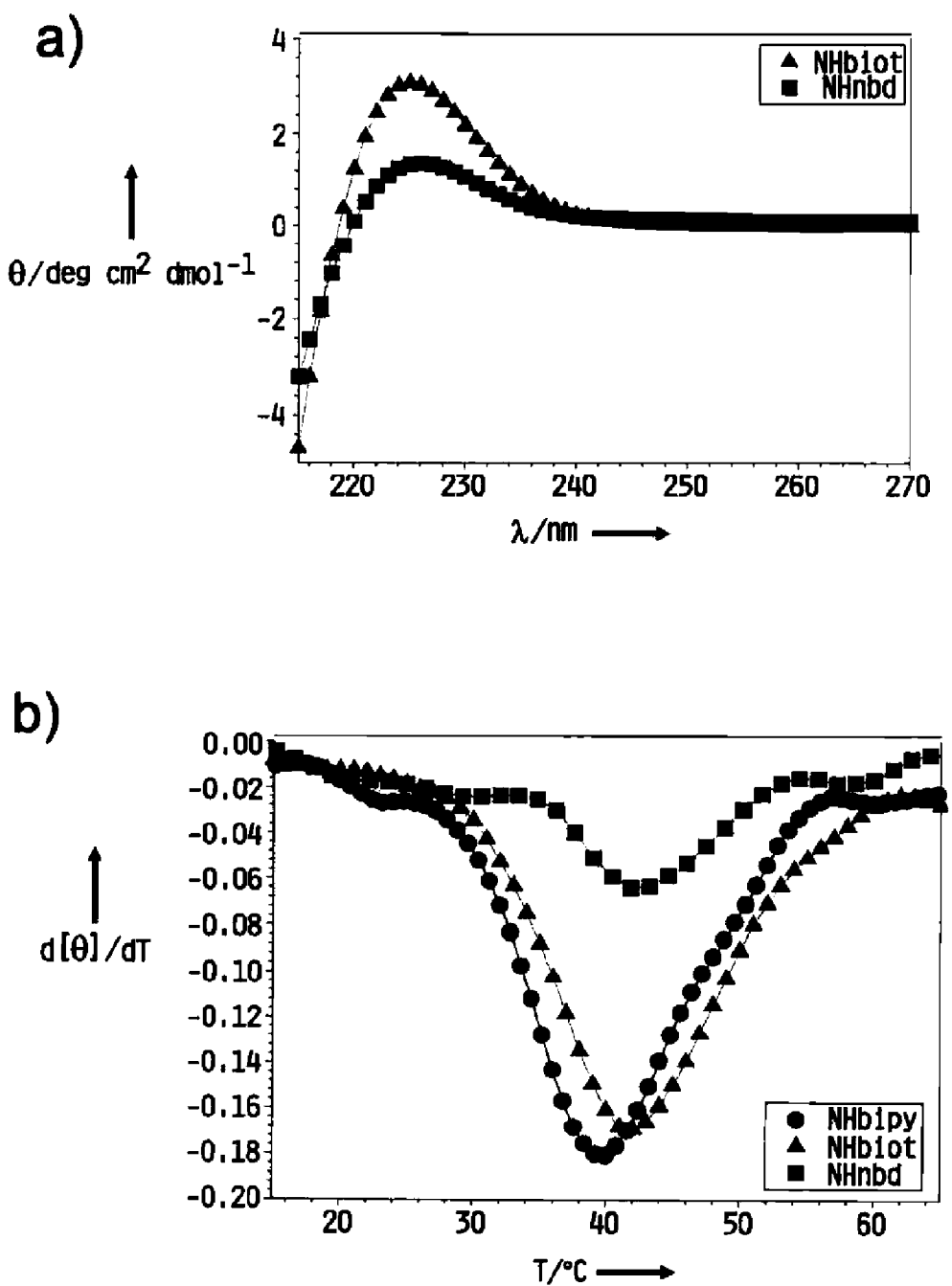
FIG. 30. a) CD spectroscopy of NHbiot and NHnbd were measured at 4° C. and both were found to possess a polyproline type II signature profile. b) Thermal denaturation of the specified peptide triple helix formation was monitored at 225 nm between 0° C. to 85° C.
Figure 31:
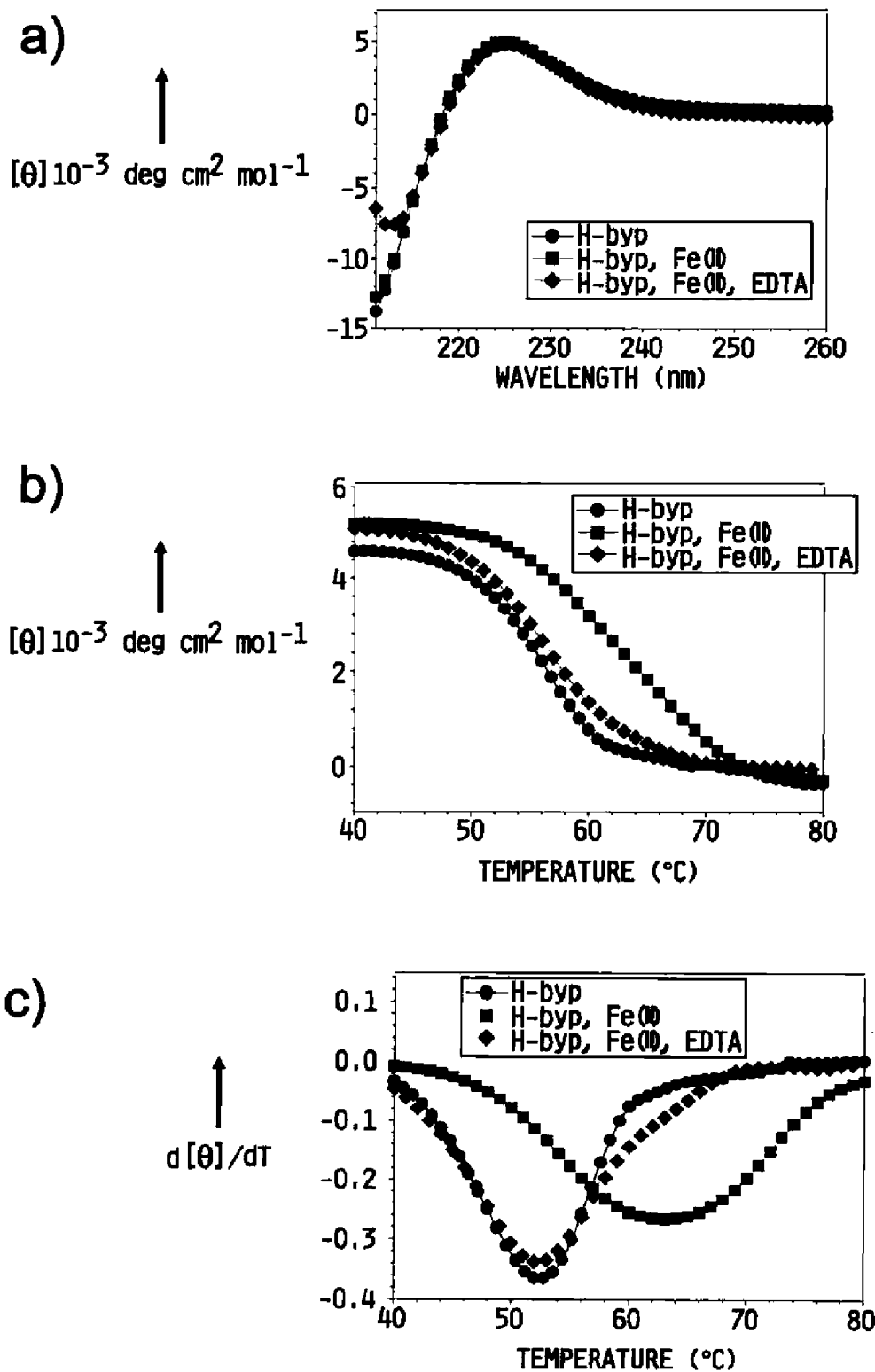
FIG. 31. Circular dichroism spectroscopy, thermal denaturing spectroscopy, and first derivative d[θ]/dt of the melting curve. (a) CD spectroscopy of H-byp (250 μM) in 10 mM HEPES pH 7.0 (black), Fe(II) (125 μM) (red), and EDTA (100 mM) (green). (b) Thermal denaturing curves of H-byp (250 μM) in 10 mM HEPES pH 7.0 (black), Fe(II) (125 μM) (red), and EDTA (100 mM) (green). (c) First derivative d[θ]/dT of the melting curve. H-byp 250 μM (black), with Fe(II) 125 μM (red), and Fe(II) 125 μM with EDTA 100 mM (green).
Figure 32:
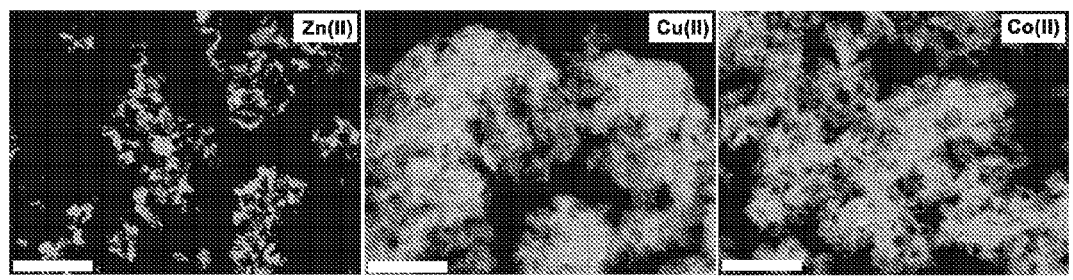
FIG. 32. Visualization of cell encapsulation within the NHbipy/NHnbd matrices. Fluorescence microscopy visualization of HeLa cells encapsulated within the NHbipy/NHnbd-matrix using the specified metal ions (scale bar=200 μm).
Figure 33:
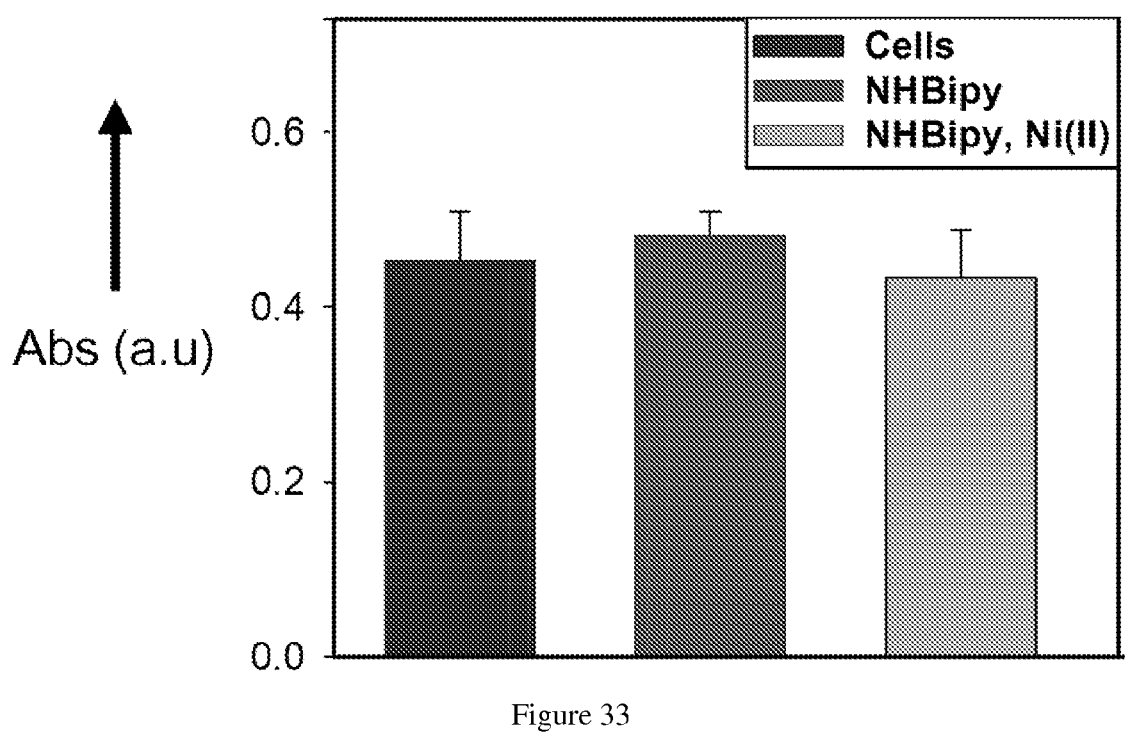
FIG. 33. Cellular viability was determined using the colorimetric MTS assay. HeLa cells were either plated on a standard cell culture plate without added NHbipy in solution, or encapsulated in a NHbipy scaffold triggered by NiCl$_2$ followed by a 48 h incubation at 37° C. MTS analysis shows that cells remained as viable when encapsulated in the scaffolds as when they are cultured using standard cell culture plates.
Figure 34:
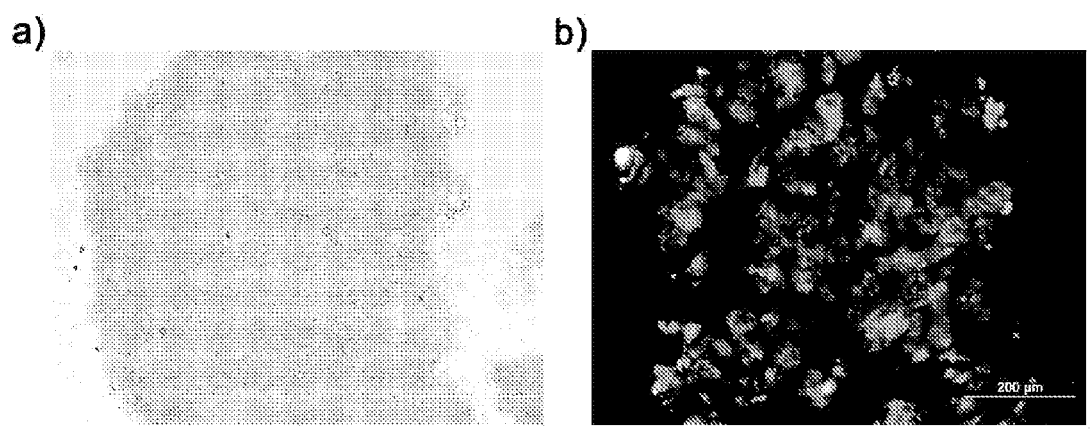
FIG. 34. Cellular viability verification of encapsulated cells. HeLa cells were encapsulated in a NHbipy-scaffold after the addition of NiCl$_2$. Following a 48 h incubation at 37° C., cellular viability was assessed by staining cells with calcein-AM. Bright field (a) and fluorescence (b) microscopy analysis demonstrated that cells remained viable for the duration of the incubation period (scale bar=200 μm).
Figure 35:
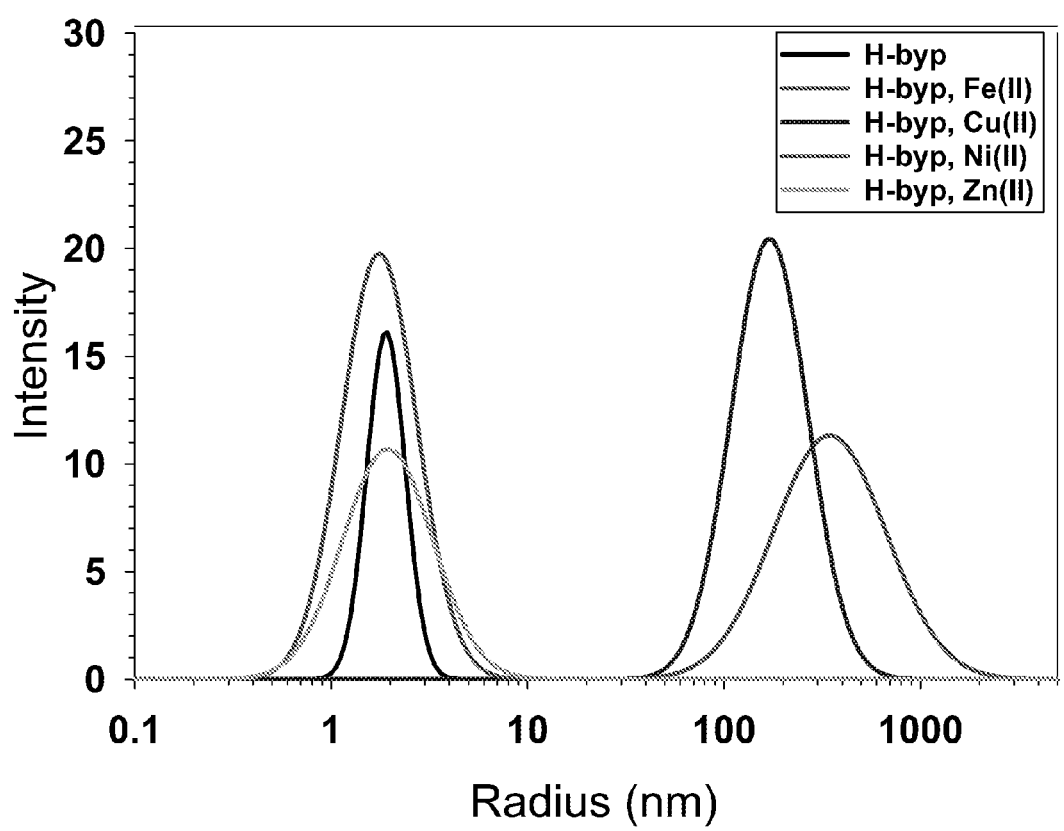
FIG. 35. DLS of H-byp (1 mM) (black) with 1 mM Fe(II) (red), 1 mM Cu(II) (blue), 1 mM Ni(II) (green), 1 mM Zn(II) (yellow).
Figure 36:
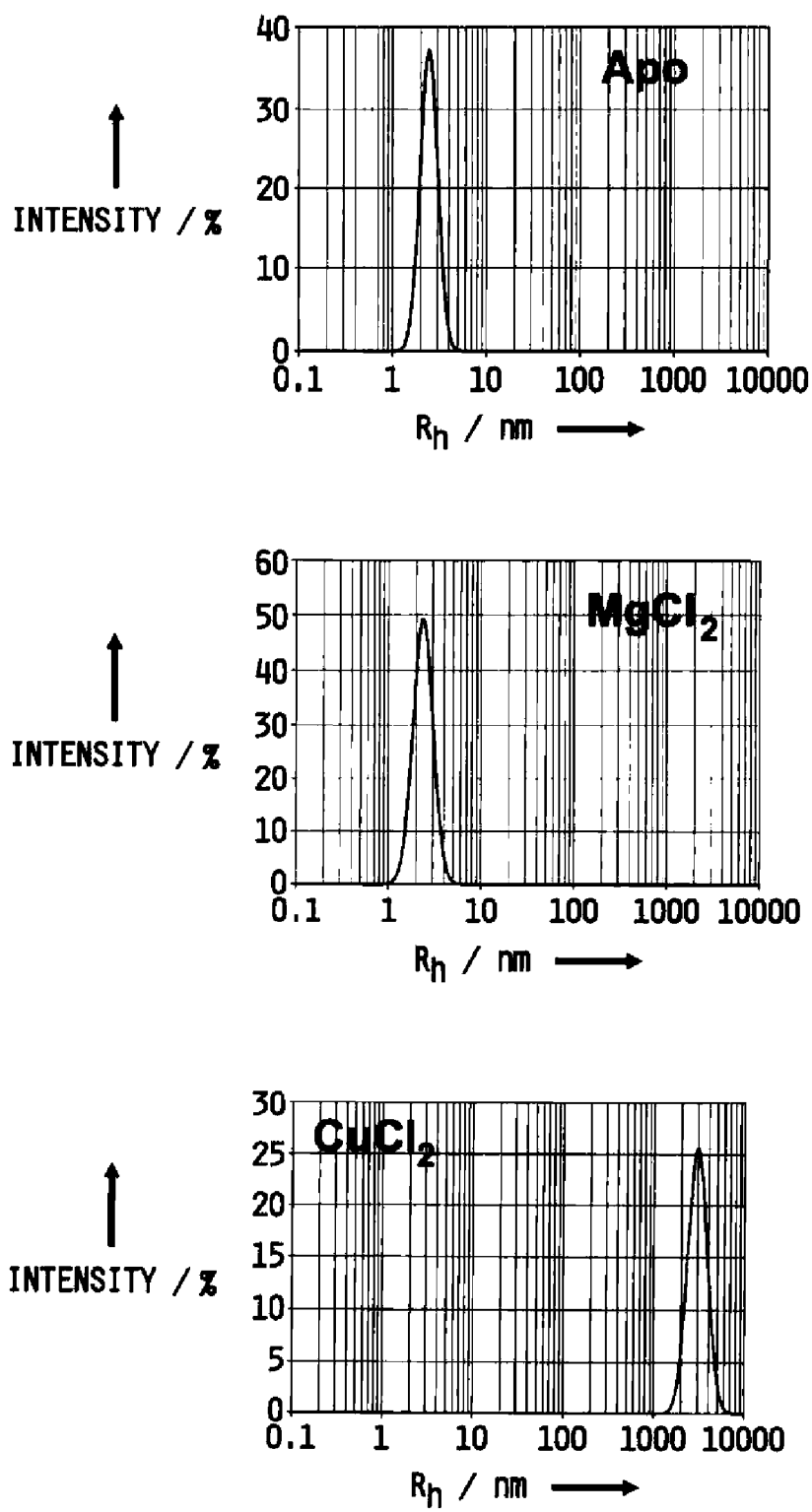
FIG. 36. Dynamic light scattering analysis of a metal screen using the NCoH peptide. Hydrodynamic radius measurements were obtained FIG. 37. Dynamic light scattering analysis of control peptides NCo and CoH. Hydrodynamic radius measurements were obtained using 200 μM of peptide with 100 μM of CuCl$_2$ in 20 mM MOPS (pH 7.4).
Figure 36:
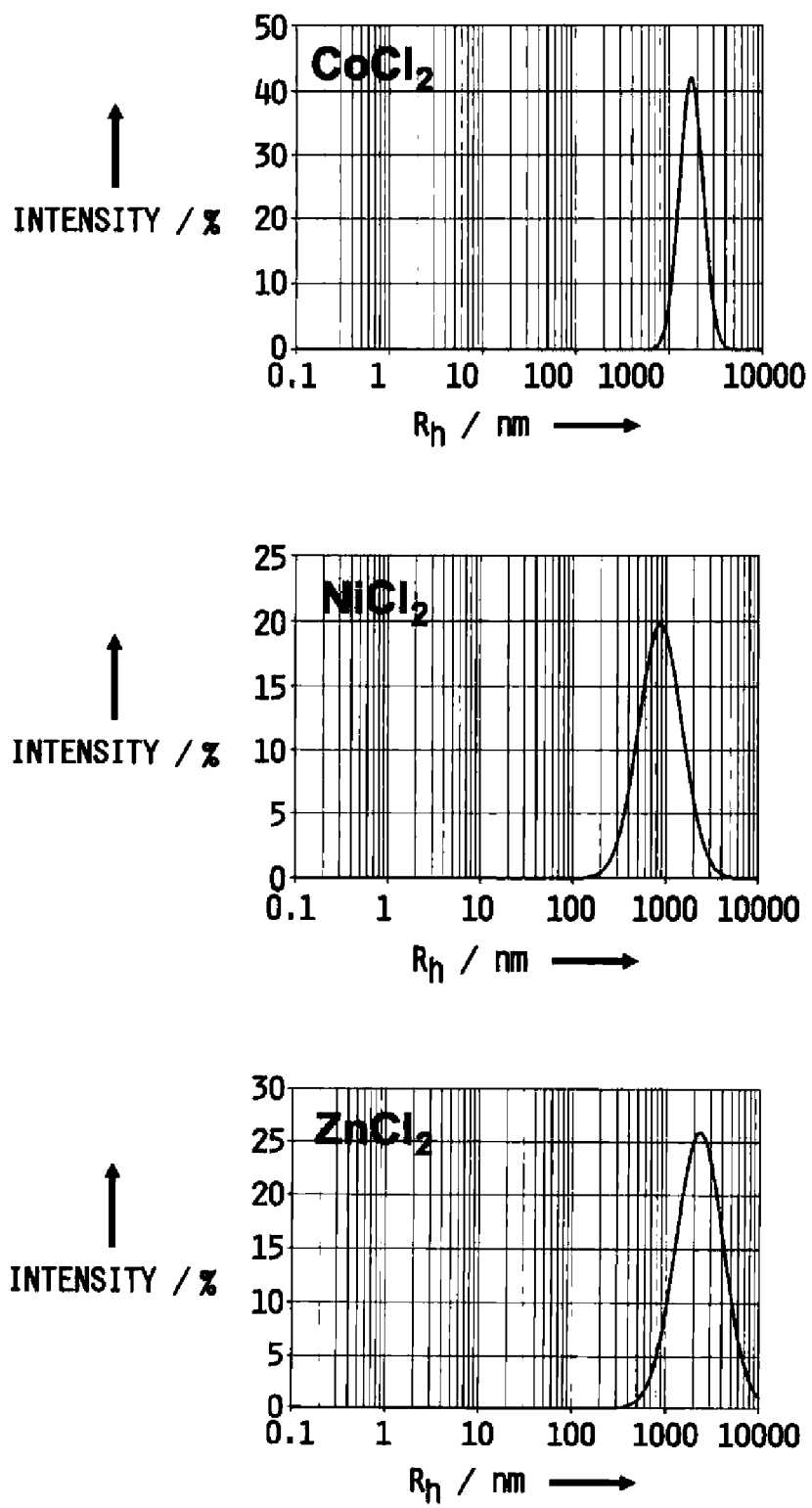
Figure 37:
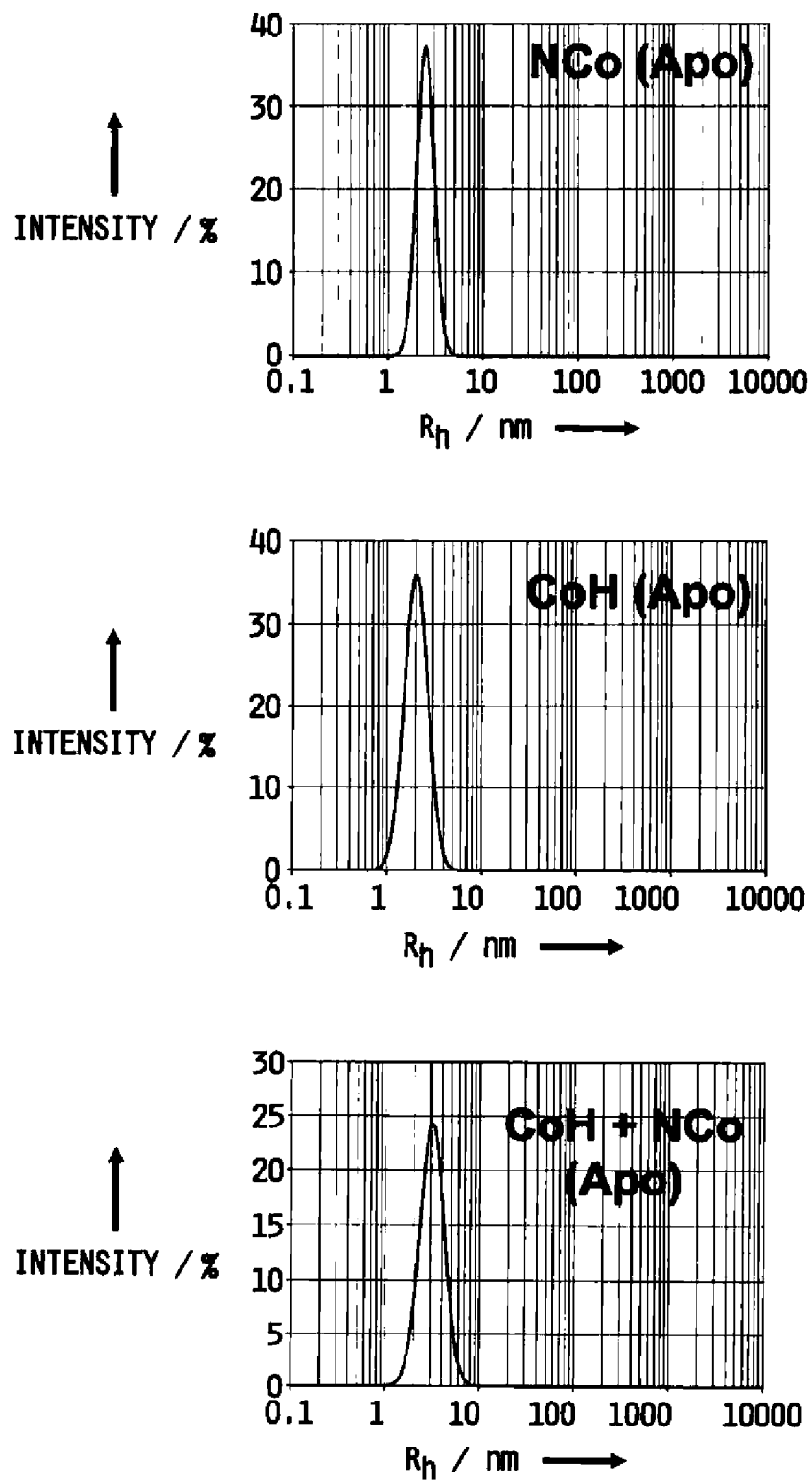
Figure 37:
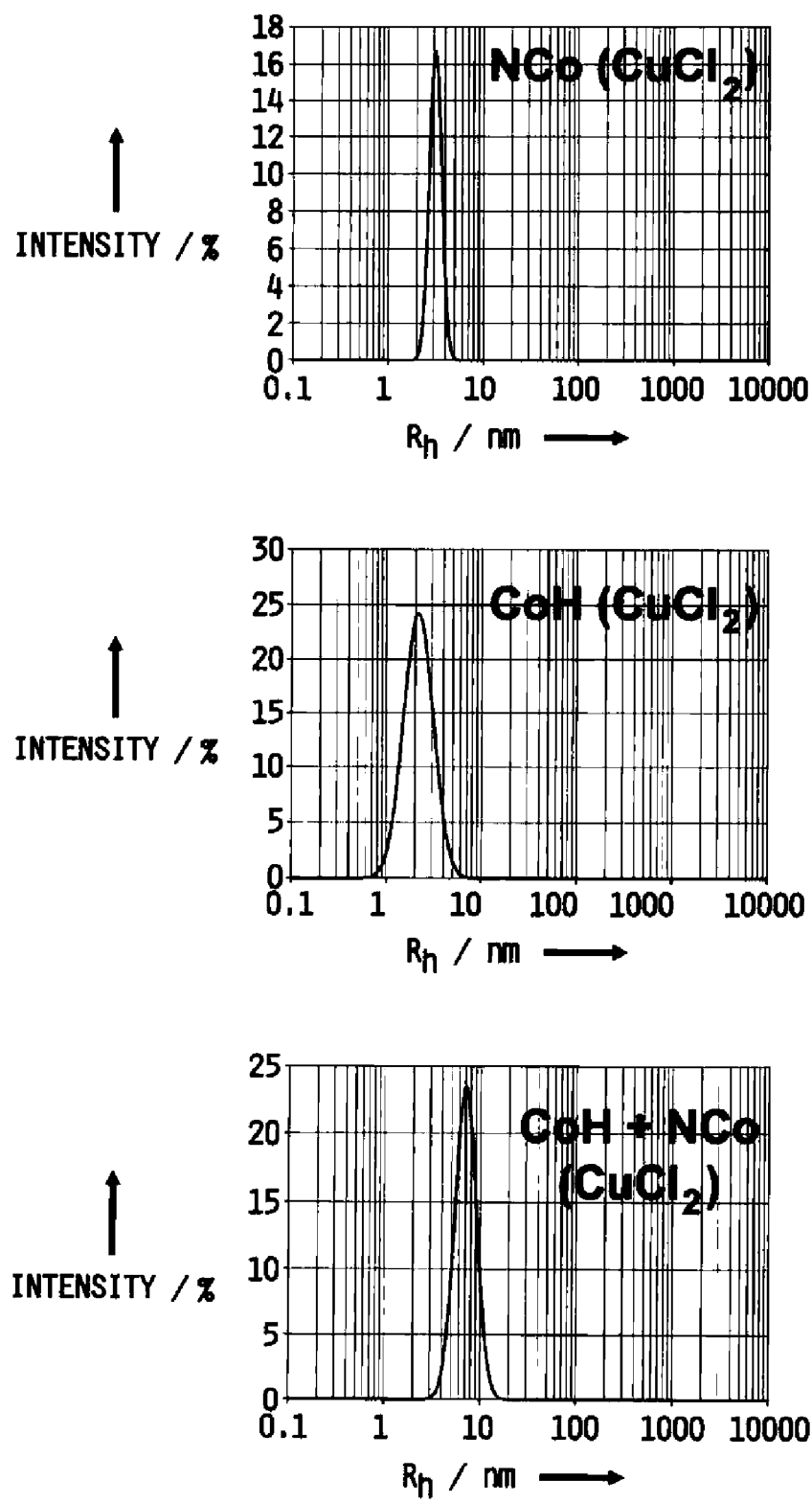
Figure 38:
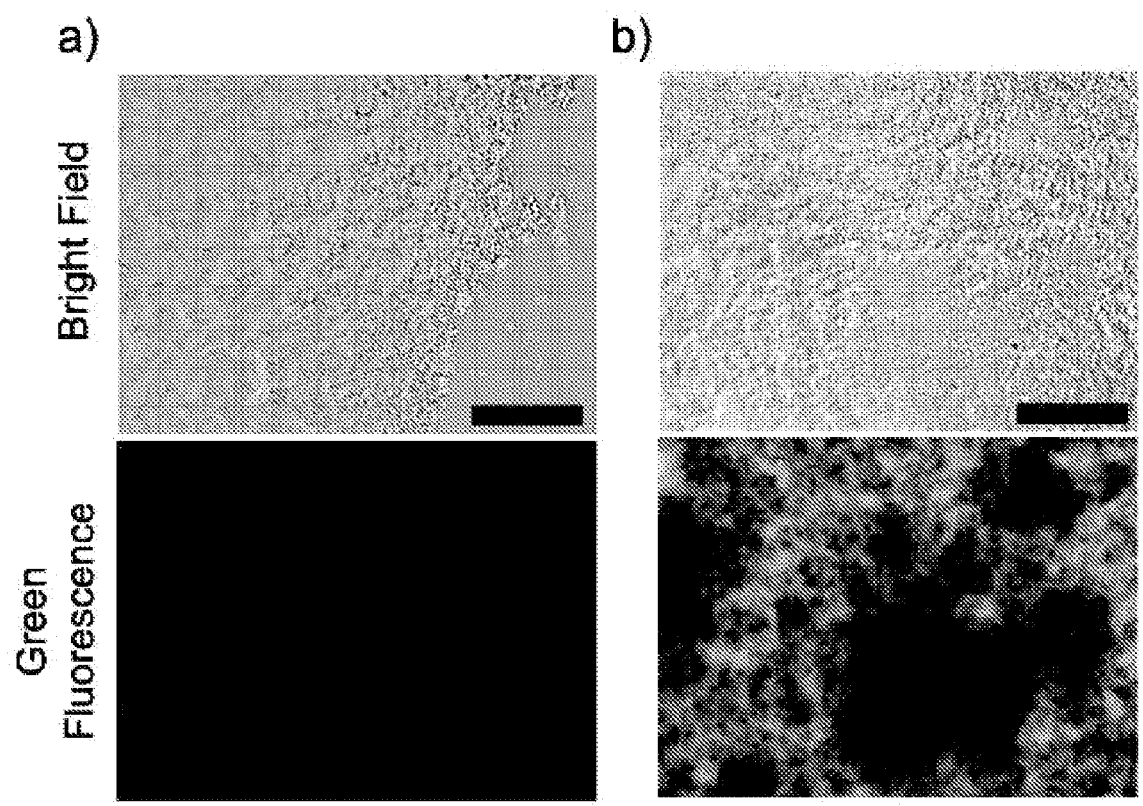
FIG. 38. Visualization of incorporation of NHnbd into an NHbipy-scaffold. a) A solution composed of NHbipy (1 mM) was triggered using 1 mM of NiCl$_2$. b) A solution composed of NHbipy (1 mM) and NHnbd (20 μM) was triggered using 1 mM of NiCl$_2$ Following thorough washing of the scaffold, dried matrices were visualized (scale bar=200 μm).

UV-Vis spectra. Titration experiments were performed on a Cary 300 UV-Vis spectrophotometer, Varian. For the titration of the H-byp-Fe(II) complex, a solution of H-byp (0.05 mM) was added with various concentrations of Fe(ClO$_4$)$_2$. The absorbance max at 540 nm was plotted vs. the molar ratio of Fe(II) to H-byp. (FIG. 23). UV-vis titration may be used confirm the presence of a complex between the peptide and the metal ion, and also to determine the binding stereochemistry. It has previously been established that the metal to ligand charge transfer resulting from the binding of bipyridine with Fe(II) generates an absorbance maximum of 540 nm (Lever, A. B. P. Inorganic Electronic Spectroscopy; Elsevier Publishing Co.: New York, (1968)). The addition of Fe(II) to a H-byp solution (54 μM) generated a magenta solution with a maximum absorbance at 540 nm. A maximum absorbance was observed at a relative molar ratio of 1:3 Fe(II):H-byp, consistent with the bidentate coordination of bipyridine to octahedral Fe(II).

Examples

The following compounds were prepared from the corresponding starting materials using the methods described herein.

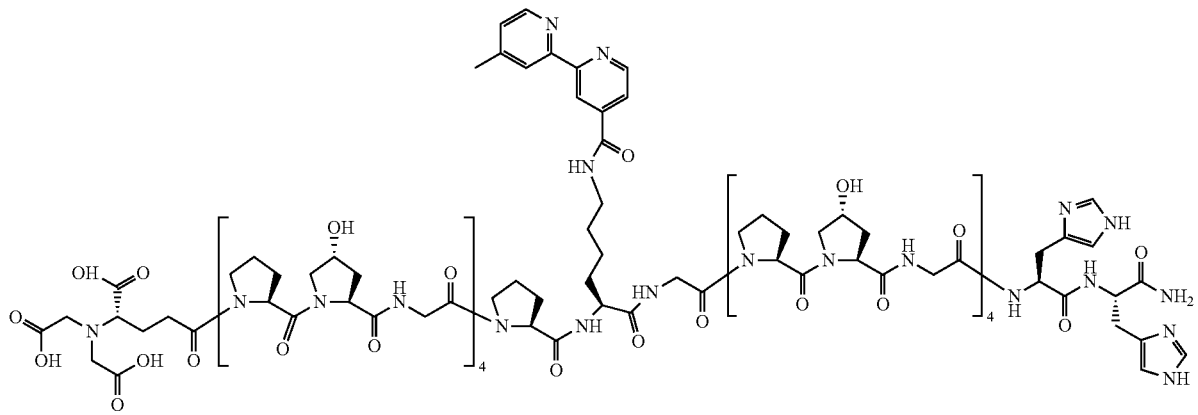

MALDI-TOF mass spectrometry. NHbipy [M+H]$^+$: 3152.5 (calculated) 3153.2 (found).

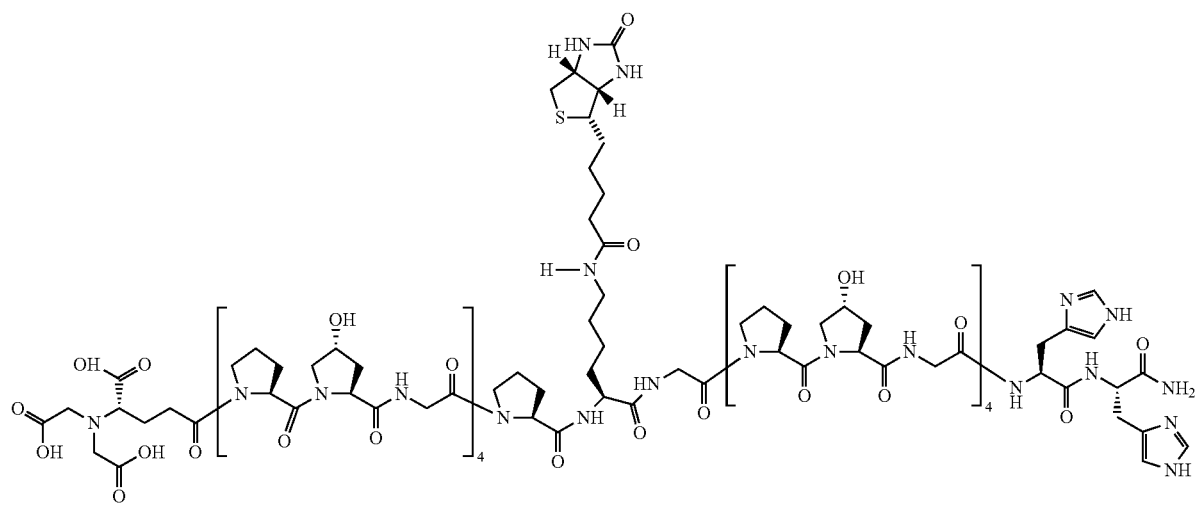

MALDI-TOF mass spectrometry. NHbiot [M+H]$^+$: 3182.5 (calculated) 3181.9 (found).

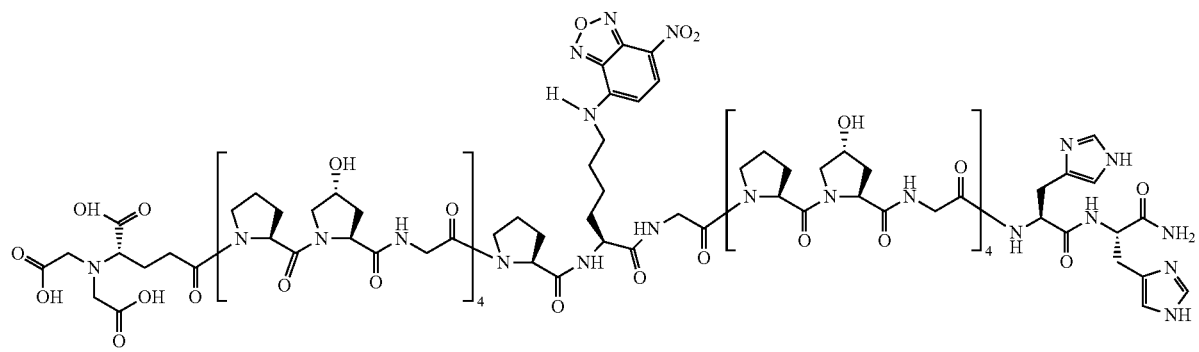

MALDI-TOF mass spectrometry. NHnbd [M+H]$^+$: 3119.3 (calculated) 3119.8 (found).

Example

Transmission Electron Microscopy. H-byp (2 mM, 6 μL) in HEPES (10 mM, pH 7.0) was heated for 15 min at 70° C. The solution was cooled to 25° C. followed by the addition of Fe(ClO$_4$)$_2$ (0.3 mM, 15 μL) and was allowed to incubate at 20° C. for 48 h. The solutions were floated on a 400 mesh carbon grid and negatively stained with phosphotungstic acid (PTA). Samples were imaged using a Philips CM-100 TEM operated at 80 kv, 200 μM condenser aperture, and 50 μm objective aperture. Images were captured on a Kodak SO-163 electron image film.

Example

Scanning Electron Microscopy Imaging and Energy Dispersive X-Ray Analysis. Scanning electron microscopy images of collagen particles were obtained using a FEI NOVA nanoSEM high resolution FESEM (FEI Company, Hillsboro Oreg.) using the Helix low vacuum detector (0.98 T) with operating parameters of 10 kV. Solutions composed of peptides (e.g., NHbipy) (1 mM) in MOPS buffer (20 mM, pH 7.4) were incubated with desired concentration of the metal ions. Following the aggregation of the particles, all solutions were spun at 10,000 g for 3 min and the supernatant was carefully removed. Particles were resuspended in distilled water, and droplets of the sample (5 μl) were air-dried onto glass cover slips. The dried samples were sputter-coated with AuPd (3 min) prior to imaging. Energy Dispersive X-ray (EDX) analysis was performed using particles described above except that particles were dried on carbon tape instead of glass cover slips. Measurements were obtained with an OXFORD INCA 250 electron dispersive X-ray detector (EDX) operated conjunctly with the FEI NOVA nanoSEM.

Example

Cryo-Scanning Electron Microscopy Imaging. HeLa cells (50,000 cells) in DMEM were added to an eppendorf tube containing NHbipy (1 mM) and phosphate buffer (20 mM, 7.4). Scaffold aggregation was triggered by the addition of Ni$^{II}$ (1 mM) and the encapsulated cells were incubated at 37° C. with 5% CO$_2$ for 24 h. The collagen scaffolds were deposited on the surface of a three-hole sample holder, and the media was wicked away. The sample was plunged into a liquid nitrogen slush to freeze. A vacuum was pulled and the sample was transferred to the Gatan Alto 2500 pre-chamber (cooled to ~170° C.). After fracturing the sample with a cooled scalpel to produce a free-break surface, the samples were sublimated at −85° C. for 20 min followed by sputter coating for 120 sec. with platinum. The sample was then transferred to the microscope cryo-stage (~-130° C.) for imaging. Samples were imaged with a FEI NOVA nano SEM field emission SEM (FEI Company, Hillsboro, Oreg.) using the TLD (Through-the-Lens) or ET (Everhart-Thornley) detector operating at 5 kV accelerating voltage.

Example

Atomic Force Microscopy Imaging. Samples were prepared as above and droplets of the sample (5 µl) were air-dried onto freshly cleaved mica disks. Collagen particles were imaged in tapping mode on a Multimode AFM with Nanoscope IIIa controller (Veeco) using oxide-sharpened silicon probes having a resonance frequency in the range of 280-320 kHz (MikroMasch-NSC15). The tip-surface interaction was minimized by optimizing the scan set-point to the highest possible value.

Example

Turbidity Experiments. Turbidity experiments were performed by monitoring UV-absorbance in a 1 ml quartz cuvette. Turbidity formation was monitored by measuring absorbance at 313 nm from a solution containing NCoH peptide with various metals in 20 mM MOPS buffer, pH 7.4.

Example

Circular Dichroism. NHbipy. CD wavelength scan spectra were recorded on a Jasco circular dichroism spectropolarimeter (Model J810) at 4° C. using a 0.1 cm path length quartz cell. The spectra were averaged over three scans taken from 300 to 215 nm with a resolution of 0.2 nm at a scan rate of 100 nm/min. The CD data obtained were processed to convert the data from degrees of rotation to mean residue ellipticity by dividing by the appropriate path length, peptide concentration, and number of residues in the peptide. Thermal stability of peptides was determined by measuring the mean residue ellipticity at 225 nm. Temperature was varied from 4° C. to 90° C. at 6° C./h for solutions containing specified peptides (200 µM) in 20 mM phosphate buffer, pH 7.4.

Circular Dichroism. NCoH. CD wavelength scan spectra were recorded on a Jasco circular dichroism spectropolarimeter (Model J810) at 25° C. using a 0.1 cm path length quartz cell. The spectra were averaged over three scans taken from 260 to 210 nm with a resolution of 0.1 nm at a scan rate of 50 nm/min. The CD data obtained were processed to convert the data from degrees of rotation to mean residue ellipticity by dividing by the appropriate path length, peptide concentration, and number of residues in the peptide. Thermal stability of peptides was determined by measuring the mean residue ellipticity at 225 nm. Temperature was varied from 0° C. to 80° C. at 6° C./h for solutions containing specified peptides (500 µM) in 20 mM MOPS buffer, pH 7.4.

Circular Dichroism Spectroscopy. H-byp. CD spectra were obtained on a JASCO J-810 CD spectropolarimeter (Jasco inc., Easton, Md.) equipped with a PFD-425S Peltier temperature control unit. Peptide solutions H-byp (250 µM) were prepared in a HEPES buffer (10 mM, pH 7.0) and heated to 70° C. for 30 min. After cooling to 25° C. a $Fe(ClO_4)_2$ (125 µM) was added and allowed to incubate at 20° C. for 48 h. The spectra were acquired at 4° C., averaging 3 scans between 211-280 nm at 0.2 nm data pitch with a 2 nm bandwidth. The scan rate was 100 nm/min$^{-1}$ with a 2 second response time. CD melting curves were generated by monitoring at 225 nm, while the temperature increased (6° C./h) from 4 to 90° C. with a 0.2 nm data pitch and a 2 nm bandwidth. The Tm values were determined from the first derivative $d[\theta]/dT$ of the melting curve.

Example

Dual Metal Loading Fluorescence Microscopy. For fluorescence microscopy images of ruthenium/nickel dual metal ion system, NHbipy (1 mM), $R^{III}$ (10 mM), and phosphate buffer pH 7.4 (20 mM) was heated to 90° C. for 3 h followed by 6 h at 4° C. to allow for triple helix formation. Metals $Co^{II}$, $Cu^{II}$, and $Zn^{II}$ (1 mM) were added to the solutions and allowed to stand at room temperature for 24 h. Solutions were spun at 10,000 g for 3 min and the supernatant was carefully removed. To the remaining pellet was added 100 µl of 20 mM phosphate buffer pH 7.4, the solution was vortexed for 20 s, and the epperdorf tube was once again spun down at 10,000 g for 3 min. The supernatant was carefully removed; the pellet was resuspended in 20 µl of 20 mM phosphate buffer pH 7.4, and plated onto a glass slide. Images were captured using an Optical Microscope Olympus BX51 equipped with a CCD camera. Fluorophore was excited using a U-MWG2 filter with excitation of 510-550 nm and the fluorescence emission was collected using a 590 nm filter. A transmission image was also collected to show scaffold morphology.

Example

Streptavidin Binding Fluorescence Microscopy. To initial self assembly, $NiCl_2$ (2 mM final concentration) was added to solutions composed of NHbipy and NHbiot at various ratios (1 mM total concentration of peptide) in 20 mM phosphate buffer pH 7.4 at room temperature. After incubating for 30 min, solutions were spun at 10,000 g for 3 min and the supernatant was carefully removed. To the remaining pellet was added 100 µl of 20 mM phosphate buffer pH 7.4, the solution was vortexed for 20 s, and the eppendorf tube was once again spun down at 10,000 g for 3 min. The supernatant was carefully removed. The pellet was resuspended in 50 µl of 20 mM phosphate buffer pH 7.4 containing 70 µM of FITC-labelled streptavidin. The solution was allowed to stand in the dark for 2 h at room temperature. The solutions were spun at 10,000 g for 3 min and the supernatant was carefully removed. To the remaining pellet was added 100 µl of 20 mM phosphate buffer pH 7.4, the solution was vortexed for 20 s, and the eppendorf tube was once again spun down at 10,000 g for 3 min. The supernatant was carefully removed; the pellet was resuspended in 20 µl of 20 mM phosphate buffer pH 7.4, and plated onto a glass slide. FITC was excited using a U-MWB2 filter with excitation of 460-495 nm and the fluorescence emission was collected using a 520 nm filter. A transmission image was also collected to show scaffold morphology.

Example

Cell Culture. HeLa cell lines were cultures at 37° C. with 5% $CO_2$ in DMEM medium supplemented with 10% fetal bovine serum (Cambrex Bio Science Walkersville, Inc.), 2 mM L-glutamine (Cellgro, Mediatech), and 50 units/ml penicillin and 50 µg/ml streptomycin (Cellgro, Mediatech).

Example

Cell Encapsulation Microscopy Imaging. HeLa cells were stained for 15 min with Hoescht 33342 (1.9 µM), washed with phosphate buffer saline, and trypsonized. The HeLa cells (50,000 cells) were then added to a solution containing NHbipy (1 mM), NHnbd (20 μM), phosphate buffer (20 mM, 7.4), and DMEM. Scaffold aggregation was triggered by the addition of metal ions [$Ni^{II}$, $Co^{II}$, $Cu^{II}$, $Zn^{II}$] at 1 mM and the encapsulated cells were visualized on a glass slide. Images were captured using an Optical Microscope Olympus BX51 equipped with a CCD camera. Hoescht 33342 was excited using a U-MWG2 filter with excitation of 420-480 nm and the fluorescence emission was collected using a 500 nm filter. NBD was excited using a U-MWB2 filter with excitation of 460-495 nm and the fluorescence emission was collected using a 520 nm filter.

Example

Cell Viability: Calcein-AM and MTS assay. For the calcein-AM cell viability assay, HeLa cells (50,000 cells) in DMEM were plated in a 24-well plate with a solution containing NHbipy (1 mM) and phosphate buffer (20 mM, 7.4). Scaffold aggregation was triggered by the addition of $Ni^{II}$ (1 mM) and the encapsulated cells were incubated at 37° C. with 5% $CO_2$ for 48 h. After 48 h, calcein-AM (2.5 μM) was added to each well and incubated for 30 min. Cells were then visualized using an Optical Microscope Olympus BX51 equipped with a CCD camera, and the calcein-AM was excited using a U-MWB2 filter with excitation of 460-495 nm and the fluorescence emission was collected using a 520 nm filter. A transmission image was also collected to show scaffold/cell morphology. For the MTS cell viability assay, HeLa cells alone or encapsulated as described above were incubated at 37° C. with 5% $CO_2$ in DMEM medium supplemented with 10% fetal bovine serum. After 48 h, cells were treated with 20 μl of the Cell Titer 96 A Qeous One Solution and incubated at 37° C. for 4 h. Following this incubation, the absorbance of each well was measured at 590 nm.

Example

Dynamic Light Scattering. DLS measurements were performed on a DynaPro 99 (Protein Solutions/Wyatt) with laser wavelength of 824 nm. The solutions were measured in 50 μL plastic cuvettes and were placed in a sample holder at 22° C. The intensity size distributions were obtained from the analysis of the correlation functions using a multiple spherical modes algorithm.

Example

Dynamic light scattering of H-byp. DLS was performed on a DynaPro99 (Wyatt Technology Corp) at 25° C. and solutions were filtered through a 0.45 filter. A H-byp (1 mM, 8.75 μL) solution in HEPES (10 mM, 3.5 μL, pH 7.0) was heated for 15 min at 70° C. After cooling to 25° C. various metal (Ni(II), Cu(II), Zn(II), and Fe(II)) solutions (1 mM, 4.4 μL) were added and incubated at 20° C. for 48 h prior to analysis.

A H-byp (250 μM and 50 μM, 1.5 μL) solution in HEPES (10 mM, 3.0 μL, pH 7.0) was heated for 15 min at 70° C. After cooling to 25° C. Fe(II) (125 μM and 50 μM, 0.75 μL) solutions were added and incubated at 20° C. for 48 h prior to analysis.

Example

Confocal Microscopy. For confocal microscopy images, particle solutions (25 μl) produced from the combination of NCoH peptide with zinc(II) [NCoH (1 mM) and $ZnCl_2$ (400 μM) in 20 mM MOPS pH 7.4] were incubated with 100 μM congo red. All solutions were spun at 10,000 g for 3 min and the supernatant was carefully removed. To the remaining pellet was added 100 μl of 20 mM MOPS pH 7.4, the solution was vortexed for 20 s, and the epperdorf tube was once again spun down at 10,000 g for 3 min. The supernatant was carefully removed, the particles were resuspended in 20 μl of 20 mM MOPS buffer pH 7.4, and plated onto a glass slide. Images were acquired using a Radiance 2100 MP Rainbow (Bio-Rad, Hemel Hempstead, England) on a TE2000 (Nikon, Tokyo, Japan) inverted microscope using a 60× oil 1.4 NA lens. Images were collected sequentially to avoid any possible bleed through. Congo red was excited at 543 nm using the green HeNe laser and the fluorescence emission greater than 560 nm in wavelength was collected. A transmission image was also collected to show particle morphology.

Example

Fluorescence Microscopy Imaging. For fluorescence microscopy images, particle solutions (25 μl) produced from the combination of NCoH peptide with zinc(II) [NCoH (1 mM) and $ZnCl_2$ (400 μM) in 20 mM MOPS pH 7.4] were incubated with 100 μM congo red. All solutions were spun at 10,000 g for 3 min and the supernatant was carefully removed. To the remaining pellet was added 100 μl of 20 mM MOPS pH 7.4, the solution was vortexed for 20 s, and the epperdorf tube was once again spun down at 10,000 g for 3 min. The supernatant was carefully removed, the particles were resuspended in 20 μl of 20 mM MOPS buffer pH 7.4, and plated onto a glass slide. Images were captured using an Optical Microscope Olympus BX51 equipped with a CCD camera. Congo red and doxorubicin were excited using a U-MWG2 filter with excitation of 510-550 nm and the fluorescence emission was collected using a 590 nm filter. A transmission image was also collected to show particle morphology.

Example

Animal Model for Bone Defect

Operative Procedure. Animals are anesthetized by intraperitoneal injection of 17 mg/kg sodium pentobarbital and intramuscular injection of 10 mg ketamine. The hair over the calvaria is shaved and cleaned with depilatory. Lidocaine (0.5 ml of 1%) is injected intradermally in the midline on top of the head. The rats are placed in a cephalostat and the skin is incised in the midline. Using an operating microscope, the subcutaneous fascia is divided, the periosteum is incised in the midline, and periosteal flaps are reflected laterally.

An 8-mm circular CSD is templated and excavated centrally over the parietal bones using a drill with saline irrigation. Extreme care should be taken not to damage the dura mater. After copious irrigation with normal saline, gels are placed in the defects (except in controls), and the defects are completely covered by closure of the periosteum using 10-0 nylon suture. The skin is closed using 4-0 nylon suture.

Animal Model, Experimental Design, and Data Analysis. Thirty-six 6- to 7-month-old, retired breeder, Sprague-Dawley rats, weighing 410 to 576 g each, are randomly assigned to seven groups of animals. Six animals in Group 1 (control) receive no treatment for the calvarial defects. Group 2 (six animals) is implanted with 50 ml of 3% methylcellulose, a volume sufficient to fill the defect cavity. Groups 3, 4, and 5 (six rats per group) are implanted with 100 ml gels of type I collagen, reconstituted basement membrane, or laminin, respectively. Bone repair in Groups 1, 2, 4; and 5 is evaluated using a single computerized tomography (CT) scan in each of these groups at 12 weeks. Rats treated with type I collagen (Group 3) undergo scanning biweekly from 2 to 12 weeks to evaluate the kinetics of healing. If 100 ml of type I collagen gels contract and do not completely fill the depth of the defects after closure of the periosteum, an additional group of three rats (Group 6) may be implanted with 150 ml of type I collagen gels. These rats are sacrificed following a single CT scan at 12 weeks. The last group of three animals (Group 7) is implanted with 100 ml of type I collagen gels (identical to Group 3) and sacrificed at 20 weeks following a single CT scan to determine if complete healing has occurred.

CT scans. Animals are anesthetized by a 40-mg injection of ketamine given intramuscularly in a hindlimb. Five rats undergo scanning simultaneously in the prone position using a scanner with a standard bone window algorithm. Serial 1.5-mm width scans are made from just anterior to the orbit through the occiput. The area of new bone in defects is determined after three dimensional reconstruction of the CT scans using commercially available hardware (Voxel Flinger) and software packages. Tapes from the scanner are read into the Voxel Flinger and three-dimensional reconstructions are automatically performed by selecting an individual study. Measurement functions of the Voxel Flinger are used manually to delineate the remaining unrepaired area within defects after three-dimensional reconstruction. The unrepaired area in the defect is then calculated automatically. Results are presented as mean percent healing of defects by area (6 standard deviation). Results using this method should correlate well with area measurements from contact radiographs and histomorphometry of bone repair in this CSD.

All animals in Groups 1 to 6 are sacrificed at 12 weeks. Animals in Group 7 are sacrificed at 20 weeks: After sacrifice, the calvarial defects are examined, photographed, excised, and fixed in 10% buffered formalin. Three specimens from each of Groups 1 to 5, chosen at random, are decalcified with ethylenediamine tetraacetic acid/HCl, cut in a coronal plane in the center of the defect, embedded in paraffin, sectioned, and stained with hematoxylin and eosin.

Percent healing of CSDs is analyzed using analysis of variance. The Ryan-Einot-Gabriel-Welsch multiple F-test may be used to identify significant differences between groups. The level of significance for F-tests should be p=0.05.

Additional optional aspects of the model are described in Sweeney et al., "Repair of critical size rat calvarial defects using extracellular matrix protein gels", J Neurosurg 83:710-715, 1995.

What is claimed is:

1. A synthetic collagen conjugate capable of forming a type II helix, the conjugate comprising one or more metal-binding moieties, and a peptide comprising a plurality of tripeptides, each of which comprises proline or hydroxyproline, or a combination thereof; where the one or more metal-binding moieties are covalently attached to the peptide, optionally with a divalent linker;

wherein one of said metal-binding moieties is covalently attached to the N-terminus of the peptide, and one of said metal-binding moieties is covalently attached to the C-terminus of the peptide; or wherein one of said one or more metal-binding moieties is covalently attached to a non-terminal amino acid of the peptide; or wherein one of said metal-binding moieties is covalently attached to the N-terminus of the peptide, one of said metal-binding moieties is covalently attached to the C-terminus of the peptide, and one of said metal-binding moieties is covalently attached to a non-terminal amino acid of the peptide; and wherein the conjugate may further comprise a drug or a diagnostic or imaging agent, where the drug or the diagnostic or imaging agent is covalently attached to the peptide, optionally with a divalent linker.

2. The conjugate of claim 1 wherein the peptide comprises a plurality of tripeptides, each of which comprises glycine and proline.

3. The conjugate of claim 1 wherein the peptide comprises a plurality of tripeptides, each of which comprises glycine and hydroxyproline.

4. The conjugate of claim 1 wherein one of said metal-binding moieties is covalently attached to the N-terminus of the peptide, and one of said metal-binding moieties is covalently attached to the C-terminus of the peptide.

5. The conjugate of claim 1 wherein the conjugate is capable of forming a self assembling triple helix.

6. The conjugate of claim 5 wherein the triple helix is capable of aggregating in the presence of a transition metal.

7. The conjugate of claim 1 wherein the peptide is at least about 18 amino acids in length.

8. The conjugate of claim 1 wherein the peptide is between about 18 and about 54 amino acids in length.

9. The conjugate of claim 1 wherein the peptide comprises at least about 25% glycine.

10. The conjugate of claim 1 wherein the peptide comprises at least about 5% proline.

11. The conjugate of claim 1 wherein the peptide comprises a plurality of divalent tripeptides selected from the group consisting of Xaa-Yaa-Gly, Gly-Pro-Xaa and Gly-Xaa-Hyp, or a combination thereof, where each Xaa and Yaa is independently selected in each instance from the group consisting of naturally occurring amino acids and derivatives of naturally occurring amino acids.

12. The conjugate of claim 1 wherein one or more of the metal-binding moieties is selected from the group consisting of bipyridinyls, amino bis(acetic acid)s, and $His_x$, where x is an integer from 2 to 4, and amides thereof, and pharmaceutically acceptable salts thereof.

13. The conjugate of claim 1 wherein one or more of the metal-binding moieties is capable of binding a metal cation selected from the group consisting of cations of iron, nickel, cobalt, copper, zinc, and ruthenium, and combinations thereof.

14. The conjugate of claim 1 further comprising a drug or a diagnostic or imaging agent, where the drug or the diagnostic or imaging agent is covalently attached to the peptide, optionally with a divalent linker.

15. The conjugate of claim 14 wherein the drug is a compound capable of treating a bone or cartilage disease.

16. The conjugate of claim 14 wherein the drug or the diagnostic or imaging agent is selected from the group consisting of cell adhesion agents, growth factors, integrin binding domain peptides, REDV peptides, RGD peptides, YIGSR peptides, vascular endothelial growth factors, transforming growth factors, bone morphogenetic protein 2, epidermal growth factors, fibroblast growth factors, hepatocyte growth factors, biotin, bone antiresorptive agents, parathyroid hormone, parathyroid hormone fragments, and NBD fluorophores.

17. The conjugate of claim 1 wherein one of said one or more metal-binding moieties is covalently attached to a non-terminal amino acid of the peptide.

18. The conjugate of claim 1 wherein one of said metal-binding moieties is covalently attached to the N-terminus of the peptide, one of said metal-binding moieties is covalently attached to the C-terminus of the peptide, and one of said metal-binding moieties is covalently attached to a non-terminal amino acid of the peptide.

19. The conjugate of claim 1 having a nitrilotriacetic acid (NTA) unit at the N-terminus and a His$_2$ unit at the C-terminus.

20. The conjugate of claim 1 wherein an N-terminal metal-binding ligand, if present, comprises a residue having the formula a C-terminal metal-binding ligand, if present, comprises a His-His-NH$_2$ residue; and a metal-binding ligand attached to a non-terminal amino acid, if present, comprises a 4'-methyl-2,2'-bipyridine-4-carbonyl or an iminodiacetate residue.

21. The conjugate of claim 1 which is selected from the group consisting of

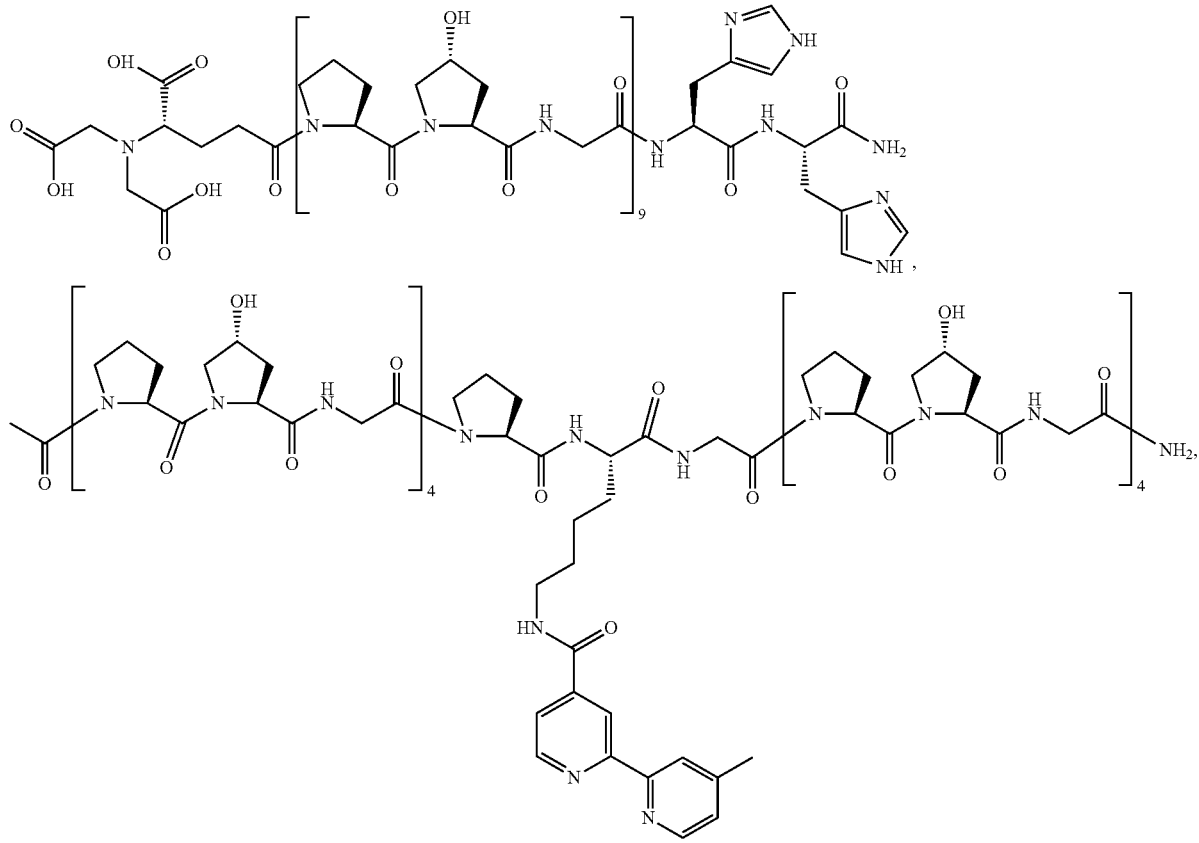

and

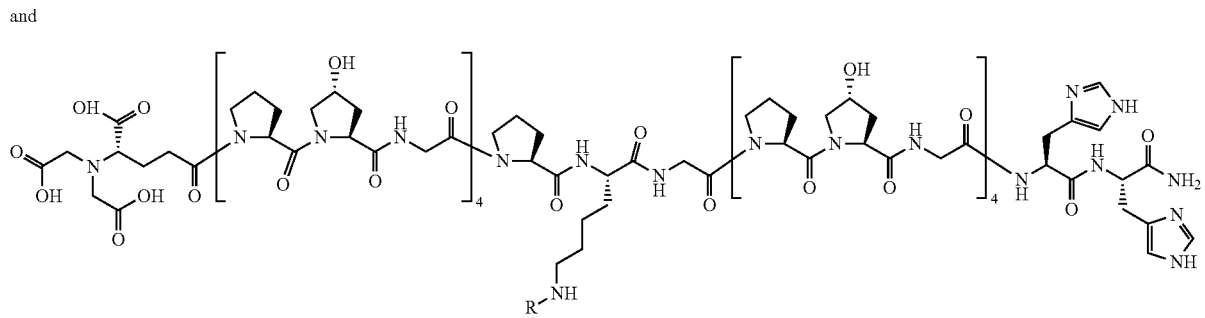

in which R is

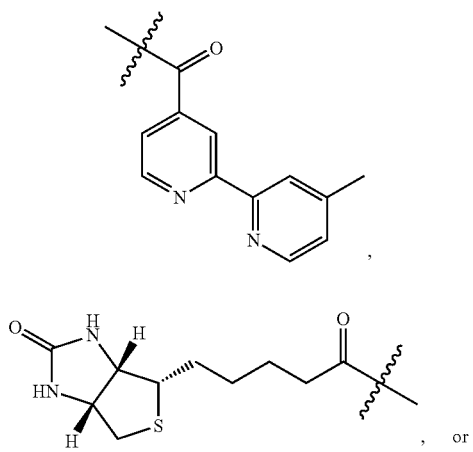, or

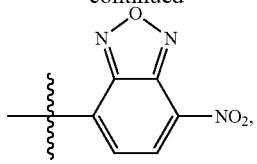

or

R is an RGD-based peptide.

22. A collagen composition comprising a collagen and one or more conjugates of claim 1.

23. A composition comprising one or more conjugates of claim 1 and one or more populations of cells.

24. The composition of claim 23 wherein the population of cells is selected from the group consisting of adipose derived stem cells (ASC), human umbilical vein endothelial cells (HUVEC), mesenchymal stem cells (MSC), and combinations thereof.

* * * * *